(12) United States Patent
Perin et al.

(10) Patent No.: US 11,840,683 B2
(45) Date of Patent: Dec. 12, 2023

(54) GLOMERULUS ON A CHIP TO RECAPITULATE GLOMERULAR FILTRATION BARRIER

(71) Applicant: Children's Hospital Los Angeles, Los Angeles, CA (US)

(72) Inventors: Laura Perin, Burbank, CA (US); Stefano Da Sacco, Glendale, CA (US); Roger De Filippo, Glendale, CA (US)

(73) Assignee: Children's Hospital Los Angeles, Los Angeles, CA (US)

( * ) Notice: Subject to any disclaimer, the term of this patent is extended or adjusted under 35 U.S.C. 154(b) by 170 days.

(21) Appl. No.: 16/870,480

(22) Filed: May 8, 2020

(65) Prior Publication Data

US 2020/0354663 A1 Nov. 12, 2020

Related U.S. Application Data

(60) Provisional application No. 62/846,112, filed on May 10, 2019.

(51) Int. Cl.
*C12M 3/06* (2006.01)
*C12M 1/12* (2006.01)
(Continued)

(52) U.S. Cl.
CPC ............ *C12M 23/16* (2013.01); *C12M 25/02* (2013.01); *C12M 29/10* (2013.01); *C12N 5/0686* (2013.01); *G01N 33/5088* (2013.01)

(58) Field of Classification Search
CPC ...... C12M 23/16; C12M 23/20; C12M 25/02; C12M 29/10; C12M 21/08; C12N 5/0686; G01N 33/5088
See application file for complete search history.

(56) References Cited

U.S. PATENT DOCUMENTS

2008/0233607 A1* 9/2008 Yu .......................... C12M 23/34
435/299.1
2011/0159522 A1* 6/2011 Kamm ............... G01N 33/5029
435/287.1
(Continued)

FOREIGN PATENT DOCUMENTS

CN 105420106 3/2016
CN 107955783 4/2018
(Continued)

OTHER PUBLICATIONS

"International Application Serial No. PCT US2020 032163, International Preliminary Report on Patentability dated Nov. 25, 2021", 7 pages.
(Continued)

*Primary Examiner* — Michael L Hobbs
(74) *Attorney, Agent, or Firm* — Schwegman, Lundberg & Woessner, P.A.

(57) ABSTRACT

A glomerulus on a chip (GOAC) to recapitulate the human glomerular filtration barrier, the structure responsible for filtering the blood and preventing the loss of proteins, is provided using human podocytes and glomerular endothelial cells seeded into microfluidic chips. In long-term cultures, cells maintain their morphology, form capillary-like structures and express slit diaphragm proteins. This system recapitulates functions and structure of the glomerulus, including permselectivity. When exposed to sera from patients with anti-podocyte autoantibodies, the chips show albuminuria proportional to patients' proteinuria, phenomenon not observed with sera from healthy controls or individuals with primary podocyte defects. Also shown is its applicability for renal disease modeling and drug testing.

14 Claims, 47 Drawing Sheets

(51) Int. Cl.
*C12N 5/071* (2010.01)
*C12M 1/00* (2006.01)
*G01N 33/50* (2006.01)

(56) References Cited

U.S. PATENT DOCUMENTS

| | | | |
|---|---|---|---|
| 2011/0186165 A1* | 8/2011 | Borenstein | C12M 23/16 156/196 |
| 2018/0298343 A1* | 10/2018 | Sivakumaran | C12N 5/0691 |

FOREIGN PATENT DOCUMENTS

| | | | | |
|---|---|---|---|---|
| CN | 107955786 | | 4/2018 | |
| CN | 108485975 | | 9/2018 | |
| WO | WO-2016207654 A1 * | 12/2016 | | A61K 35/22 |
| WO | 2020231833 | | 11/2020 | |

OTHER PUBLICATIONS

"International Application Serial No. PCT US2020 032163, International Search Report dated Sep. 15, 2020", 4 pgs.

"International Application Serial No. PCT US2020 032163, Written Opinion dated Sep. 15, 2020", 5 pgs.

"European Application Serial No. 20730798.4, Response filed Jun. 16, 2022 to Communication Pursuant to Article 94(3) EPC dated Dec. 1, 2021", 9 pgs.

Hoppensack, A, et al., "A human in vitro model that mimics the renal proximal tubule", Tissue Engineering, Part C, vol. 20, No. 7, (2014), 599-609.

Huh, D, et al., "Microfabrication of human organs-on-chips", Nat. Protoc. 8(11), (2013), 2135-2157.

Jang, Kyung-Jin, et al., "Human kidney proximal tubule-on-a-chip for drug transport and nephrotoxicity assessment", Integr. Biol, 5,, (2013), 1119-1129.

Kelly, E J, et al., "Innovations in preclinical biology: ex vivo engineering of a human kidney tissue microperfusion system", Stem Cell Res. Ther. 4(Suppl. 1), [Online]. Retrieved from the Internet: <URL: http://stemcellres.com/content/4/S1/S17>, (2013).

Musah, S, et al., "Mature induced-pluripotent-stem-cell-derived human podocytes reconstitute kidney glomerular-capillary-wall function on a chip", Nat Biomed Eng., (2017), 25 pgs.

Petrosyan, A, et al., "A glomerulus-on-a-chip to recapitulate the human glomerular filtration barrier", Nature Communications, (2019), 17 pgs.

Schutgens, Frans, et al., "Tubuloids derived from human adult kidney and urine for personalized disease modeling", Nature Biotechnology, (2019), 18 pgs.

Suter-Dick, Laura, et al., "Combining Extracellular miRNA Determination with Microfluidic 3D Cell Cultures for the Assessment of Nephrotoxicity: a Proof of Concept Study", AAPS Journal, 20:86, (2018), 9 pgs.

Vormann, Marianne, et al., "Nephrotoxicity and Kidney Transport Assessment on 3D Perfused Proximal Tubules.", AAPS Journal, 20:90, (2018), 11 pgs.

Vriend, J, et al., "Screening of Drug-Transporter Interactions in a 3D Micro?uidic Renal Proximal Tubule on a Chip", AAPS Journal, 20, 87, (2018), 13 pgs.

Wang, L, et al., "A disease model of diabetic nephropathy in a glomerulus-on-a-chip microdevice", Lab Chip, 17(10), (2017), 1749-1760.

Wilmer, M, et al., "Kidney-on-a-Chip Technology for Drug-Induced Nephrotoxicity Screening", Trends Biotechnol. 34(2) 156-170 (2016)., (Feb. 2016), 156-170.

Zhou, M, et al., "Development of a Functional Glomerulus at the Organ Level on a Chip to Mimic Hypertensive Nephropathy", Sci. Rep. 6, 31771, (2016), 13 pgs.

* cited by examiner

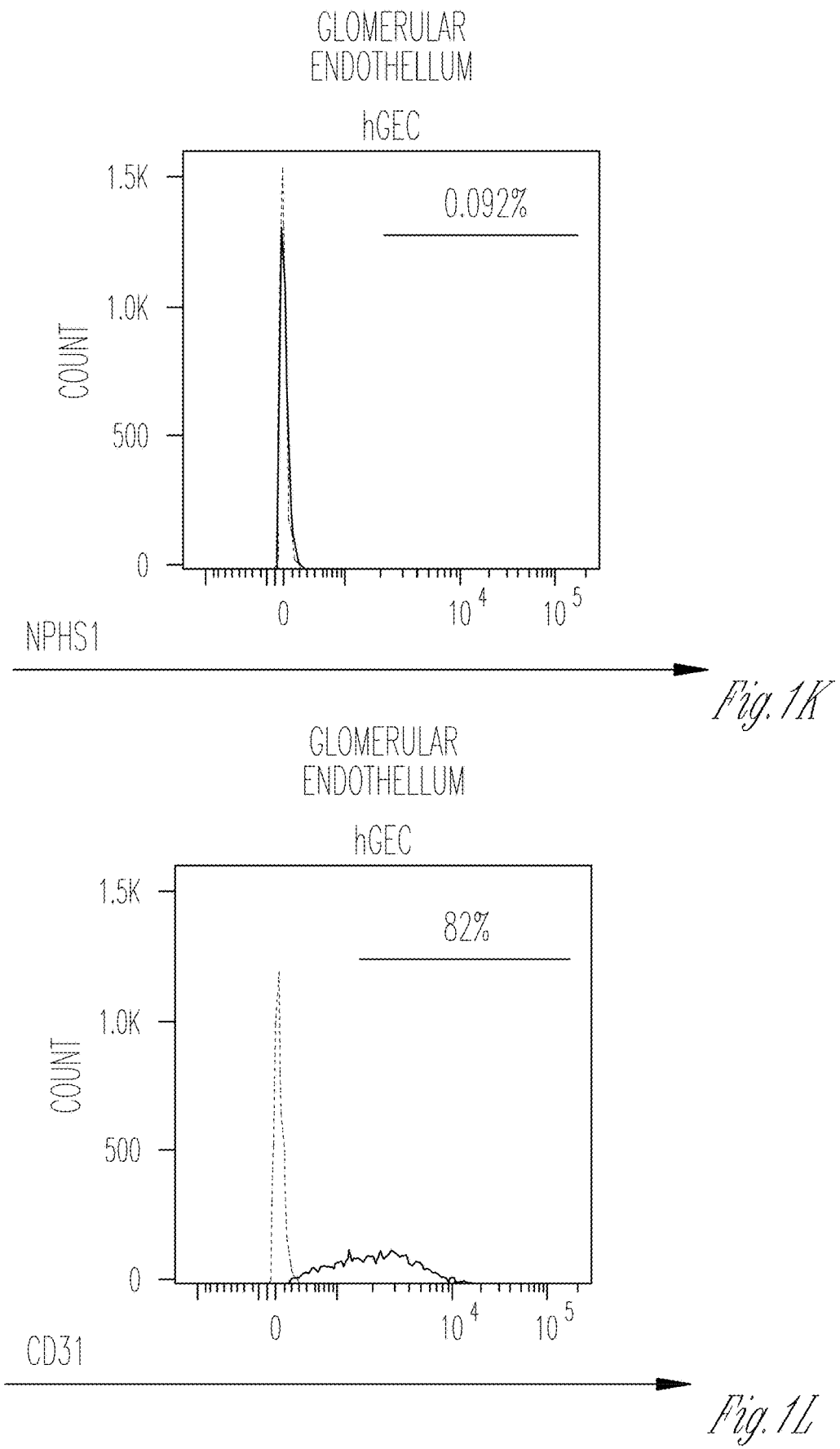

5 min 60 min hAKPC-P

*Fig. 4B*

5 min 60 min hiPOD

*Fig. 4C*

5 min 60 min hpPOD

*Fig. 4D*

| SAMPLE | SEX | AGE | PROTEINURIA (g/24 h) | CREATININE (mg/dl) |
|---|---|---|---|---|
| CTRL1 | M | 43 | 0 | 1.2 |
| CTRL2 | F | 32 | 0 | 0.8 |
| MN1 | M | 73 | 13.4 | 0.9 |
| MN2 | F | 30 | 8.6 | 0.67 |
| MN3 | M | 70 | 6.51 | 0.97 |
| MN4 | M | 47 | 4 | 0.77 |
| MN5 | F | 41 | 2.4 | 0.76 |
| MN6 | F | 30 | 3.6 | 0.53 |

*Fig. 6A*

GLOMERULUS ON A CHIP TO RECAPITULATE GLOMERULAR FILTRATION BARRIER

PRIORITY

This application claims the benefit of priority to U.S. Provisional Patent Application No. 62/846,112, filed on May 10, 2019, the disclosure of which is incorporated herein by reference in its entirety.

BACKGROUND OF THE INVENTION

Over 10% of adults worldwide are affected by renal abnormalities and the number of those with end-stage renal disease receiving replacement therapy with dialysis or transplant is estimated at >1.4 million, with an annual growth rate of 8% (1). Major progresses in understanding environmental and genetic risk factors, as well as pathogenic mechanisms of renal disease progression have been accomplished, but outcomes of affected individuals have not appreciably improved over the last two decades (1).

Despite a wide variety of causes, including metabolic abnormalities, hypertension, autoimmunity, and genetic background, a common early pathologic hallmark of chronic kidney disease (CKD) is decreased glomerular filtration function and loss of functional glomeruli (2). The main function of glomeruli is to filter fluids and electrolytes from the blood, while retaining plasma proteins (3). This activity happens at the level of the glomerular filtration barrier (GFB) and is coordinated by the interaction of two highly specialized glomerular cells (the fenestrated endothelium and the podocytes), which are separated by a thin layer of glomerular basement membrane (GBM, (4)).

SUMMARY OF THE INVENTION

One embodiment provides for a glomerulus on a chip (GOAC) device comprising at least three channels, at least two monolayers of cells and a glomerular renal filtration barrier, wherein the device does not include an artificial membrane separating layers of cells within the device. In one embodiment the cells include at least one of podocytes, glomerular endothelial cells (GEC), or a combination thereof. In one embodiment, the podocytes are at least one of primary podocytes (hpPOD), immortalized podocytes (hiPOD), amniotic fluid derived podocytes (hAKPC-P) or a combination thereof. In another embodiment, the cells are human. In one embodiment, the cells are obtained from a subject that does not have a kidney disease or disorder. Another embodiment provides a for where the cells are obtained from a subject with a kidney disease or disorder, such as focal segmental glomerulosclerosis (FSGS), chronic kidney disease (CKD), Alport syndrome (AS), Pearson Syndrome, polycystic kidney disease (PKD), genetic kidney disease, thin basement membrane disease, nephrotic syndrome, minimal change disease, IgA nephropathy, Goodpasture syndrome, glomerulopathies, APOL1 mutations, diabetic nephropathy, membranous nephropathy, focal segmental glomerulosclerosis, membranoproliferative glomerulonephritis, diffuse proliferative glomerulonephritis, membranous focal segmental glomerulosclerosis, mesangial proliferative glomerulonephritis, capillary glomerulonephritis, crescentic glomerulonephritis, sclerosing glomerulonephritis, ischemic nephropathy, glomerular disease based on systemic disease, glomerular diseases based on vascular disease, glomerular disease based on metabolic diseases, hereditary renal lesions, transplanted glomerular lesions, kidney cancer, cancer or hypoplastic kidney. In embodiment, the GOAC comprises a first channel, a second channel and a third channel. In one embodiment, the first channel comprises a gelified collagen, such as collagen I or IV. In another, the second channel comprises cells. And in another embodiment, the third channel collects filtrate. In one embodiment, the GOAC provides the permselectivity, such as the ability to filtrate out inulin and retain of albumin. In one embodiment, the GOAC comprises at least podocyte and glomerular endothelial cells, wherein the podocytes can form slit diaphragm and the endothelial cells can form capillary structures.

Another embodiment provides a method of providing a glomerulus on-a-chip (GOAC) device with at least three channels comprising: i) load a first channel with collagen; ii) load a second channel with one or more cell types after which fill said second channel with growth medium; and iii) a third channel to collect filtrate. In one embodiment, the cells include at least one of podocytes, glomerular endothelial cells (GEC), or a combination thereof. In another embodiment, the podocytes are at least one of primary podocytes (hpPOD), immortalized podocytes (hiPOD), amniotic fluid derived podocytes (hAKPC-P) or a combination thereof. In one embodiment, the cells are human. In one embodiment, the cells are obtained from a subject that does not have a kidney disease or disorder. In another embodiment, the cells are obtained from a subject with a kidney disease or disorder, such as focal segmental glomerulosclerosis (FSGS), chronic kidney disease (CKD), Alport syndrome (AS), Pearson Syndrome, polycystic kidney disease (PKD), genetic kidney disease, thin basement membrane disease, nephrotic syndrome, minimal change disease, IgA nephropathy, Goodpasture syndrome, glomerulopathies, APOL1 mutations, diabetic nephropathy, membranous nephropathy, focal segmental glomerulosclerosis, membranoproliferative glomerulonephritis, diffuse proliferative glomerulonephritis, membranous focal segmental glomerulosclerosis, mesangial proliferative glomerulonephritis, capillary glomerulonephritis, crescentic glomerulonephritis, sclerosing glomerulonephritis, ischemic nephropathy, glomerular disease based on systemic disease, glomerular diseases based on vascular disease, glomerular disease based on metabolic diseases, hereditary renal lesions, transplanted glomerular lesions, kidney cancer, cancer or hypoplastic kidney. In one embodiment, the first channel comprises a gelified collagen, such as collagen I or IV. In one embodiment, the second channel comprises cells. In another embodiment, the third channel collects filtrate. In one embodiment, the GOAC provides the permselectivity, wherein the permselectivity results in filtration of inulin and the retention of albumin. In one embodiment, the GOAC comprises at least podocyte and glomerular endothelial cells. In one embodiment, the first channel is filled with collagen I, after gelification of said collagen, then podocytes are seeded in second channel, after seeding of said podocytes, then endothelial cells are seeded in the second channel. In one embodiment, the podocytes form slit diaphragm and the endothelial cells form capillary structures. In another embodiment, the cells maintain their phenotype and secrete glomerular membrane with deposition collagen IV and/or laminin. In one embodiment, the cells are incubated in the device for at least 45 days. In another embodiment, the device comprises two monolayers, wherein each monolayer is made up cell types different from the other monolayer, wherein the device does not comprise an artificial membrane separating the monolayers.

One embodiment provides a glomerulus-on-a-chip (GOAC) device prepared by the method of the instant claims.

Another embodiment provides a method for testing the effect of at least one test compound on the instant glomerulus-on-a-chip (GOAC) device comprising adding the at least one test compound to the GOAC and assessing GOAC microscopically and/or determining one or more physiological parameters of GOAC. One embodiment further comprises determining at least one of efficacy, side-effect, biosafety or mode of action of the at least one test compound.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4A-K. GOAC and puromycin aminonucleoside (PAN) injury. A Representation of GOAC albumin permselectivity assay following PAN injury: PAN (5-day induction, 10 mg/ml) is applied to channel C followed by albumin-FITC (40 mg/ml) and flow-through collected in channel F. B-D Bright field showing albumin leakage after 5 min (left columns) and 60 min (right columns) in hAKPC-P+hGEC chip (B), in hiPOD+hGEC chip (C), in hpPOD+hGEC (D) after PAN injury. Marked albumin leakage occurs following podocyte injury. E-J Damage to podocytes was assessed by F-actin staining in hAKPC-P+hGEC chip before (E) and after PAN damage (F), in hiPOD+hGEC chip before (G) and after PAN damage (H), and in hpPOD+hGEC before (I) and after PAN damage (J) confirming widespread disruption of the cytoskeleton. Nuclei are stained with DAPI; actin filaments stained with phalloidin. All pictures: scale bar=50 μm; K box plot graph of fluorescein absorbance (expressed as log) in filtrate collected after 60 min after 5 days exposure to PAN. For all experimental groups, a marked and statistically significant increase was found in albumin permeability following injury. Number of replicates for chips used in K is as follows: hAKPC-P+hGEC chip: #12 and #4; hiPOD+hGEC chip: #6 and #4; hpPOD+hGEC chip: #7 and #3. Significant differences were determined by a one-way ANOVA and Holm-Sidak post hoc test, *$p<0.05$, $p<0.01$, *$p<0.001$. (To improve clarity, the following significant differences were not drawn in the graph: hiPOD+hGEC+PAN vs. hAKPC-P+hGEC $p<0.001$; hiPOD+hGEC+PAN vs. hpPOD+hGEC $p<0.001$; hpPOD+hGEC+PAN vs. hAKPC-P+hGEC $p<0.001$; hpPOD+hGEC+PAN vs. hiPOD+hGEC $p<0.001$; hAKPC-P+hGEC+PAN vs. hpPOD+hGEC $p<0.001$; hAKPC-P+hGEC+PAN vs. hiPOD+hGEC $p<0.05$; hiPOD+hGEC+PAN vs. hAKPC-P+hGEC+PAN $p<0.05$.) Box plots show the median, the 25th and 75th percentiles, whiskers (median±1.5 times interquartile range), and outliers (solid circle).

FIGS. 6A-H. Correlation of GOAC proteinuria with clinical data and MN mechanism modeling on the chip. A Table of clinical parameters for proteinuria in MN serum samples used on the GOAC. B hAKPC-P+hGEC chip proteinuria for CTRL1-2 and MN1-6 clinical proteinuria levels suggests a very strong correlation between clinical profile and response in the chip (measured as albumin leakage). R: 0.8901, $P<0.01$. C hiPOD+hGEC chip proteinuria for CTRL1-2 and MN1-6 clinical proteinuria levels suggest a weak correlation between clinical profile and response in the chip (measured as albumin leakage). R: 0.3156, not significant. D hpPOD+hGEC chip proteinuria for CTRL1-2 and MN1-6 clinical proteinuria levels suggest a strong correlation between clinical profile and response in the chip (measured as albumin leakage). R: 0.7995, $p<0.05$. For all samples, regression analysis was performed. Equation: Polynomial, linear. Blue lines=95% confidence band; red lines=95% prediction band. E, F Western blot analysis for C3d (140 kDA) and beta actin (40 kDa) in hAKPC-P+hGEC, hiPOD+hGEC, and hpPOD+hGEC chips exposed to healthy or MN serum confirmed increased expression for C3d by all three MN chips. Number of replicates per experimental group: 3 (F). Quantification of C3d expression was performed by measuring pixel density and followed by normalization against beta actin. G, H Western blot analysis for NPHS1 (138 kDA) and beta actin (40 kDa) in hAKPC-P+hGEC, hiPOD+hGEC, and hpPOD+hGEC chips exposed to healthy or MN serum confirmed decreased expression for NPHS1 by all three MN chips. Number of replicates per experimental group: 3. H Quantification of NPHS1 expression was performed by measuring pixel density and followed by normalization against beta actin (G). For all samples lack of significant differences was determined by a one-way ANOVA and Student-Newman Keuls post hoc test. Box plots show the median, the 25th and 75th percentiles, whiskers (median±1.5 times interquartile range), and outliers (solid circle).

Figure 1A:
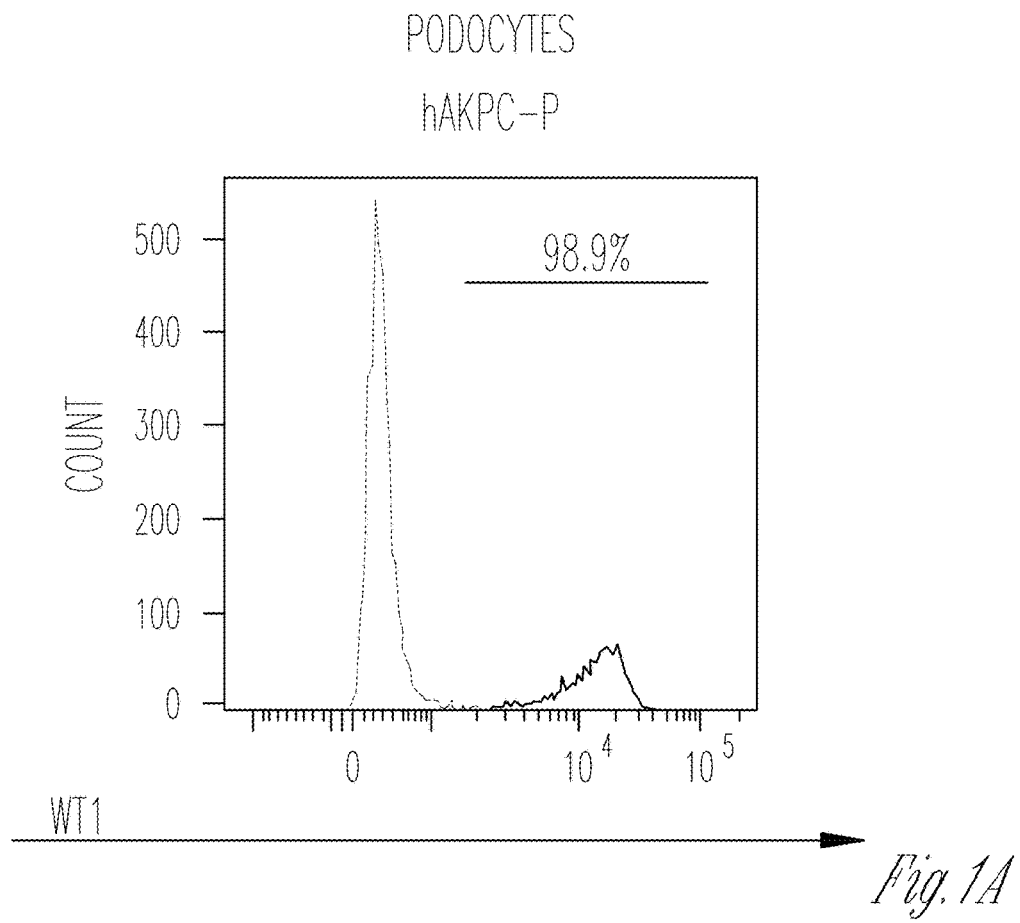
FIGS. 1A-T. Characterization of cellular lines and description of the microfluidic chip. A-I Flow cytometry for WT1 (PE) in hAKPC-P (A), hiPOD (B), and hpPOD (C); for nephrin (NPHS1-FITC) in hAKPC-P (D), hiPOD (E), and hpPOD (F) and for CD31 (FITC) in hAKPC-P (G), hiPOD (H), and hpPOD (I). All three lines show almost 100% expression of podocyte markers and absence of endothelial marker confirming their podocyte phenotype. J-L Flow cytometry for WT1 (PE, J), for nephrin (NPHS1-FITC, K), and for CD31 (FITC, L) in hGEC show low expression (<1%) of podocyte markers and higher expression of endothelial marker confirming their endothelial phenotype. M-R Flow cytometry for WT1 (PE) in HuLEC (M) and hFIB (P), for nephrin (NPHS1-FITC) in HuLEC (N) and hFIB (Q), and for CD31 (FITC) in HuLEC (O) and hFIB (R). HuLEC and hFIB are both negative for podocyte makers, HuLEC are positive for endothelial marker while hFIB are negative. Unstained control is shown in red while stained sample is shown in light blue. S, T The chip is a microfluidic layer sandwiched between two 175 µm glass plates (OrganoPlate™ platform, courtesy of MIMETAS™, panel s). The three-channel version of the Organoplate™ comprises 40 networks on one 96-well format plate. T The central section is subdivided into three channels by a system known as PhaseGuide™, a thin 30 µm tall ridge that acts as a pinning barrier for incoming fluids (23). Following the filling of channel E with collagen I, channel C (representing the vascular space) is seeded with cells and then filled with growth medium; the channel F (representing the urinary space) is where the filtrate is collected. Cross-section depicts patterning of cells and collagen within the GOAC. Flow of culture medium is achieved by leveling between the media reservoirs of the lanes C and F. The platform is placed on an interval rocker, with an angle to assure leveling. By changing the angle of the platform (rocker settings: interval=8 min, angle=7°), the direction of fluid flow is reversed.
Figure 1B:
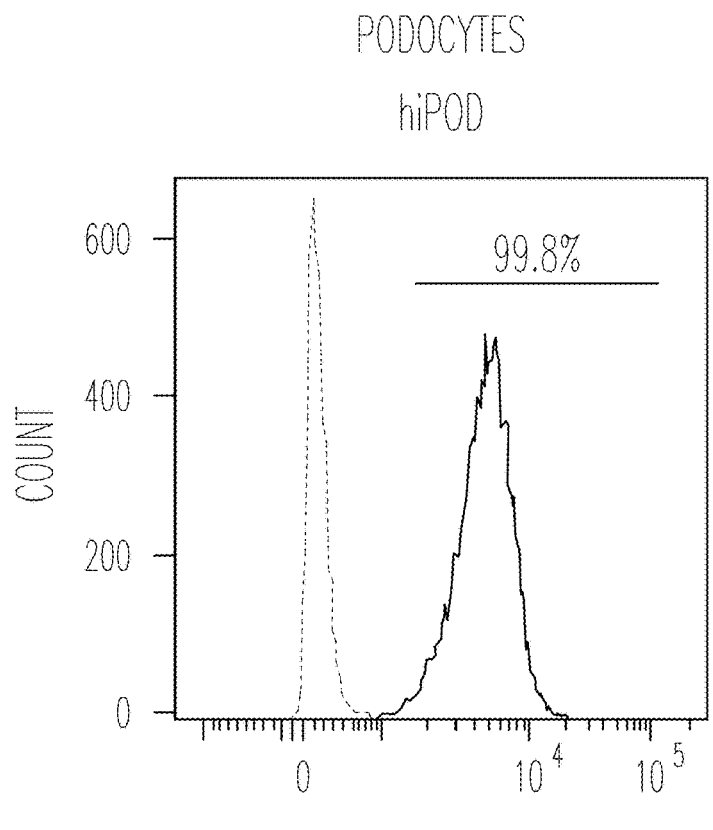
Figure 1C:
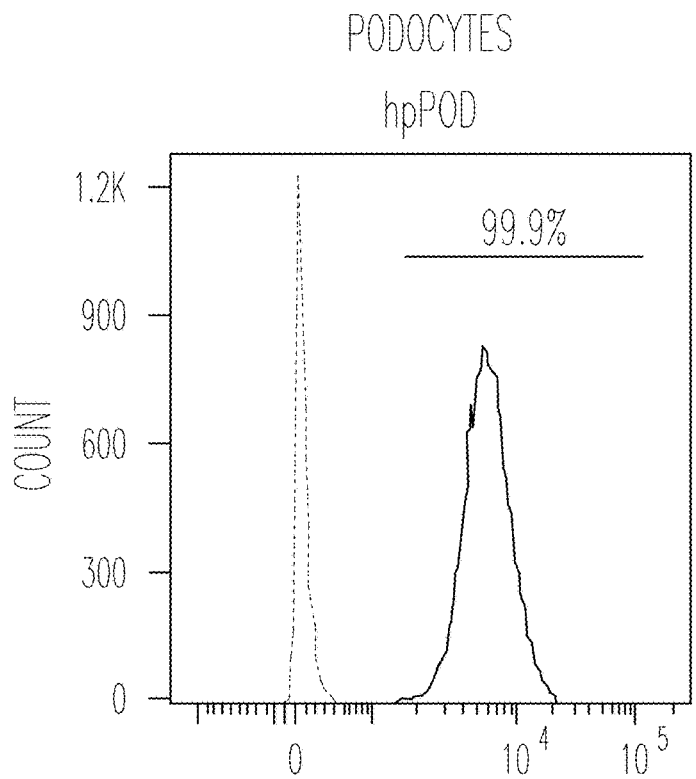
Figure 1D:
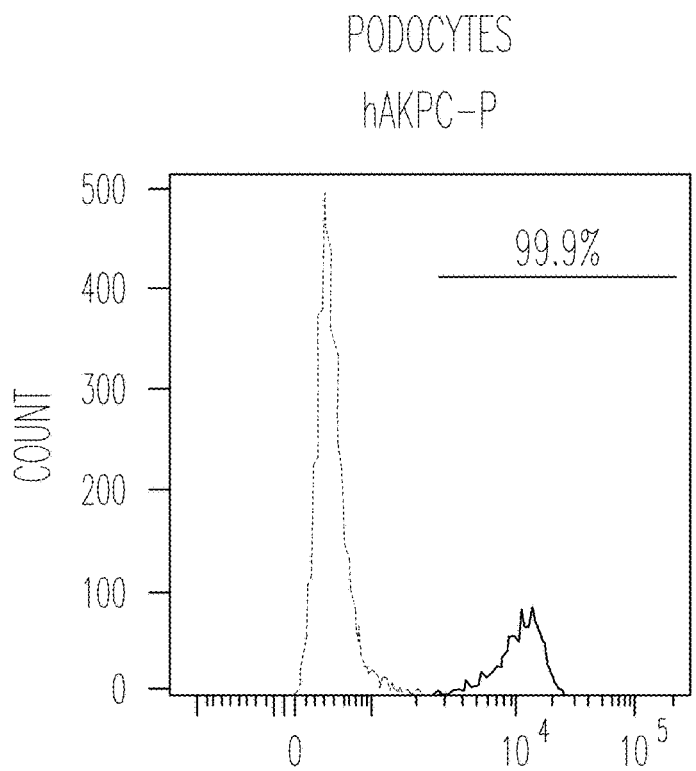
Figure 1E:
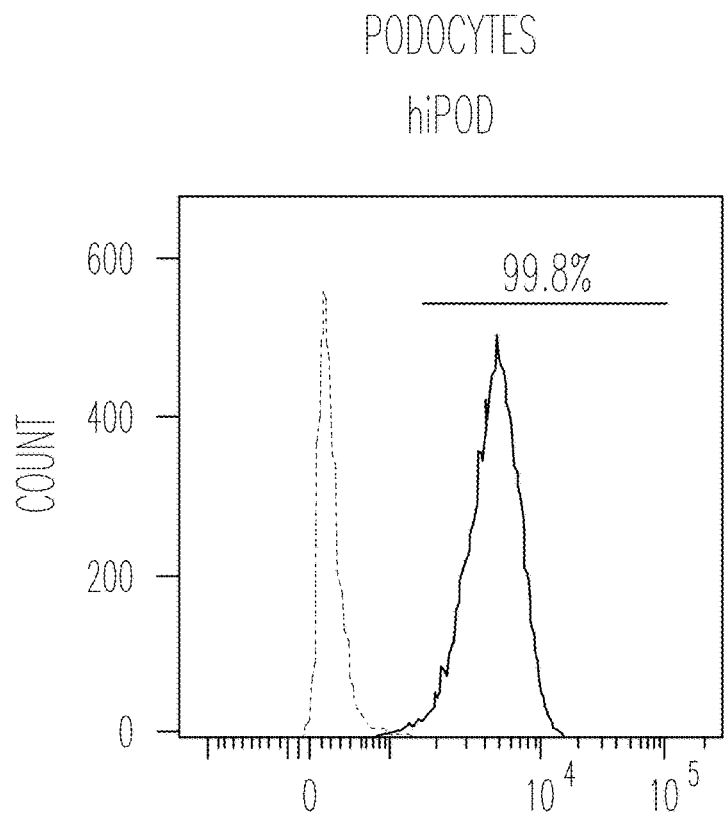
Figure 1F:
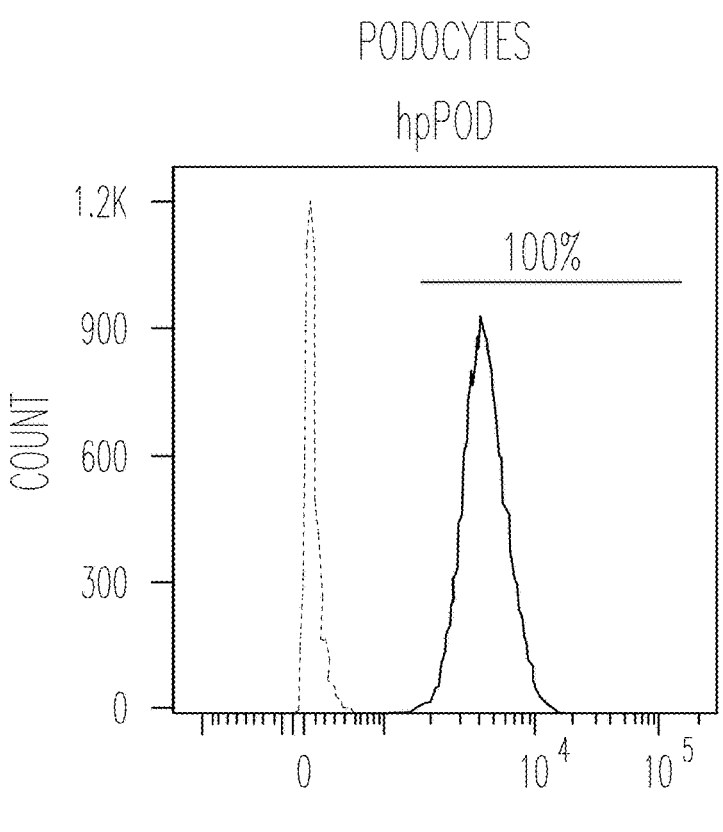

D Box plot graph of fluorescein absorbance in filtrate after 60 min following 24 h incubation with serum from healthy individuals or MN with or without supplementation with 10 ng/ml of α-MSH for 24 h. Quantification of proteinuria (albumin-FITC) was performed by measuring absorbance (fluorescein, 0.1 s) of flow-through for hAKPC-P+hGEC at 60 min Number of replicates for chips used in D is as follows: CTRL2: #6; MN3: #9; MN3+a-MSH: #11. Significant differences were determined by a one-way ANOVA and Holm-Sidak post hoc test. Box plots show the median, the 25th and 75th percentiles, whiskers (median±1.5 times interquartile range), and outliers (solid circle).

FIGS. 8A-D. Validation of the hAKPC-P GOAC system as disease-modeling platform (221). A Scheme of GOAC albumin permselectivity assay and exposure to glucose at different concentrations (10, 15, 20 mM). Following a 72-h incubation, albumin-FITC is applied to channel C and flow-through presents in channel F. B Box plot graph of fluorescein absorbance in filtrate collected after 60 min following 72 h incubation with 10-20 mM glucose. Number of replicates for chips used in B is as follows: 10 mM: #7; 15 mM: #8; 20 mM: #9. C Scheme of GOAC albumin permselectivity assay with AS-hAKPC-P+hGEC. Following formation of the AS podocyte-endothelial cell layer, albumin-FITC is applied to channel C and flow-through presents in channel F. D Box plot graph of fluorescein absorbance in filtrate after 60 min. Quantification of proteinuria (albumin-FITC) was performed by measuring absorbance (fluorescein, 0.1 s) of flow-through for AS-hAKPC-P+hGEC at 60 min. Number of replicates for chips used in D is as follows: hAKPC-P=hGEC: #12; AShAKPC-P+hGEC: #7. Significant differences were determined by a one-way ANOVA and Holm-Sidak post hoc test. Box plots show the median, the $25^{th}$ and 75th percentiles, whiskers (median±1.5 times interquartile range), and outliers (solid circle).

DETAILED DESCRIPTION OF THE INVENTION

One of the major roadblocks to the development of successful therapeutics for CKD depends on the ability to effectively develop 3D models that can mimic the complex structure and function of the GFB. Even though some success in generating kidney structures has been described using conventional 2D or 3D culture systems (including spheroids and extracellular based gels (5)), the results are still inconsistent. The recent discovery of kidney organoids allows the formation of nephron-like structures that recapitulate some of the characteristics of the glomerular environment (6), but they have no or limited filtration activity and the deposition of a correct GBM has not been demonstrated yet. Most importantly, the cells used to generate these organoids are derived from genetically modified cell lines and using complex nephrogenic induction protocols, which may affect their morphology and function (7).

Recently, the development of microfluidic platforms (organ on a chip) that allow co-culture of cells and matrices, combined with the application of perfusion and spatial control over signaling gradients (8), have been used for physiological studies and drug discovery for many complex organs including liver, heart, gut, lung and brain (9-15). The chip technology has been used to replicate renal structures, including proximal tubules (16-19) and, in few instances, the glomerular compartment (20-22). However, in the majority of the current "glomerular chips," podocytes and glomerular endothelial cells are separated by a synthetic membrane usually constituted by polydimethylsiloxane (PDMS) (8,23-24). While these membranes are equipped with openings (pores) that allow free exchange of media and growth factors, they do not allow the proper crosstalk between glomerular cells that is key for GFB function.

Herein, described for the first time, is a Glomerulus on A Chip (referred to as GOAC) constituted by human podocytes and human glomerular endothelial cells seeded on Organoplates™ (MIMETAS). The system is characterized by the absence of an artificial membrane separating the two monolayers. Cells can be cultured in these chips for >45 days, maintaining their phenotype, and glomerular cells can properly interact to generate a layer of extracellular matrix composed by collagen IV trimer and laminin, the major constituents of the GBM in vivo. Such GFB-like structure recapitulates function of the GFB, including selective permeability and response to nephrotoxic compounds. Specific functionality of these chips was validated using serum from individuals affected by different glomerular diseases and evaluated drug-response.

Response of GOAC to glucose-induced damage was assessed and performance studies of disease modeling was conducted by generating GOAC using amniotic fluid kidney progenitor-derived podocytes (hAKPC-P, (25)) from subjects affected by Alport Syndrome (AS), a hereditary CKD characterized by mutations in COL4 genes (26). Chips generated using these AS-podocytes present impaired permselectivity to albumin, due to a dysfunctional assembly of the GBM, typical of AS.

The system, device, methods and compositions herein provide for a novel invention. These include: 1) the number of each cell (podocytes and endothelial cells) seeded on channel C on the chip generally ranges between about 20-25 k. Smaller or greater amounts result either on incomplete formation of the barrier or clogging of the channel; 2) seeding of podocytes within the collagen I in Channel E (instead of channel C) does not allow the formation of a functional barrier; 3) use of specific cells is needed for the correct generation of the chip (fibroblasts instead of podocytes or human lung endothelial cells instead of human glomerular endothelial cells are unable to build a functional barrier); 4) using the same culture media to fill channel C and channel F does not allow the proper formation of a barrier (use of podocyte media in channel F and endothelial media in channel C allows the formation of the barrier and its long term maintenance; and 5) use of FITC albumin at concentrations usually found in literature (5-10 mg/ml) does not allow to discriminate between healthy and injured channels. (instead use of physiological concentrations of FITC albumin (40 mg/ml) allows to discriminate between healthy and injured chips.)

The glomerular filtration barrier is formed by podocytes, endothelial cells, and a thin layer of basement membrane and is responsible for filtering the blood while preventing the loss of proteins. Provided herein is a glomerular filtration barrier using human podocytes and glomerular endothelial cells seeded into microfluidic chips. In long-term cultures, cells seeded on the chip maintain their morphology, form capillary like structures and express slits diaphragm proteins, for filtration to occur. This system recapitulates the functions and structure of the in vivo glomerulus, including permselectivity. When exposed to sera from patients with anti-podocyte autoantibodies, the chip shows albumin leakage to an extent proportional to in vivo proteinuria, phenomenon not observed with sera from either healthy controls or individuals with primary podocyte defects. Not only does the invention described herein have clinical applications, but it also has applications for renal disease modeling and drug testing. This system offers a novel platform to study the patho-physiology of the glomerulus, to identify therapeutic targets, and for high-throughput screening of therapeutic compounds.

There is a need for alternatives to animal studies for development of novel pharmaceuticals and other aspects of disease models. Accordingly, provided herein are different human glomerulus "Organ-on-a-Chip" systems containing living mammalian (e.g., human) cells cultured within microfluidic devices that recapitulates the in vitro pathophysiology of human glomerular filtration barrier/functioning kidney. This integrated microphysiological system can shorten the drug development timeline, save animal lives, reduce failure rates, inform regulatory decision-making, and accelerate development of new therapeutics in the face of emerging infectious diseases or disorders, as well as chemical or biological attack.

Definitions

For the purposes of clarity and a concise description, features can be described herein as part of the same or separate embodiments; however, it will be appreciated that the scope of the invention may include embodiments having combinations of all or some of the features described.

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the term "about" means plus or minus 10% of the indicated value. For example, about 100 means from 90 to 110.

As used herein, the term "Organ Chip" refers to a microfluidic device with at least one physiological function of at least one mammalian (e.g., human) organ (e.g., kidney). While the Organ Chips are discussed herein as mimicking a physiological function of a mammalian kidney, it is to be understood that Organ Chips can be designed that can mimic the functionality of any living organ from humans or other organisms (e.g., animals, insects, plants). Thus, as used herein, the term Organ Chip in not limited to just those that mimic a mammalian organ but includes Organ Chips which can mimic the functionality of any living organ from any organism including mammals, non-mammals, insects, and plants. As such, the systems, devices, and instruments described herein can be used to model or study mammalian as well as non-mammalian (e.g., insects, plants, etc.) organs and physiological systems and effect of active agents on such organs and physiological systems.

Organ Chips are also referred to as Organ Mimic Devices in the art. Generally, the Organ Chips comprise a substrate and at least one (e.g., one, two, three, four, six, seven, eight, nine, ten, or more) microfluidic channels disposed therein. The number and dimension of channels in an Organ Chip can vary depending on the design, dimension and/or function of the Organ Chip. In some embodiments, an Organ Chip can comprise at least one (e.g., one, two, three, four, six, seven, eight, nine, ten, or more) microfluidic channels for the purpose of seeding/growing cells and/or replenishing nutrients to the biological material contained within the Organ Chip.

Organ chips are commercially available, see for example those chips available from Mimetas (Leiden, The Netherlands). For example, the OrganoPlate® is a microfluidic 3D cell culture plate, supporting up to 96 tissue models on a single plate. Phaseguides™ enable precise, barrier-free definition of culture matrices and cells in 3D, supporting cell-cell interactions and unprecedented imaging and quantification. Continuous perfusion of media through the microfluidic networks in the OrganoPlate® mimics blood flow and enables exchange of nutrients, oxygen and metabolites. Our unique gravity-driven leveling technology maintains flow without the use of pumps and tubing, making the OrganoPlate® suitable for any throughput. The addition of culture lanes to the microchambers increases the complexity of the tissue models in the OrganoPlate®. Patterning additional cell types adjacent to the cell layers allows culturing of complex, non-homogeneous tissues. Application of chemical gradients or exposure to gases is supported. This flexibility is particularly useful for stem cell differentiation and cell motility studies.

In some embodiments, an Organ Chip can comprise a plurality of channels (e.g., at least two, at least three, at least four, at least five, at least six, at least seven, at least eight, at least nine, at least ten or more channels). One of skill in the art will readily be able to design and determine optimum number and/or dimension of channels required to achieve a certain application. For example, if assessment of reproducibility and/or comparison of at least two experimental conditions are desirable, an Organ Chip can be constructed to comprise at least two, at least three, at least four, at least five identical channels. This can provide for a number of read-outs per Chip, e.g., allowing assessment of reproducibility and/or for validation and implementation of the technology. For example, each channel can run a different condition (e.g., culturing normal (healthy) cells vs. diseased cells in different channels, or applying different dosages of the same drug to different channels, or applying different drugs at the same dosage to different channels). In some embodiments, an Organ Chip can comprise at least two parallel (e.g., 2, 3, 4, 5, 6, 7, 8, 9, 10, or more) channels. In one embodiment, an Organ Chip comprises three of four parallel channels, e.g., four identical parallel channels. Without wishing to be bound by theory, this configuration can provide quadruplicate read-outs per Chip.

Exemplary Organ Chips amenable to the present disclosure are described, for example, in U.S. Provisional Application No. 61/470,987, filed Apr. 1, 2011; No. 61/492,609, filed Jun. 2, 2011; No. 61/447,540, filed Feb. 28, 2011; No. 6/449,925, filed Mar. 7, 2011; and No. 61/569,029, filed on Dec. 9, 2011, in U.S. patent application Ser. No. 13/054,095, filed Jul. 16, 2008, and in International Application No. PCT/US2009/050830, filed Jul. 16, 2009 and PCT/US2010/021195, filed Jan. 15, 2010, content of all of which is incorporated herein by reference in their entirety. Muscle Organ Chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and PCT patent application titled "Muscle Chips and Methods of Use Thereof," filed on Dec. 10, 2012 and which claims priority to the U.S. provisional application Nos. 61/569,028, filed on Dec. 9, 2011, U.S. Provisional Patent Application Ser. No. 61/697,121, the entire contents of all of which are incorporated herein by reference.

Without limitations, the Organ Chips can have any desired shape.

In some embodiments, outflow of a channel on an Organ Chip can be routed into another. Without wishing to be bound by a theory, this allows mimicking the interconnection of various Organs. For example, outflow of one Organ Chip's Interstitial Channel can be routed into another. This allows mimicking the interconnection of various Organs. In some embodiments, outflow of one Organ Chip's Microvascular Channel can be routed into a Microvascular Channel of another Organ Chip. This allows mimicking the vascular interconnection of various Organs.

As used herein, the terms "including", "includes", "having", "has", "with", or variants thereof, are intended to be inclusive similar to the term "comprising."

As used herein, said "contain", "have" or "including" include "comprising", "mainly consist of", "basically consist of" and "formed of"; "primarily consist of", "generally consist of" and "comprising of" belong to generic concept of "have" "include" or "contain."

EXAMPLES

The following examples are provided in order to demonstrate and further illustrate certain embodiments and aspects of the present invention and are not to be construed as limiting the scope thereof. Example I
Introduction Over 10% of adults worldwide are affected by renal abnormalities and the number of those with end-stage renal disease (ESRD) receiving replacement therapy with dialysis or transplant is estimated at >1.4 million, with an annual growth rate of 8% (1). Major progresses in understanding environmental and genetic risk factors as well as pathogenic mechanisms of renal disease progression have been accomplished, but outcomes of affected individuals have not appreciably improved over the last two decades (1).

Despite a wide variety of causes including metabolic abnormalities, hypertension, autoimmunity, and genetic background, a common early pathologic hallmark of chronic kidney disease (CKD) is decreased glomerular filtration and loss of functional glomeruli (2). The main function of the glomeruli is to filter fluids and electrolytes from the blood, while retaining plasma proteins (3). This activity happens at the level of the glomerular filtration barrier (GFB) and is coordinated by the interaction of two highly specialized glomerular cells (the fenestrated endothelium and the podocytes), which are separated by a thin layer of glomerular basement membrane (GBM (4)).

One of the major roadblocks to the development of successful therapeutics for CKD depends on the ability to effectively establish 3D models that can mimic the complex structure and function of the GFB. Even though some success in generating kidney structures has been described using conventional 2D or 3D culture systems (including spheroids and extracellular based gels (5)), the results are still inconsistent. The recent discovery of kidney organoids allows the formation of nephron-like structures that recapitulate some of the characteristics of the glomerular environment (6), but they have no or limited filtration activity and the deposition of a correct GBM has not been fully demonstrated yet. Most importantly, the cells used to generate these organoids are derived from genetically modified cell lines and require complex nephrogenic induction protocols, which may affect their morphology and function (7).

Recently, the development of microfluidic platforms (organ on a chip) that allow co-culture of cells and matrices, combined with the application of perfusion and spatial control over signaling gradients (8), have been used for physiological studies and drug discovery for many complex organs including liver, heart, gut, lung, and brain (9-15). The chip technology has been used to replicate renal structures, including proximal tubules (16-19) and, in few instances, the glomerular compartment (20-22). However, in the majority of the current glomerular chips, podocytes and glomerular endothelial cells are separated by a synthetic membrane usually constituted by polydimethylsiloxane (8,23,24). While these membranes are equipped with openings (pores) that allow free exchange of media and growth factors, they do not allow the proper crosstalk between glomerular cells that is key for GFB function.

Herein, a glomerulus-on-a-chip (referred to herein as GOAC) constituted by human podocytes and human glomerular endothelial cells (hGEC) seeded on Organoplates™ (MIMETAS) is described. Herein, hAKPC-P have been used along with human glomerular endothelial cells. Primary podocytes and immortalized podocytes have been used as controls. The system is characterized by the absence of an artificial membrane separating the two monolayers (these cells are cultured in a chip devoid of membranes allowing the cells to freely cross-communicate, thus resembling the in vivo glomerular structure; in the GOAC, the podocytes and glomerular endothelial cells maintain their phenotype and are also capable of secreting glomerular membrane with deposition of correctly assembled collagen IV and laminin). Cells can be cultured in these chips for long term, maintaining their phenotype, and glomerular cells can properly interact to generate layer of extracellular matrix composed by collagen IV trimer and laminin, the major constituents of the GBM in vivo. Such GFB-like structure recapitulates function of the GFB, including selective permeability and response to nephrotoxic compounds. Scanning microscopy confirms the glomerular structure with podocytes layered on top of the membrane and forming slit diaphragm and endothelial cells with fenestration, typical of the in vivo glomerulus. Specific functionality of these chips was validated using serum from individuals affected by different glomerular diseases, including membranous nephropathy (MN) and evaluated drug response. GOAC is functional and present permselectivity properties when serum of patients affected by different kidney diseases is used in culture. Response of GOAC to glucose-induced damage and performed studies of disease modeling by generating GOAC using amniotic fluid kidney progenitor-derived podocytes (hAKPC-P (25)) from subjects affected by Alport syndrome (AS), a hereditary CKD characterized by mutations in the alpha chains of COL4 genes (26). Chips generated using these AS podocytes present impaired permselectivity to albumin, due to a dysfunctional assembly of the GBM, typical of AS. GOAC also can be used for drug testing, as well as for disease modeling and signaling pathway analysis. This system allows high throughput analysis of results and is compatible with any imaging systems, including those that work with 96-well plates.

Materials and Methods
Ethics Statement and Acquisition of Human Samples

Amniotic fluid-derived cells: Discarded samples of human amniotic fluid from male fetuses (15-20 weeks of gestation) were provided to our laboratory by Labcorp (now Integrated Genomics, Monrovia, CA, USA) after karyotyping analysis. The study was approved by the Children's Hospital Los Angeles (CHLA) Institutional Review Boards and exemption was obtained since no written or verbal consent was required as samples were de-identified. Samples presented with normal karyotype and ultrasound and were confirmed negative for infectious diseases. Samples of amniotic fluid from patients affected by AS were obtained through the Telethon Biobank (Siena, Italy) directed by Dr. Renieri and Alport hAKPC-P were derived as described below.

Primary glomerular cells: Kidneys deemed non-suitable for transplantation were used for isolation of human primary podocytes and glomerular endothelial cells. CHLA Institutional Review Boards approved tissue collection. Discarded kidneys were harvested from infant patients with a non-nephrological cause of death, and thus our isolation of primary podocytes and glomerular endothelial cells rendered functional cell types.

Immortalized podocyte lines: Were donated by Dr. J. Reiser (Rush University Medical Center, Chicago, IL).

Patient serum: De-identified sera from healthy subjects and from individuals with MN (n=6), FSGS (n=3), PKD (n=3), and AS (n=1) were obtained from Drs. Joaquin Manrique (Biobank Navarrabiomed, integrated in the Spanish National Biobanks Network, Complejo Hospitalario de Navarra, Pamplona, Spain) and Andrea Angeletti (S. Orsola-Malpighi Hospital, University of Bologna, Bologna, Italy). Protocols for the collection of these human samples were approved by the Institutional Review Boards of the two Institutions, and informed consent was obtained from all participants.

Cells: Isolation and Culture

Kidney progenitor cells derived from amniotic fluid (hAKPC) were isolated by co-expression of OB-cadherin, CD24, and podocalyxin (25). Sorted hAKPC were expanded and differentiated into podocytes (hAKPCP) by culturing on collagen I (Corning, c #354236)-coated plates in VRADD media: RPMI-1640 (Gibco, c #11875093) supplemented with 5% FBS (Gibco, c #26140079), 1% antibiotic (Gibco, c #15070063), 1.25(OH)2D3 (100 nM, cholecalciferol) (Sigma, c #C9756), all trans retinoic acid (ATRA) (1 µM), dexamethasone (100 nM) (Sigma, c #D4902), for up to 30 days. Human immortalized podocytes (hiPOD) were cultured as described by Saleem et al. (28). Re-differentiation of hiPOD was performed by thermoshifting to 37° for up to 15 days.

Human lung fibroblasts (hFIB) were purchased from LifeLine Cell Technology (#FC-0049) and expanded with Fibrolife Media (LifeLine Cell Technology, c #LL-0001) in tissue culture dishes for up to five passages. Human lung endothelial cells were purchased from ATCC (HuLEC-5a, CRL-3244) and expanded with ATCC basal media (#MCDB131, supplemented with 10 ng/ml Epidermal Growth Factor, 1 µg/ml hydrocortisone, 10 mM glutamine, FBS to a final concentration of 10%) in gelatin-coated tissue culture dishes for up to five passages.

Primary podocytes (hpPOD) and glomerular endothelial cells (hGEC) were isolated from discarded human kidney samples through mechanical and chemical digestion. Briefly, the kidneys were minced and digested in 125 U/ml collagenase I (Worthington, LS004197) in RPMI-1640 at 37° C. for 30 min and filtered three times in 100-µm cell strainers and once on the 40-µm cell strainer (Corning, c #352360, 352340). The glomeruli that remained on the 40-µm cell strainer were washed out with PBS and centrifuged at 1800×g for 7 min. The extracted glomeruli were thoroughly checked by light microscopy to confirm the absence of contaminants including afferent and efferent vessels and tubules. The glomerular pellet was re-suspended and plated onto a 100 $cm^2$ tissue culture dish in media comprised of RPMI-1640, 5% FBS, and 0.2% Primocin (Invivogen, c #ant-pm-1), and left to incubate overnight at 37° C. After 24 h the glomeruli were trypsinized (Trypsin-EDTA; Gibco, c #25200072) using 0.25% trypsin-EDTA for 5 min to allow all the components of the glomerulus, including the hpPOD and hGEC, to separate. Cells were prepared for sorting as described under FACS and flow cytometry analysis in Methods. Once sorted, the NPHS1-FITC-positive cells (podocytes) were seeded onto collagen in VRADD medium (as described above) and cultured for no more than one passage; the CD31-647 cells (hGEC) were plated onto gelatin (Cell Biologics, c #6950) in human endothelial cell medium (Cell Biologics, c #H1168;) and cultured for no more than 10 passages.

FACS and Flow Cytometry Analysis

Kidney progenitor cells were isolated from human total amniotic fluid cell populations by triple staining with antibodies detecting OB-cadherin-FITC, CD24-APC and podocalyxin-PE. hpPOD and hGEC were isolated from human glomerular cell suspension by staining with respectively NPHS1-FITC and CD31-AF647 antibodies. Briefly, cells were blocked using 1× human IgG (Sigma c #I2511) for 30 min and then stained with the specified antibodies, 1 µg/1× $10^6$ cells/100 µl IgG solution unless otherwise specified on the datasheet, for 1 h on ice. Cells were then washed twice in PBS and filtered immediately before sorting. Cells were sorted using a FACSAria sorter. Unstained and single positive controls were used to perform area scaling, exclude autofluorescence, and perform fluorochrome compensation when needed. Cells were first gated based on forward and side scatters (FSC/SSC) to exclude dead cells and then gated for FSC-W/FSC-H and SSC-W/SSC-H to exclude potential duplets. Sorting gates were established based on the unstained population for each sample. For flow cytometry analysis, cells were fixed in 4% paraformaldehyde (Santa Cruz Biotechnology c #sc-281692) for 10 min and permeabilized with 0.05% saponin for nuclear proteins (WT1). Cells were then blocked in 1× human IgG solution for 10 min and incubated with either antibody for WT1, nephrin, CD31, EHD3, syndecan-1, and syndecan-4. Analysis was performed on a FACScan to machine using FACSDiva software. Gating strategy was performed as described above. Histogram plots were obtained using FlowJO software.

Microfluidic Chip and Cell Seeding

OrganoPlate™ culture was performed using three-lane chip with 400 µm×220 µm channels (Mimetas BV, the Netherlands). Phaseguide™ had dimensions of 100 µm×55 µm. Gel and perfusion channels have a length of 9 and 13 mm, respectively. In all, 1.67 µl of gel composed of 4 mg/ml Collagen I (AMSbio Cultrex 3D Collagen I Rat Tail, 5 mg/ml, c #3447-020-01), 100 mM HEPES (Life Technologies, c #15630-122), and 3.7 mg/ml $NaHCO_3$ (Sigma, c #S5761) was dispensed in the gel inlet (middle) and incubated 20-30 min at 37° C. hAKPC-P, hiPOD, hpPOD, hGEC, hFIB, and HuLEC were trypsinized using 0.05% trypsin-EDTA (Gibco, c #LS25300062) aliquoted and pelleted (5 min, 1500×g). The cells were applied to the system by seeding 2 µl of 1.5×$10^7$ of cells/ml in the inlet of the top medium channel. Subsequently, the OrganoPlate™ was placed on its side at an angle for 30 min at 37° C. to allow the cells to sediment against the collagen I. This was followed by addition of 50 µl of podocyte differentiation medium to both the inlet and outlet of the top medium channel and the OrganoPlate™ was again incubated on its side overnight at 37° C. to complete cell attachment. The following day, hGEC were applied to the system using the same procedure as described above with addition of endothelial cell medium. This created the polarity of the GFB, with endothelial cells oriented toward the vascular channel represented by the plate, and podocytes oriented toward the urinary channel, which had by then layered on top of the collagen. Media described above was changed every 2-3 days such that endothelial cell medium was added to the top inlet and outlet, and podocyte differentiation medium was added to the bottom inlet and outlet, thereby reaching their respective cell types. The OrganoPlate™ was placed horizontally in the incubator (37° C., 5% $CO_2$) on an interval rocker switching inclination every 10 min, allowing bi-directional flow. Medium (50 µl each on inlet and outlet) was refreshed every 2-3 days.

Assessment of Shear Stress

GOAC platform uses a gravity-based perfusion system with a dynamic flow due to periodic 7° tilting. When the plates are levelled to 0° and both volumes are equal no pressure difference exist between the two wells; however, by periodically tilting the plates, a height difference is imposed between liquid levels in connecting walls which results in a pressure difference that causes associated shear stress. This induced shear stress in the microfluidic channels of the OrganoPlate™ can be estimated using a numerical model proposed and verified by Vormann M. K. et al. (40). Using this numerical model, the induced pressure difference between the two volumes of fluid present in the inlet and outlet wells was calculated. The pressure caused by the gravitational pull on a volume of fluid by P=pgh (p=fluid density, g=gravitational constant, and h=height) was also calculated. The flow rate was calculated by $Q=\Delta P Rh^{-1}$ ($\Delta P$=pressure difference and Rh=resistance). The resistance was calculated by $Rh=12\ uL(wh^3\ (1-0.630\ hw^1))^{-1}$ (w=width, u=fluid viscosity (0.001 $kgm^{-1}\ s^{-1}$)), L=channel length. Finally, the shear stress τ (Pa) was calculated by $\tau=6\ uQ(wh^2)^{-1}$. The final value of induced shear stress is equal to 0.0117 Pa.

Immunofluorescence and Confocal Imaging

Immunofluorescent staining was performed on OrganoPlate™ and chamber slides of representative cell types: following fixation by 4% paraformaldehyde (Santa Cruz Biotechnology c #sc-281692) and serial washes with PBS. Chips/wells of interest were prepared for staining by blocking with 5% bovine serum albumin (Jackson ImmunoResearch Lab, c #001-000-162) in PBS for 30 min. Primary, secondary, and pre-conjugated antibodies were diluted in 2.5% BSA Jackson ImmunoResearch Lab. c #001-000-162) as indicated in Table 1. Thirty microliters of solution were added to the top and bottom inlets and outlets of the chips or 100 µl of solution was added directly into the chamber slide wells. Primary antibodies were incubated at RT for 1 h; following serial washes, secondary antibodies were incubated at RT for 30 min. After a final series of washes in PBS, DAPI was applied (1:1000 in PBS; BD Pharmingen, c #564907) and the OrganoPlate™ or the wells were stored at 4° C. until imaged by confocal microscopy (Zeiss 710 microscope) and processed using the ZEN10 software.

TABLE 1

List of antibodies and assay-specific concentrations

| Antibody | Company | Catalogue # | Dilution |
|---|---|---|---|
| CD24 | R&D | FAB5247A | 1:10 |
| OB-cadherin | R&D | FAB17901G | 1:20 |
| Podocalyxin | R&D | FAB1658P | 1:10 |
| CD31 (AlexaFluor-647) | BD Pharmingen | 561654 | IF 1:50 |
| VEGFR2 | Abcam | 2349 | IF 1.5:100 |
| WGA (Rhodamine) | Vector | RL-1022 | IF 1:100 |
| NPHS1 (FITC) | LifeSpan Biosciences | LS-C370063 | IF 1:100 |
| Nephrin (NPHS1) | Invitrogen | PA5-20330 | WB: 1:1000 |
| WT1 | Abcam | ab15249 | IF 1:50 |
| Col IV α1,2 | Abcam | ab6311 | IF 1:50 |
| Col IV α3 | Shigei Research Institute | H31 | WB: 1:100 |
| Col IV α4 | Shingei Medical Research | RH42 | IF: 1:25 |
| LAM α5 | Abbiotec | 251457 | IF 1:100 WB 1:500 |
| $PLA_2R$ | Millipore Sigma | MABC942 | IF 1:25 |
| $PLA_2R$ | LifeSpan Biosciences | LS-C153547 | WB: 1:500 |
| IgG4 | LifeSpan Biosciences | LS-C351418-500 | IF: 1:20 |
| IgG (FITC) | Abcam | ab97174 | IF 1:20 |
| F-actin | Life Technologies | r37122 | 1 drop/ml |
| B-actin | GeneTex | GTX109639 | WB: 1:1000 |
| C3d | Abcam | ab17453 | WB: 1:1000 |
| Heparan Sulfate | Abcam | ab23418 | IF: 1:75 |
| Syndecan 4 | ThermoFisher | 36-3100 | IF: 1:75 FC: 1:100 |
| Syndecan 1 | Abcam | Ab34164 | IF: 1:75 FC: 1:100 |
| EHD3 | Atlas Antibodies | HPA049986 | IF: 1:100 |
| EHD3 | ThermoFisher | PA5-25963 | FC: 1:50 |
| BAX | Santa Cruz Biotechnology | SC-493 | IF: 1:100 |

Scanning Electron Microscopy

Samples were processed by the University of Southern-California Keck School of Medicine microscopy core. Samples were fixed in half-strength Karnovsky's fixative, post-fixed in 2% $OsO_4$, followed by ethanol dehydration and hexamethyldisilazane drying. Air-dried specimens were mounted on specimen stubs using silver paste and sputter-coated with gold-palladium according to standard procedures. Specimens were visualized by scanning electron microscopy on a JEOL JSM-6390LV instrument (JEOL, MA, USA) operated at 10 kV accelerating voltage.

Albumin Permselectivity Assay and Inulin Permeability Assay

An albumin and inulin permeability assay were established to evaluate the efficiency of the created GFB. The number of chips used for each experiment is described in the corresponding figure legend. Media was aspirated from the bottom inlet and outlet, to which PBS was added. Then, media from the top inlet and outlet was aspirated. Fifty microliters albumin-FITC (Millipore Sigma, c #A9771) or inulin-FITC (10 mg/ml, Sigma, c #F3272) was added to the top inlet and outlet, such that the orientation of filtration would be simulated as in native blood flow: from endothelial cells, through podocytes, and into the urinary space of Bowman's capsule. Presence of FITC, and thus albumin or inulin, in the bottom channel indicated a disruption of the GFB. The chips were imaged at 5 and 60 min, during which the plates continued to incubate at 37° C. At 60 min, media was collected from the bottom inlet and outlet. Absorbance was measured using the Perkin Elmer Victor 3 plate reader using Wallac 1420 workstation software (fluorescein 485/535, 0.1 s). For long-term studies, the same chips were evaluated for permselectivity at respectively 1, 2, 3, and 4 weeks (hAKPC and hpPOD; hiPOD were evaluated for weeks 1 and 2 since after this time frame these chips are not properly functioning) after hGEC seeding. Culture medium was consistently replaced every 3 days. After each reading, as described above, the albumin-FITC solution and PBS were removed from the top and bottom inlets and outlets and chips were carefully rinsed with PBS twice to remove excess albumin-FITC before returning to fresh culture medium. Efficiency of the GOAC was calculated by assigning a value of 0 to null fluorescein absorbance readings and a value of 100 to fluorescein absorbance readings equal or higher than 300,000 (measurement obtained when FITC-albumin in freely diffusing through cell-devoid chips, FIG. 3H—COL1+no cells). Efficiency at each time point is expressed as %±SEM.

Transwell Establishment

Following coating of the transwells (Costar, #3495) with collagen I, hpPOD were seeded in VRADD media. Once a monolayer was formed (48 h), hGEC was added and allowed to attach on top of the podocytes for 7 days. VRADD media was substituted with GEC media, as performed on the GOAC. The transwells were then transferred onto the same rocker used to generate the flow in the GOAC. After 7 days, albumin leakage was tested under the same conditions of the chips (timing, BSA-FITC concentration), filtrate was collected after 1 h, and absorbance measured as described above.

Puromycin Aminonucleoside (PAN) Injury

In all, 10 μg/ml of PAN, a nephrotoxic molecule (Cayman Chemical c #15509), was supplemented to the media for 5 days. Media without PAN was used as a control. The number of chips used for each experiment is described in the corresponding figure legend. After PAN injury, damage was assessed using the albumin assay performed on the chip as described above.

Assessment of IgG Passage Through the Glomerular Endothelial (GEC) Layer

To assess ability of IgG to cross a monolayer of hGEC, 50 μl of gel composed of 4 mg/ml Collagen I (AMSbio Cultrex 3D Collagen I Rat Tail, 5 mg/ml, c #3447-020-01), 100 mM HEPES (Life Technologies, c #15630-122), and 3.7 mg/ml NaHCO3 (Sigma, c #55761) was dispensed on top of 24-well transwells (Corning, c #29442-129) and incubated 20-30 min at 37° C. In total, 100,000 hGEC were seeded for 3 days or until full confluency on the transwells and supplemented with GEC media. In all, 1 mg/ml of human IgG (Sigma c #12511) or mouse IgG (Thermofisher, c #31903) were FITC-labeled using Zenon® labeling technology (Thermofisher, c #Z25402 and Z25002). Fifty microliters of labeled IgG were added onto the top of the transwells and were incubated at 37° C. for up to 24 h. Transwells devoid of cells were used as controls. At 15 min, 30 min, 1 h, 3 h, 6 h, and 24 h media was collected from the bottom of the transwell. Absorbance was measured using the Perkin Elmer Victor 3 plate reader using Wallac 1420 workstation software (fluorescein 485/535, 0.1 s) as described above.

Experiments with Human Sera

The number of chips used for each experiment is described in the corresponding figure legend. FBS-free endothelial cell medium supplemented with 0.5% human serum from diseased and healthy individuals was added to the top inlet and outlet and was incubated for 24 h. After 24 h, the human serum-supplemented media was removed from the chips and the albumin assay was performed as described above. Healthy patient serum was used as a control.

Glucose-Mediated Injury

Glucose-mediated injury was induced by supplementing glomerular endothelial medium with high-glucose (Sigma, c #5146) at 10 mM (standard RPMI-1640 glucose concentration), 15 mM, and 20 mM. High-glucose media was added to the top inlet and outlet for 72 h. After 72 h, the serum-supplemented media was removed from the chips and the albumin assays was performed as described above.

α-Melanocyte-Stimulating Hormone Drug Rescue

α-Melanocyte-stimulating hormone (10 ng/mL; Sigma, c #M4135) was added to 0.5% human patient serum-supplemented endothelial medium to rescue the effect of MN serum on the GFB. The chip was incubated for 24 h. After 24 h, the serum-supplemented media was removed from the chips and the albumin assays was performed as described above.

Western Blot Analysis

Total protein from the OrganoPlate™ was collected by adding 125 U/ml collagenase I (Worthington, LS004197) in a radioimmunoprecipitation assay RIPA lysis buffer (Santa Cruz Biotechnology, c #sc-24948) containing a protease inhibitor cocktail (Thermo Scientific, c #78442) and incubated at 37° C. for 30 min. Protein lysates were centrifuged at 17,000×g, 4° C. for 10 min to obtain the protein suspension. The supernatant was then collected, and total protein concentrated using acetone precipitation. Briefly, four volumes of ice-cold acetone were added to the protein suspension and incubated on ice for 30 min. The solution was centrifuged at 13,500×g, 4° C. for 10 min, the supernatant discarded, and the pellet was air dried for 20 min. The pellet was resuspended in 100-200 μl of RIPA buffer containing protease inhibitors. Protein extracts were separated on 4-20% pre-cast Protean TGX gels (Bio-Rad, c #456-1094) followed by transfer onto 0.2 μm polyvinylidene fluoride (PVDF) membranes (Bio-rad, c #1704156) using the Trans-blot Turbo transfer system (Bio-Rad, c #170-4155). Membranes were soaked in methanol 100% for 10 min, quickly rinsed in 0.1% tween 20 (Sigma-aldrich c #P9416), 1× Tris-buffered saline buffer (TBS-T). Blocking was performed in 5% blotto, non-fat dry milk (Santa Cruz Biotechnology, c #sc2325) in TBS-T buffer for 1 h at RT, followed by primary antibody incubation (in 2.5% milk solution) ON at 4° C. in rocking conditions. Following washes in TBS-T buffer (10 min for three times), membranes were blotted with host-specific horseradish peroxidase (HRP)-conjugated secondary antibodies diluted in 2.5% skim milk (in TBS-T) at RT for 30 min. For Col4A3 chain detection, the same electrophoresis and transfer methods were used. The membranes were then processed by blocking with 3% BSA containing 50 mM Tris-HCl buffer (containing 150 mM NaCl) for 30 min Membranes were washed three times with 0.05% tween 20-Tris buffer and blotted ON at 4° C. with COL4A3 antibody diluted in 1% BSA-containing Tris-HCl buffer. The same solution was used to dilute the HRP-conjugated secondary antibody. Signal was detected by using the SuperSignal West Femto substrate (Thermo Scientific, c #34096) and impressed on Amersham Hyperfilm ECL (GE Healthcare, c #28906835). Densitometry was performed on images using ImageJ software.

Statistics

Statistical analysis was performed using SigmaPlot v11.2. All graphical data are displayed as the mean+SEM. Normality test (Shapiro-Wilk) and equal variance tests were performed. One-way ANOVA was used to compare independent sets of normally distributed data. Holm-Sidak post hoc test was performed unless otherwise indicated. When a normal distribution was not confirmed, Kruskal-Wallis one-way analysis of variance was performed instead. Studies of correlation across sets of samples were performed by polynomial linear regression analysis. For all statistical analysis, a p value less than 0.05 was considered statistically significant.

Results

Characterization of Human Podocytes and hGEC

Figure 1G:
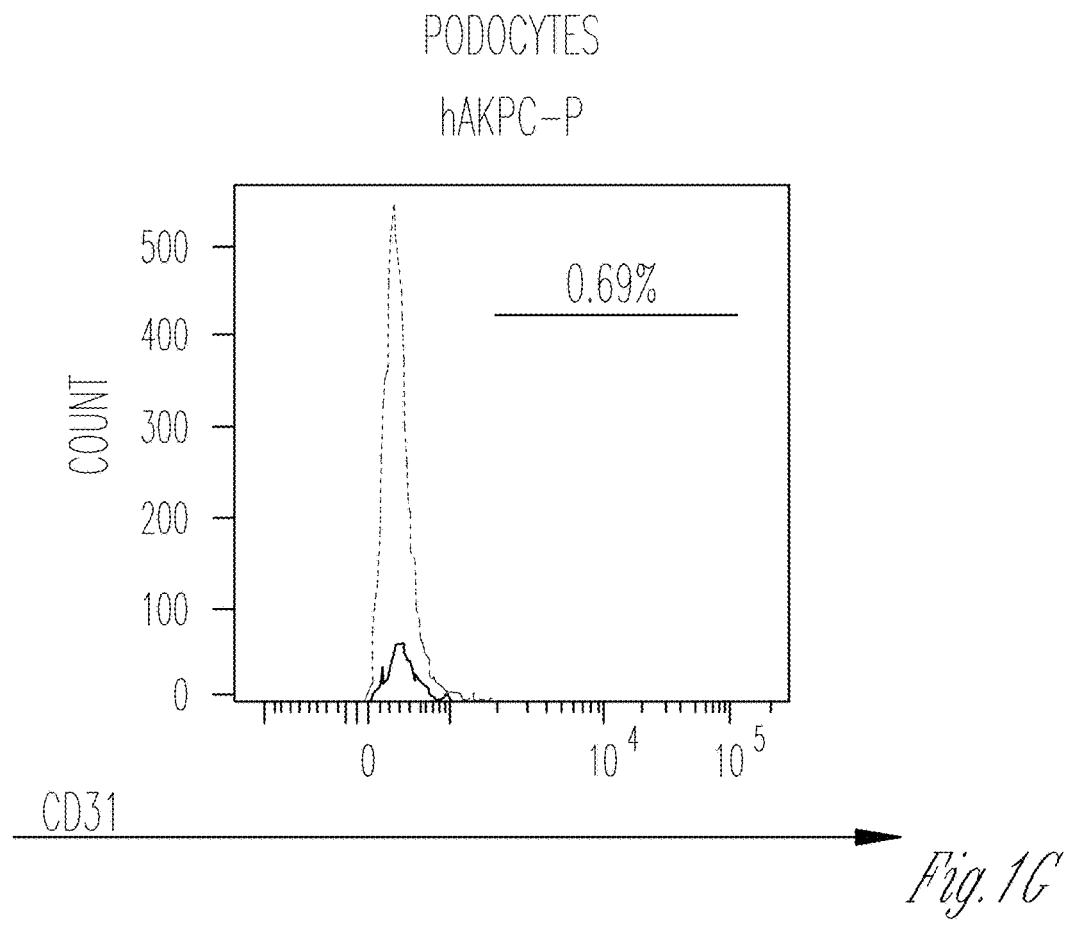
Figure 1H:
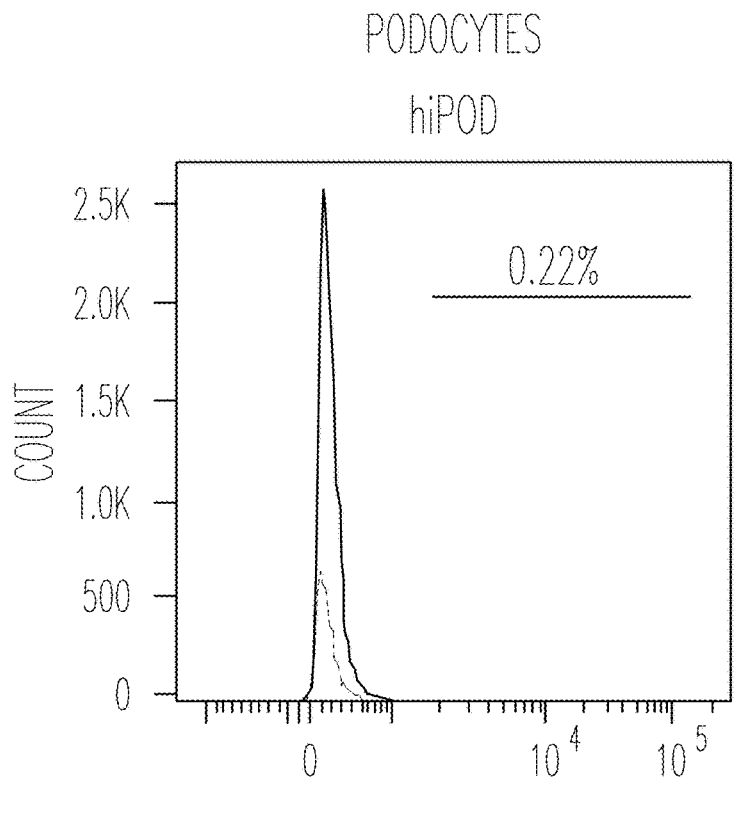
Figure 1I:
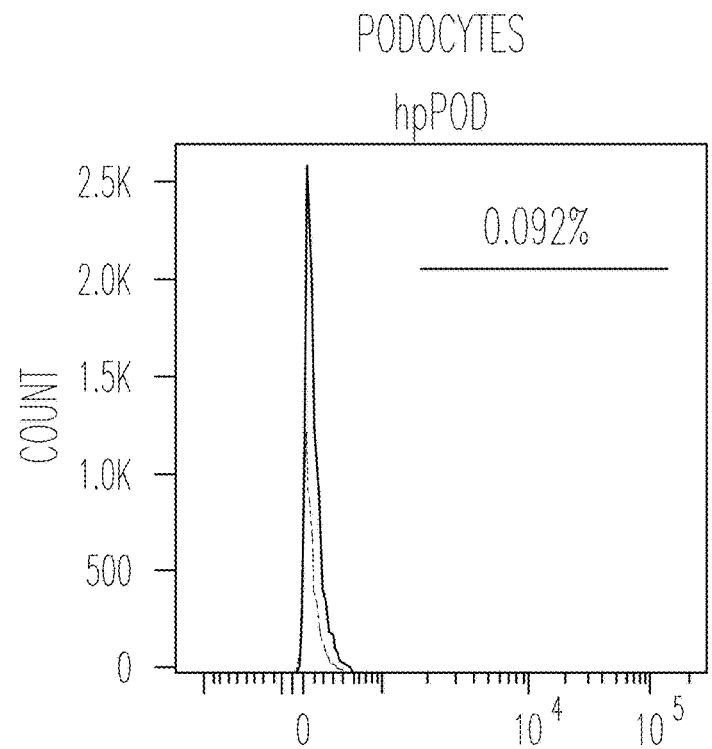

Different types of podocytes of human origin were used: (1) primary podocytes (hpPOD); obtained from discarded kidneys harvested from patients with non-nephrological cause of death, thus the cells were healthy; (2) immortalized podocytes (hiPOD) considered for many years the gold standard for in vitro cultures (27,28); and (3) amniotic fluid-derived podocytes (hAKPC-P): obtained in the laboratory as published (25). hAKPC-P can be derived with minimal cell manipulation and, before differentiation, can be expanded for many passages while maintaining their ability to differentiate into podocytes with high efficiency.

hpPOD were obtained from human glomeruli and positively selected for nephrin and were seeded immediately after isolation or after one passage in culture.

hAKPC-P and hiPOD were differentiated in VRADD media on collagen I prior to seeding on the chip (28). Podocyte morphology is evident in all three lines as well as expression of markers typical of mature podocytes such as WT1 and the slit diaphragm protein nephrin (FIG. 1A-F), while they were negative for CD31 (endothelial marker) (FIG. 1G-I) and wheat germ agglutinin (WGA, identifying the endothelium glycocalyx), overall confirming their podocyte phenotype.

Figure 1J:
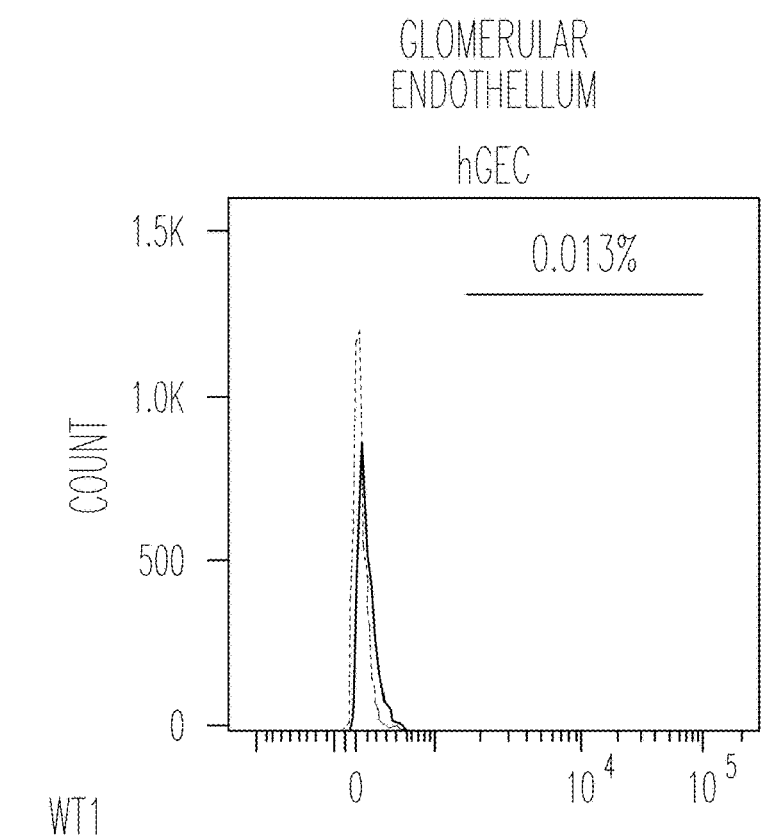
Figure 1M:
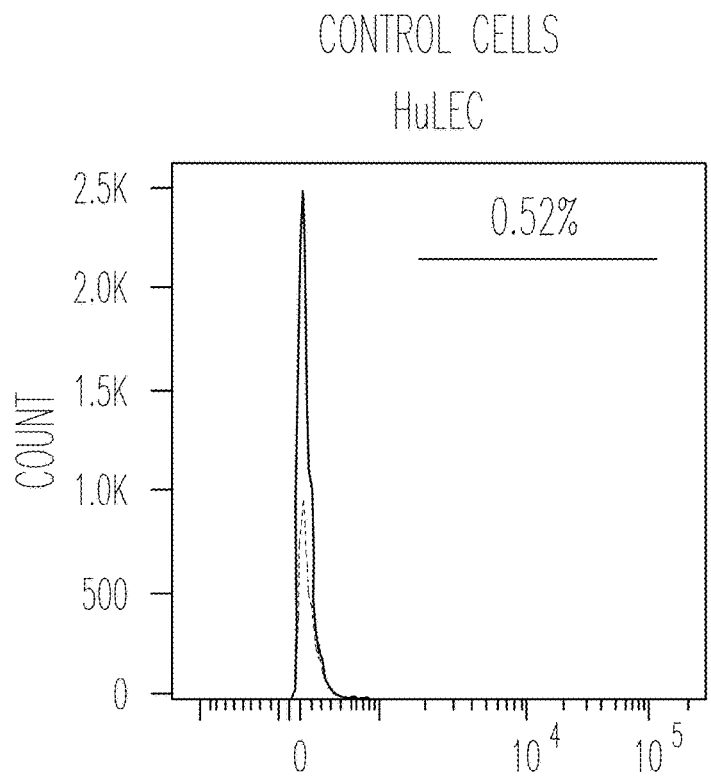
Figure 1N:
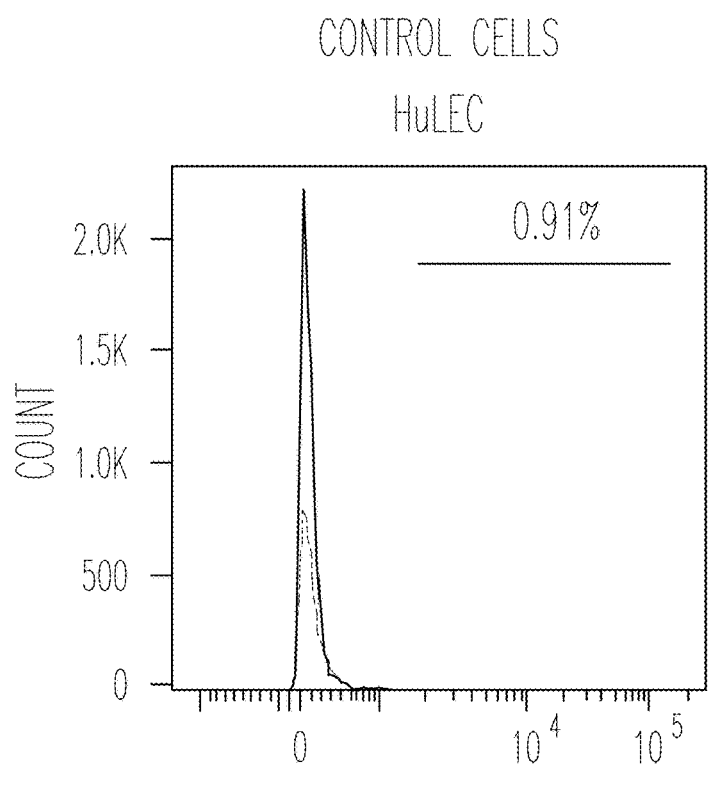
Figure 1O:
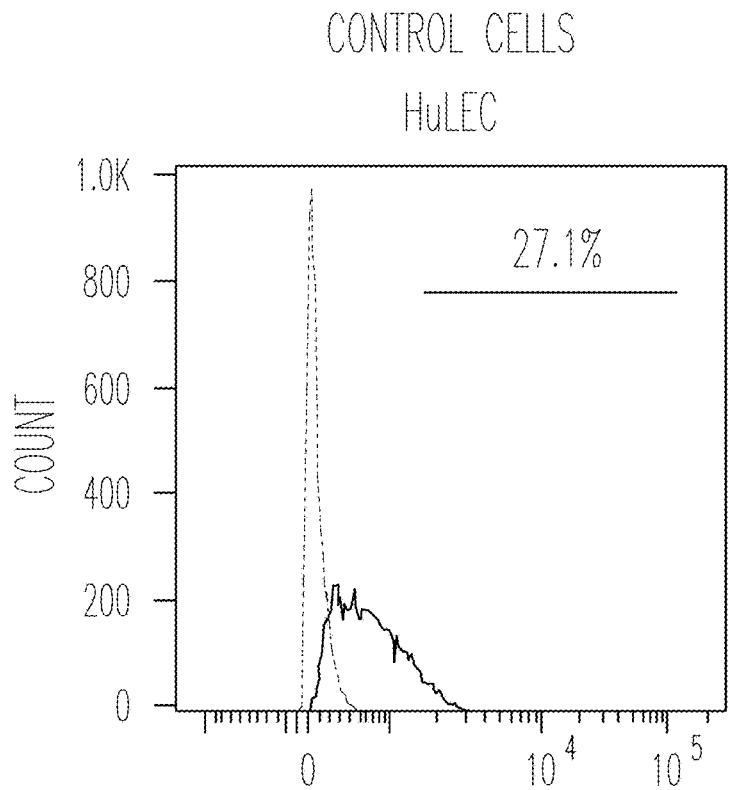
Figure 1P:
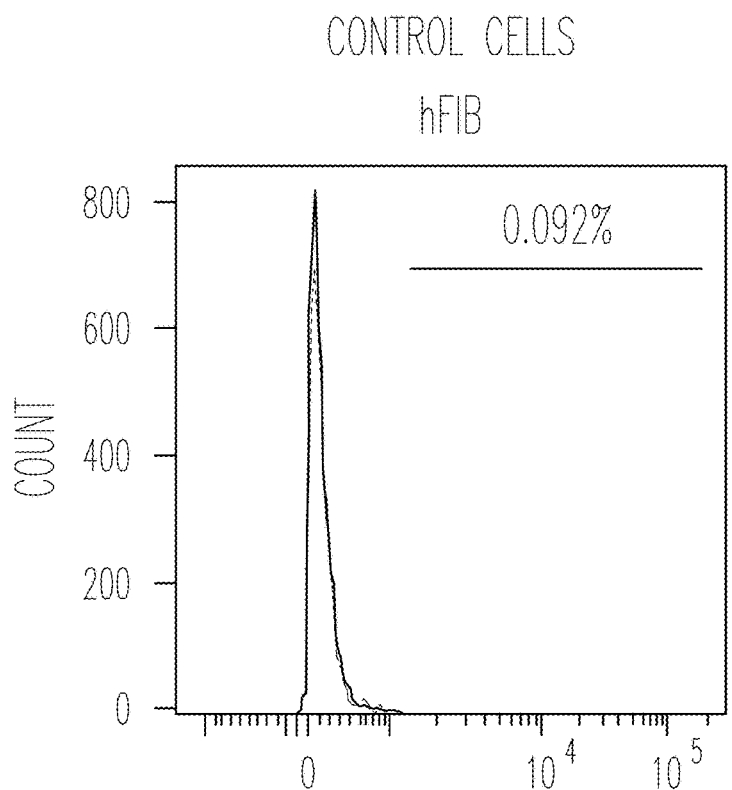
Figure 1Q:
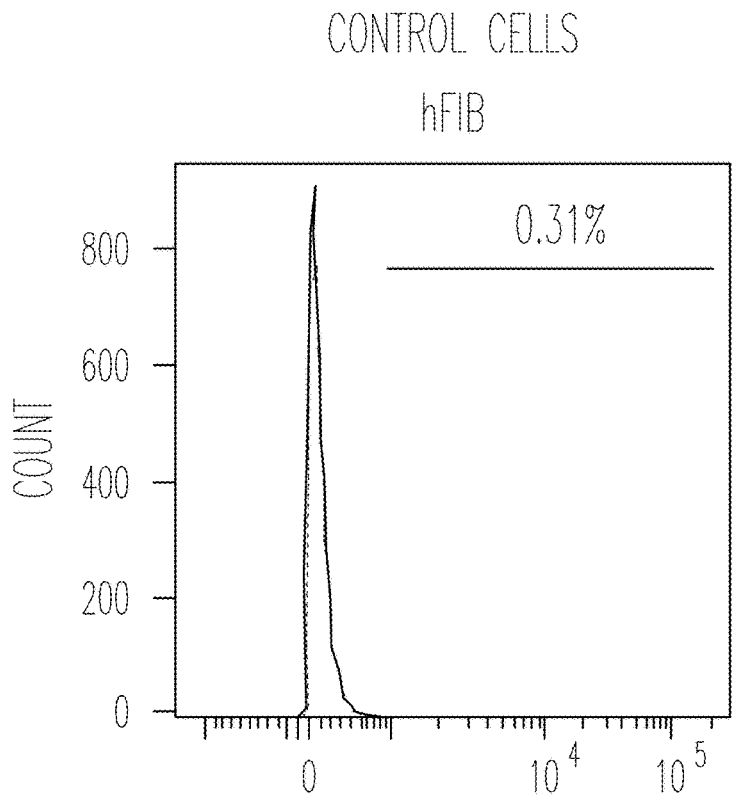
Figure 1R:
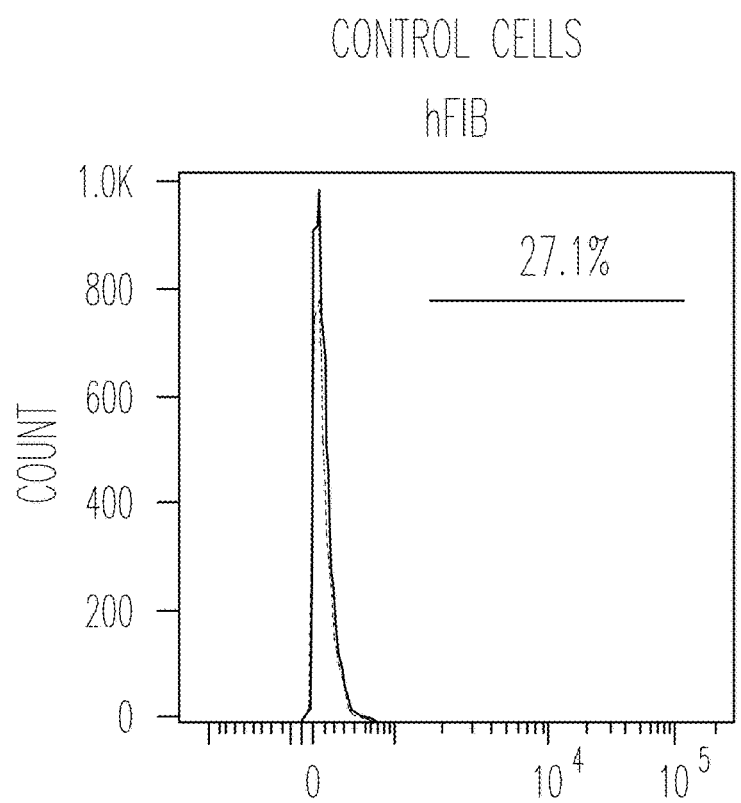

The glomerular endothelium is characterized by unique fenestrations that can be considered analogous of podocyte filtration slits and contributes to the GFB function. Primary hGEC, isolated from the same kidneys from which hpPOD were derived, were negative for podocyte markers (WT1, nephrin) and positive for CD31 and vascular endothelial growth factor receptor 2 (VEGFR2; this receptor is expressed in vivo by GEC since they highly respond to the VEGF gradient signaling from podocytes (4)) and WGA (FIG. 1J-L). hGEC were also found to be positive for EH domain containing 3 (EHD3), a marker specifically expressed by the human glomerular endothelium in the kidney (29). These hGEC are characterized by the presence of fenestrations (with an average diameter of 60.55 nm±3.35 SEM, compatible with measurements performed in previous studies (30,31)). Positive expression for major glycocalyx components like Syndecan-1, Syndecan-4, and heparan sulfate was also assessed (32). As negative controls for podocytes and hGEC, human lines of fibroblasts (hFIB) and human lung endothelial cells (HuLECs), respectively, were used. Both HuLECs and hFIB were negative for WT1 and nephrin (FIG. 1M, N, P, Q); HuLEC were positive for CD31, VEGFR2, and WGA (FIG. 1O) while hFIB were negative for all these markers (FIG. 1R).

Culturing Human Podocytes and hGEC on the Chip

Figure 1S:
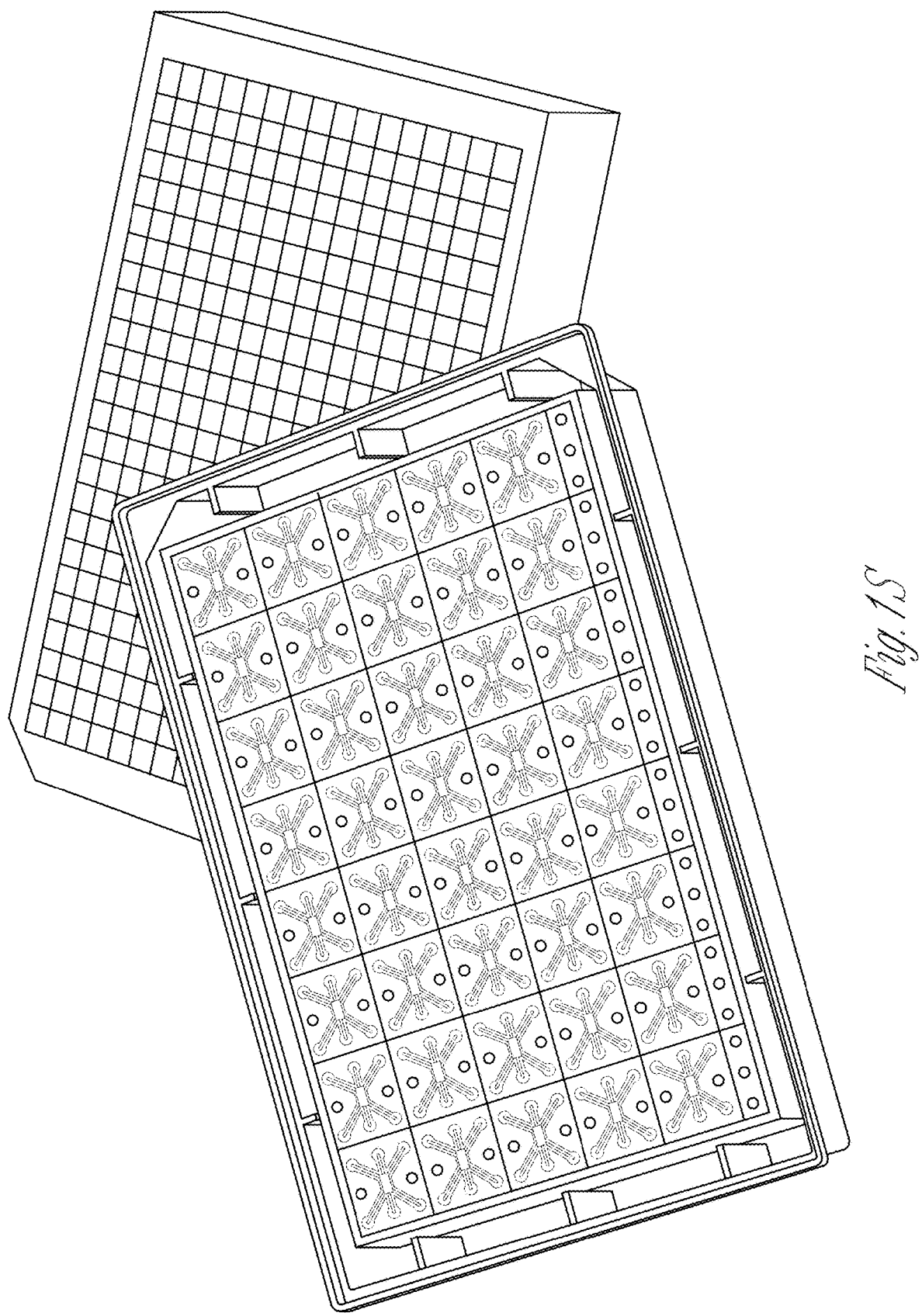
Figure 1T:
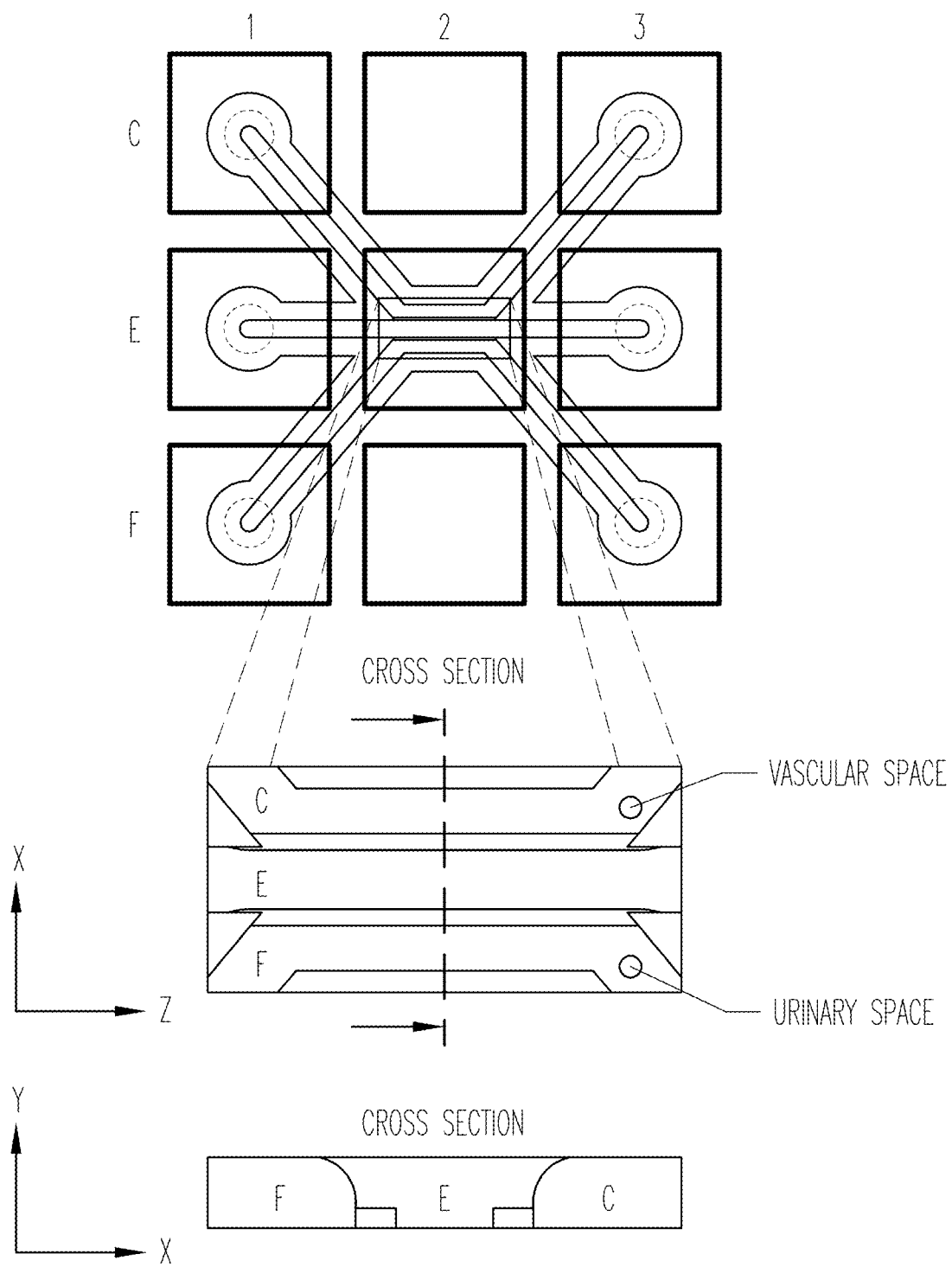
Figure 2A:
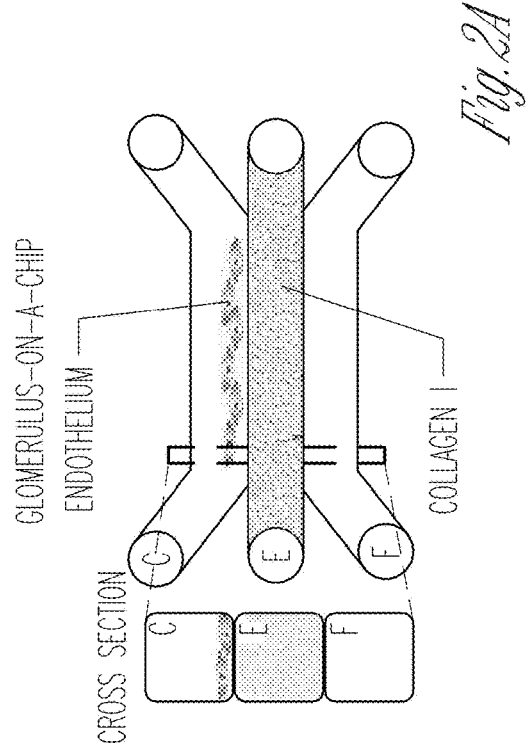
FIGS. 2A-Y. Seeding of endothelial cells and podocytes in Organoplates™ and generation of the GOAC. A Representation of seeded hGEC in Organoplate™. B Confocal Z-stack image showing formation of capillary-like structure. Phaseguide™ components (lines) can be easily identified within the panel. Channel E is filled with collagen I (visible thanks to autofluorescence in the channel) while channel C confirms formation of a capillary-like structure by a continuous monolayer of hGEC (stained with CD31, Alexa-555). C, D confocal image for CD31 (Alexa-555, C) and for WGA (Rhodamine, D) in hGEC after 28 days of culture. E Representation of seeded podocytes in Organoplate™. F-H Confocal image for nephrin (NPHS1-FITC) in hAKPCP (F), in hiPOD (G), and hpPOD (H) seeded on the channel C after 28 days of culture. Nephrin expression is present on the level of cell-cell contact (arrow). I Representation of seeded of podocytes and hGEC in Organoplate™. J-L Confocal image for nephrin (NPHS1-FITC) and CD31 (Alexa-555) in hAKPC-P+hGEC chip (J), in hiPOD+hGEC chip (K), and hpPOD+hGEC chip (L) after 28 days of culture. All three podocyte lines form a continuous layer, distinguishable from the hGEC layer. M Representation of a GBM-like structure in Organoplate™. N-V Confocal image for COL4A4 (Alexa-555), for COL4A12 (Alexa-555), and for LAMA5A (Alexa-555) in hAKPC-P+hGEC chip (N-P), in hiPOD+hGEC chip (Q-S), and hpPOD+hGEC chip (T-V) after 28 days of culture. hAKPC-P+hGEC chip and hpPOD+hGEC chip show de novo generation of GBM, which is less evident in the hiPOD+hGEC. Nuclei are stained with DAPI (blue). All pictures: scale bar=50 µm; except bottom panel in f-l with scale bar=25 µmbar. W-Y Western blot analysis for COL4A3 (25 kDA, monomeric form; 50 kDA, dimeric form), LAMAS (70 kDa), and beta actin (40 kDa) in hAKPC-P+hGEC (W), hiPOD+hGEC (X), and hpPOD+hGEC (Y) GOAC. Positive control: human whole-kidney lysate.
Figure 2B:
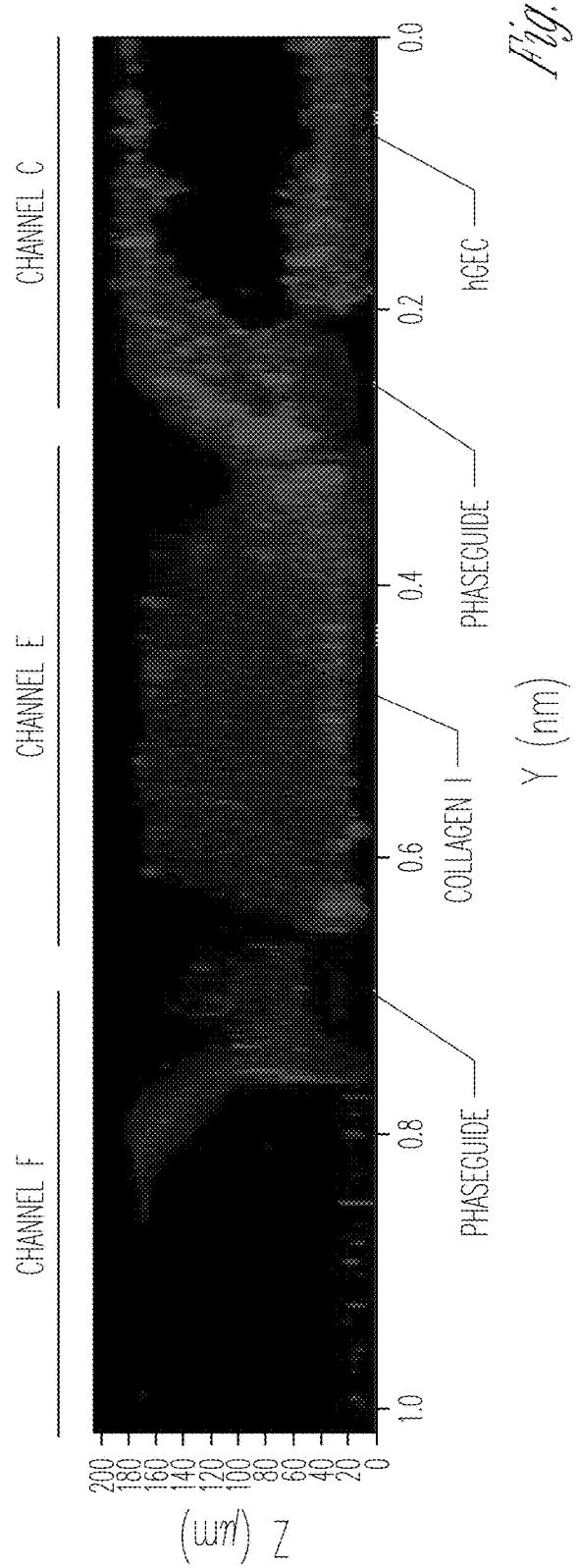
Figure 2C:
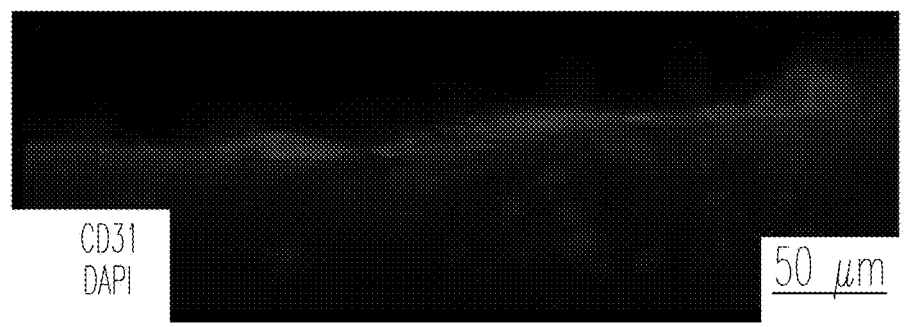
Figure 2D:
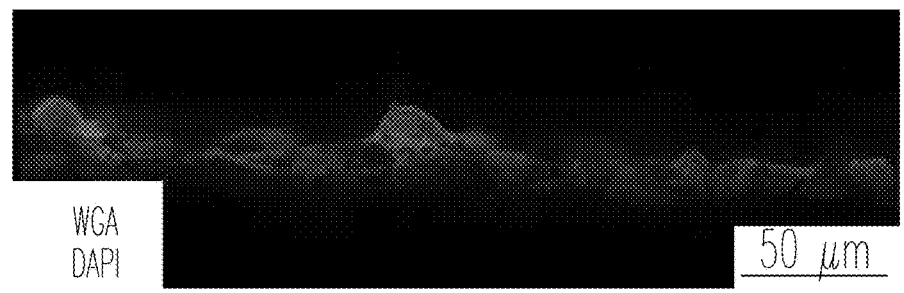
Figure 2E:
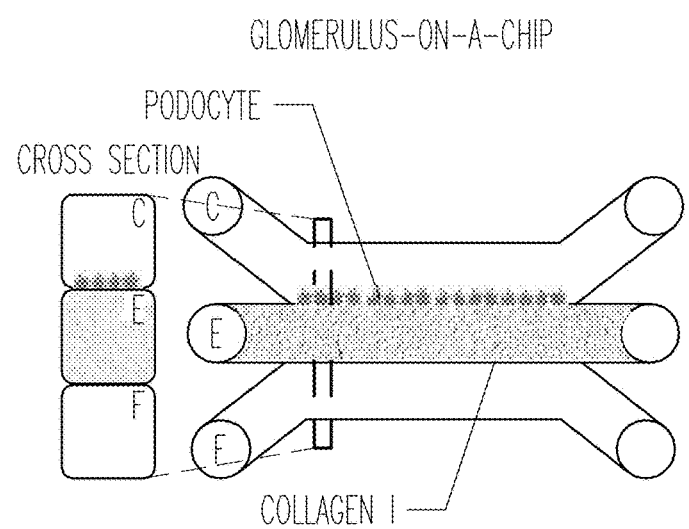
Figure 2F:
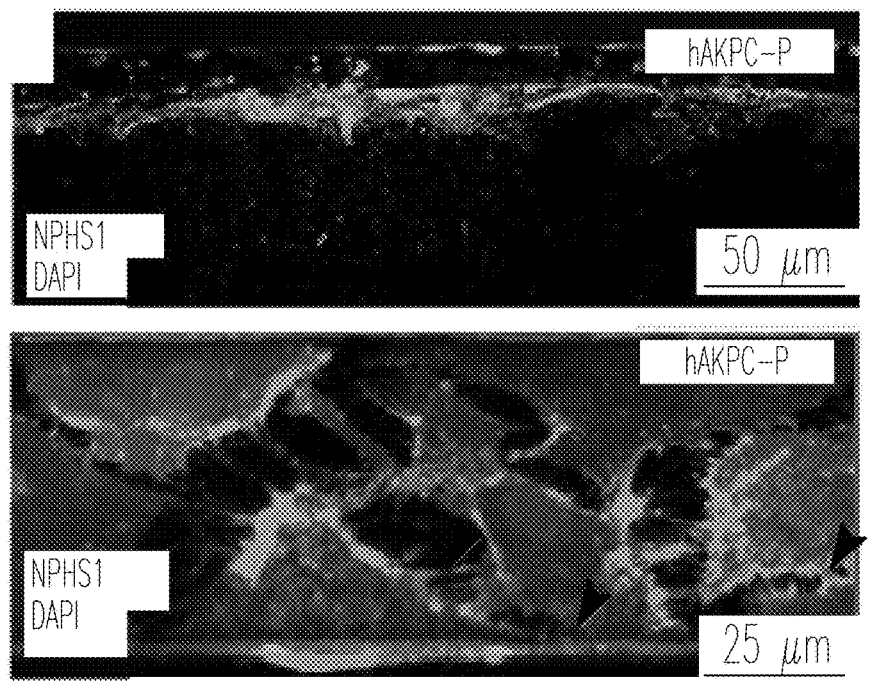
Figure 2G:
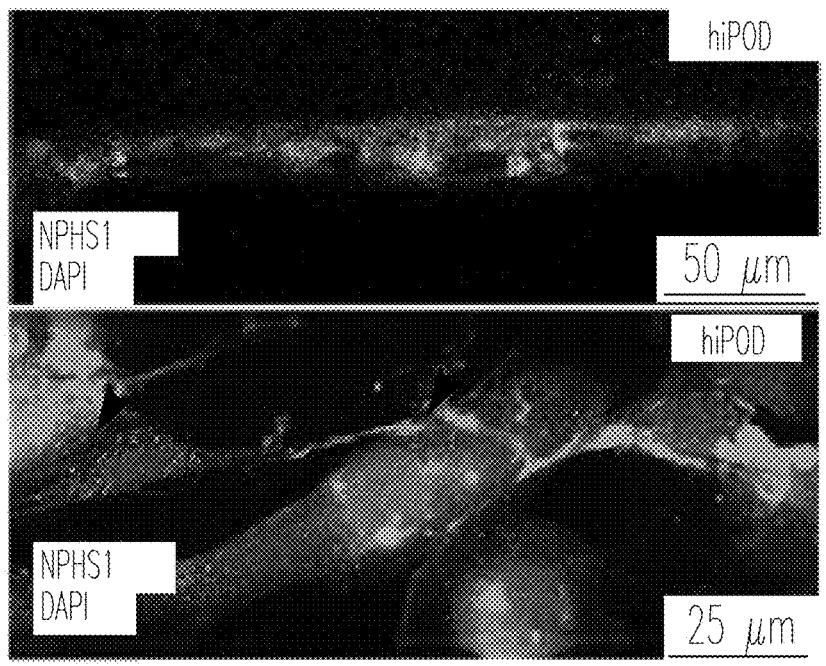
Figure 2H:
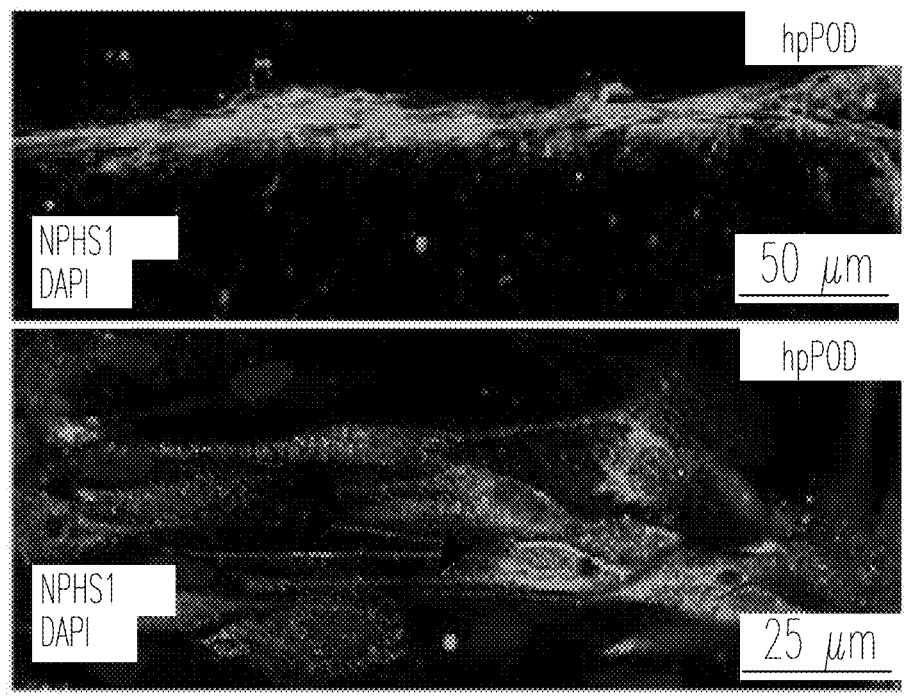

It was first investigated whether the system supports the culture of hGEC and podocytes separately. A schematic representation of the chip and channel seeding is shown in FIG. 1S, T. Since collagen I stratification present in channel E is achieved by meniscus pinning, there is no artificial membrane between the perfusion lane and the collagen. Therefore, the interaction of the layers of seeded cells (channel C) and matrix recapitulates the in vivo GFB oriented from endothelial cells, the GBM, podocytes, and the urinary space of Bowman's capsule (channel F). hGEC were seeded in channel C (FIG. 2A) and cultured in endothelial medium. Their ability to form a capillary-like structure in the chip was confirmed (FIG. 2B) and maintain expression of endothelial marker CD31 (FIG. 2C). Presence of an endothelial glycocalyx on the surface was also confirmed by immunofluorescent staining using WGA (FIG. 2D). Thickness of the glycocalyx was confirmed to be ~0.5 µm, compatible with results previously reported by other groups on human immortalized glomerular endothelial cells (33) and in vivo (32).

hAKPC-P, hiPOD, or hpPOD were seeded in channel C (FIG. 2E) and cultured in VRADD media. Confocal imaging revealed that hAKPC-P, hpPOD, and hiPOD expressed nephrin prevalently in primary processes (FIG. 2F-H, arrows), which appeared less organized in hiPOD (FIG. 2G) compared to hAKPC-P (FIG. 2f) and hpPOD (FIG. 2h). Taken together, these results demonstrate that hGEC and podocytes can be cultured in the chip maintaining their morphology and phenotype.

Structural Characterization of GOAC

Figure 2I:
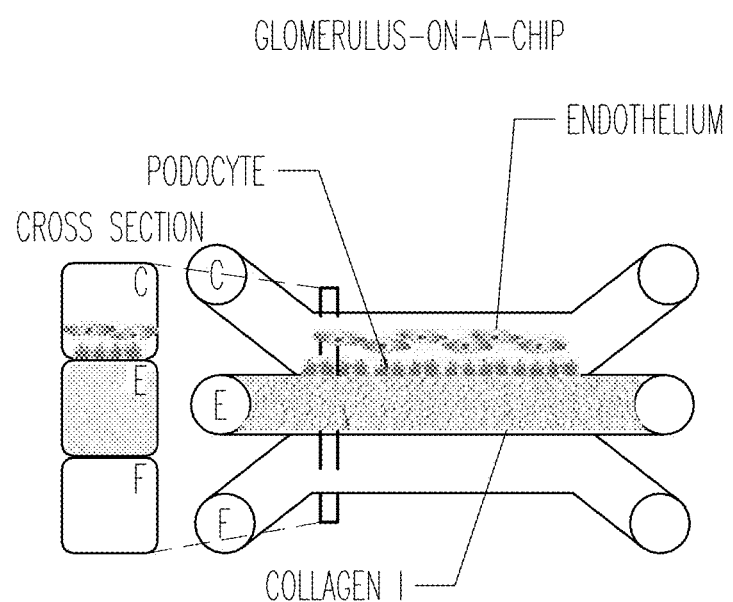
Figure 2J:
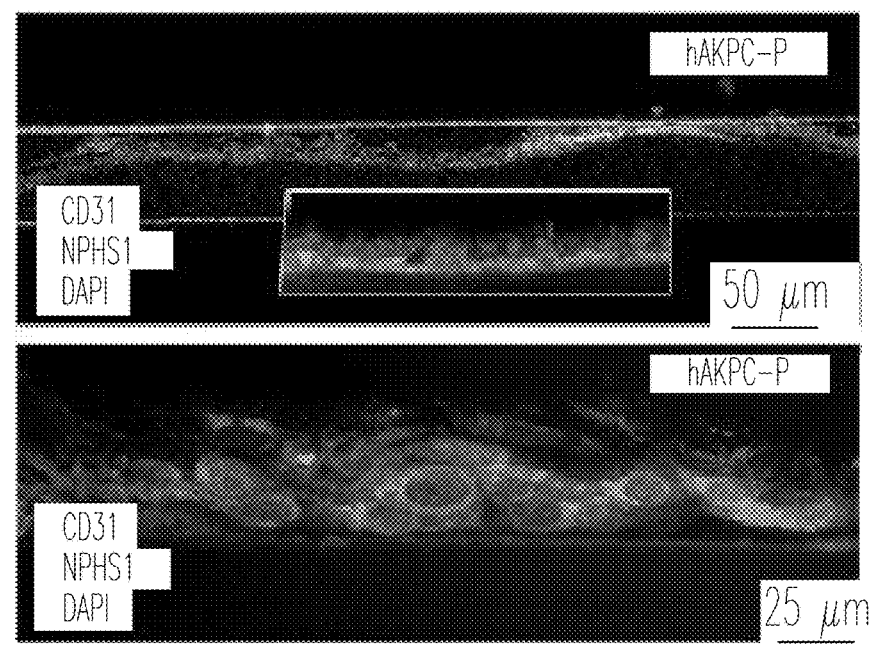
Figure 2K:
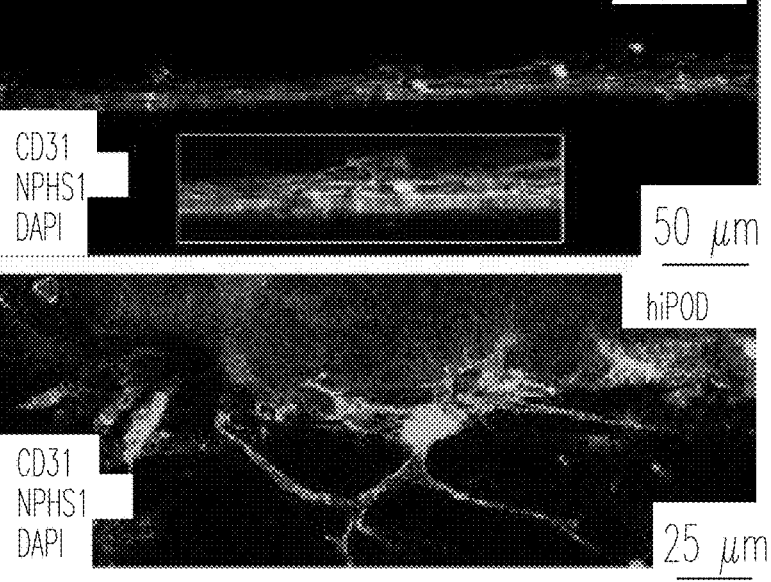
Figure 2L:
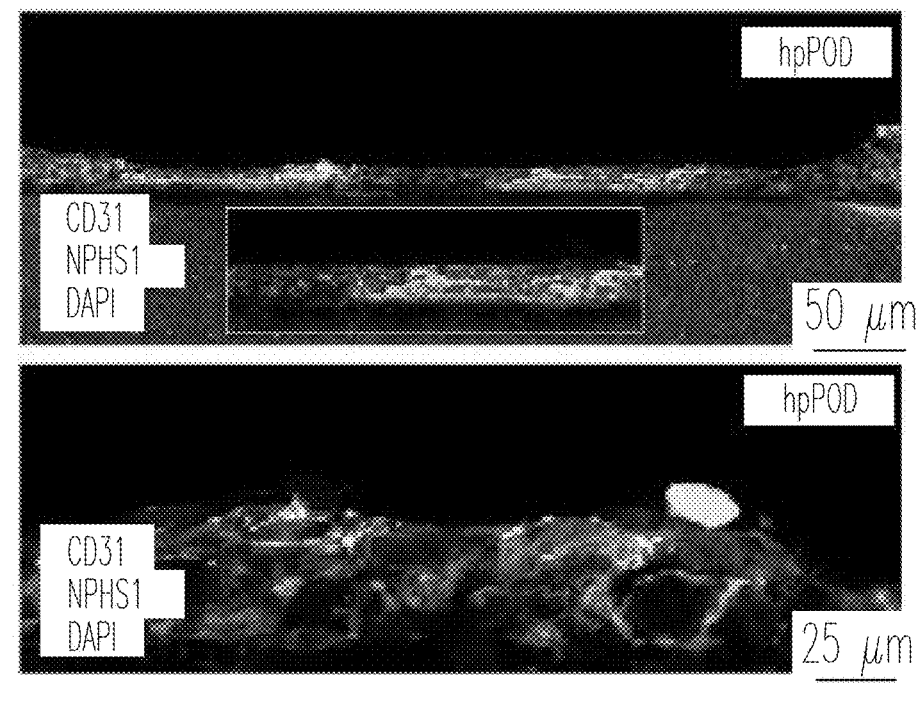

Podocytes and hGEC were co-cultured to generate the GOAC (FIG. 2I). Channel E was first filled with collagen I and, after gelification, podocytes were seeded in channel C. Within 20 min, they started layering on the side of the collagen wall. After 24 h, all cells firmly attached to the wall to form a monolayer to cover the collagen surface. The addition of hGEC was performed on the top inlet in channel C. After 24 h, the chip was placed under flow conditions and hGEC started forming a continuous capillary-like layer that is evident as soon as day 5 in co-culture. When CM-Dif-labeled podocytes and CFSE-labeled hGEC were seeded together, they showed the ability to form clearly distinguishable layers. Selective expression of nephrin and CD31, respectively, was confirmed by confocal microscopy (FIG. 2J-L). Cells can be co-cultured for at least 4 weeks, maintaining their viability, thus confirming that the seeding strategy allows long-term maintenance of the cell phenotype in the chip. Following successful filling with collagen I the overall success rate for establishing the chip evaluated by visual observation was 81% (hAKPC-P+hGEC: 81.9%±3.7; hiPOD+hGEC: 88.9%±7.2; hpPOD+hGEC: 78.8%±11.1, error expressed as SEM).

Figure 2M:
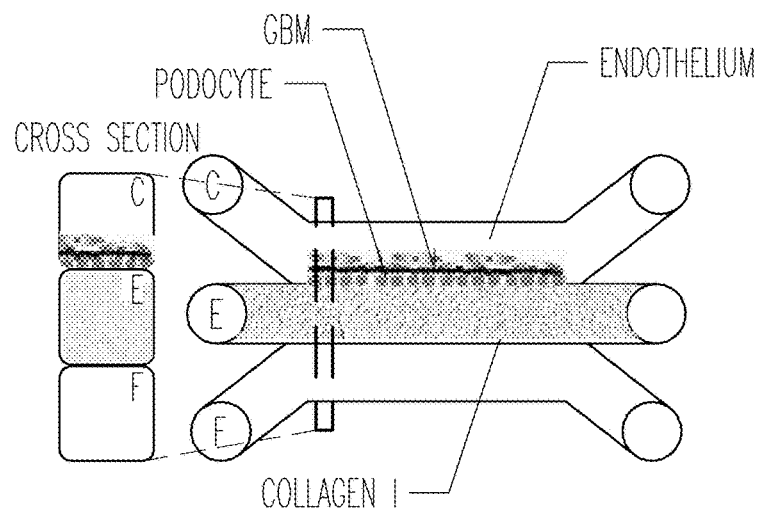
Figure 2N:
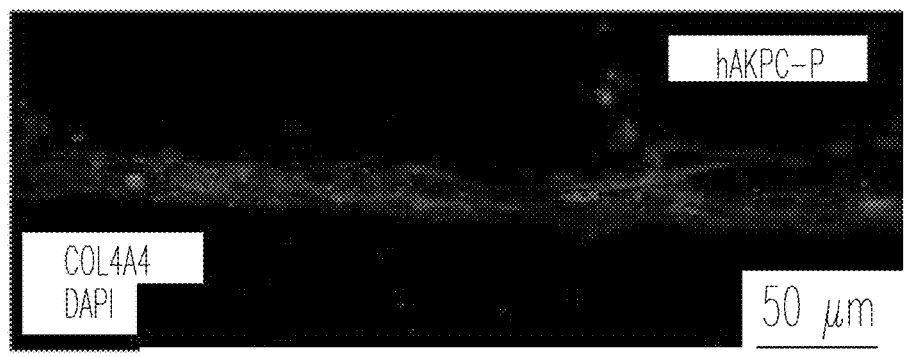
Figure 2O:
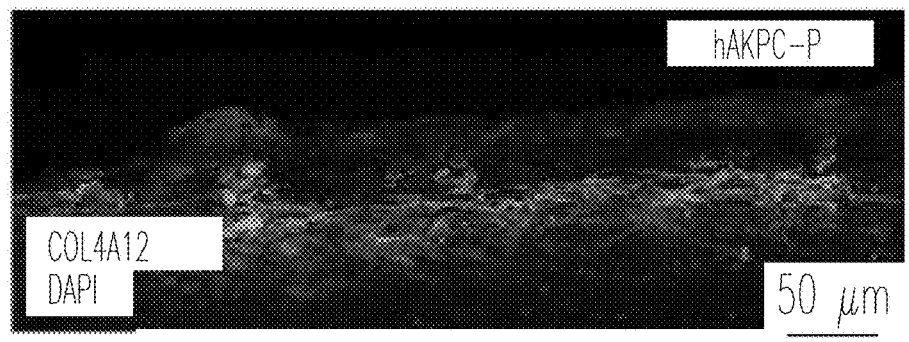
Figure 2P:
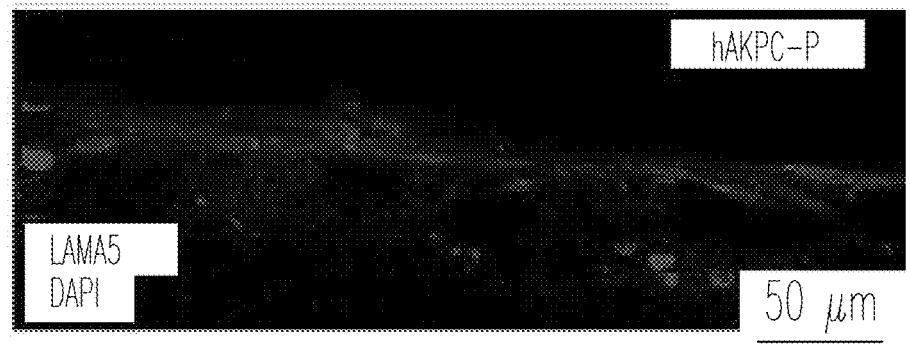
Figure 2Q:
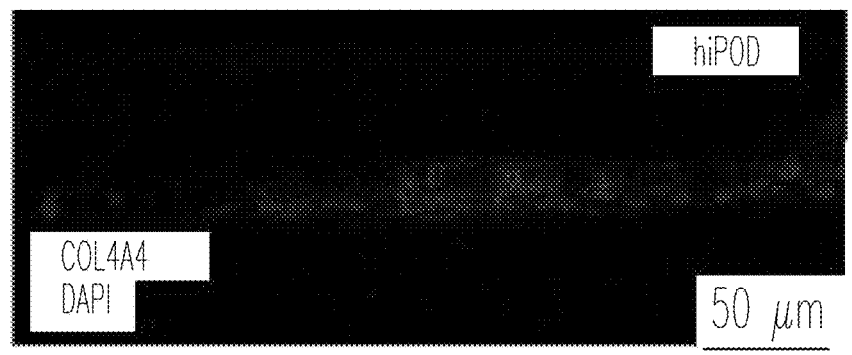
Figure 2R:
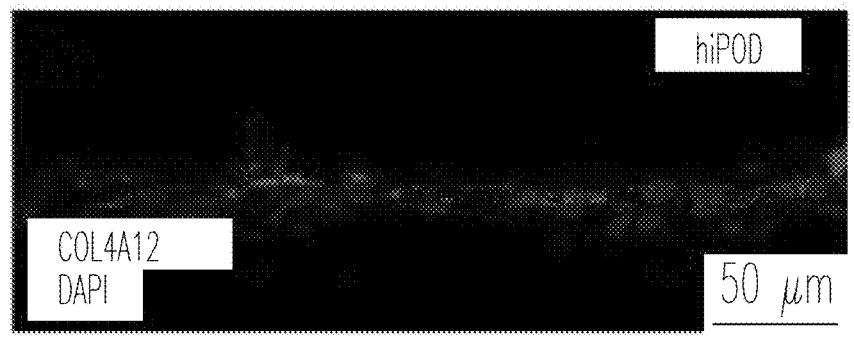
Figure 2S:
Figure 2T:
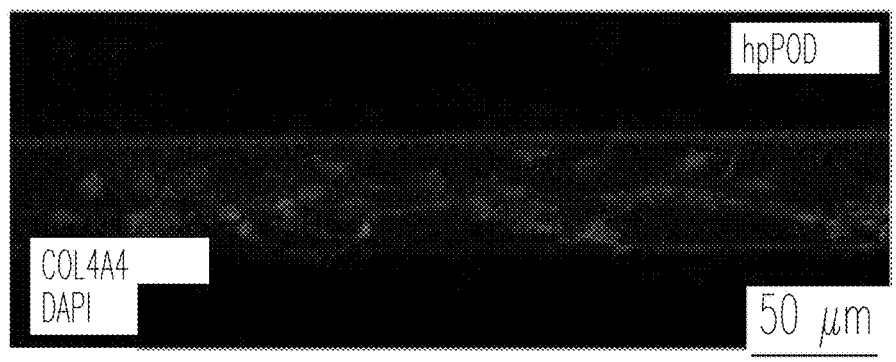
Figure 2U:
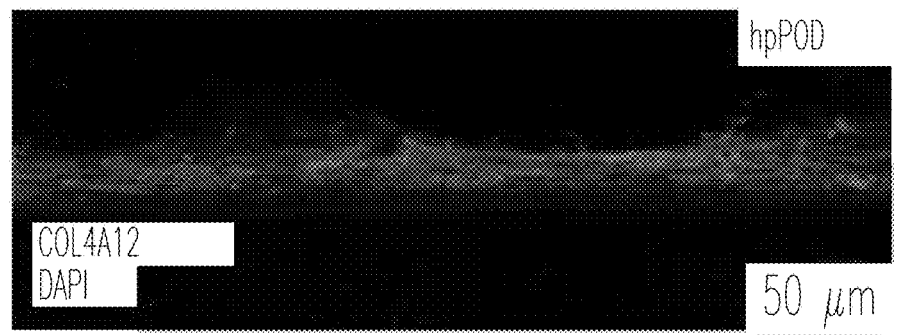
Figure 2V:
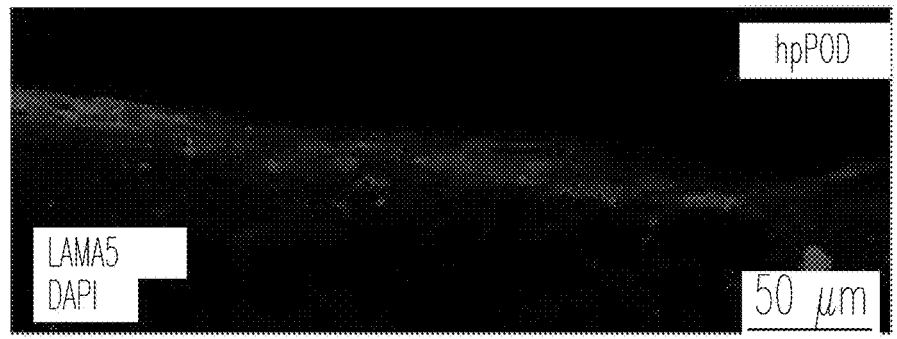
Figure 2X:
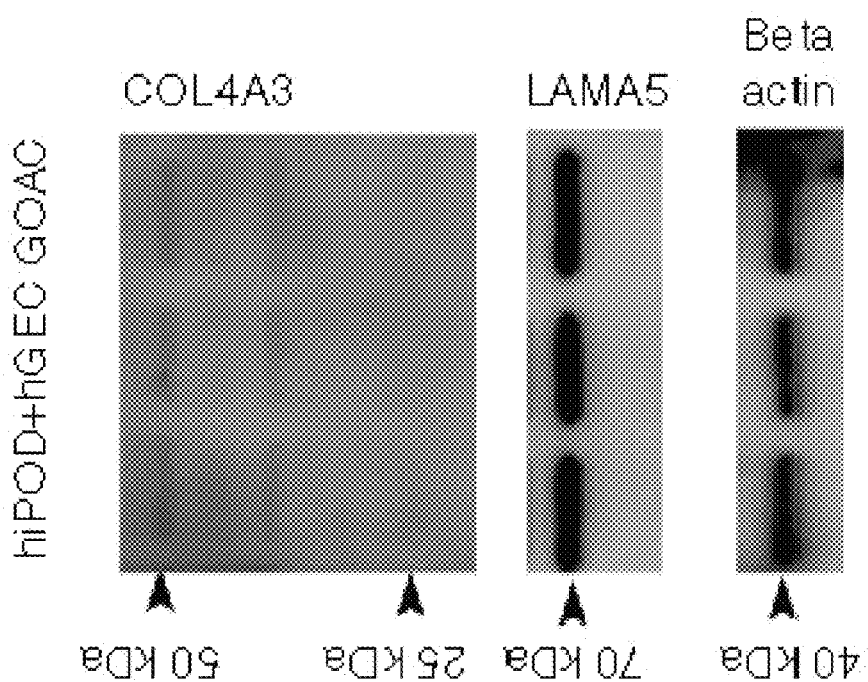
Figure 2W:
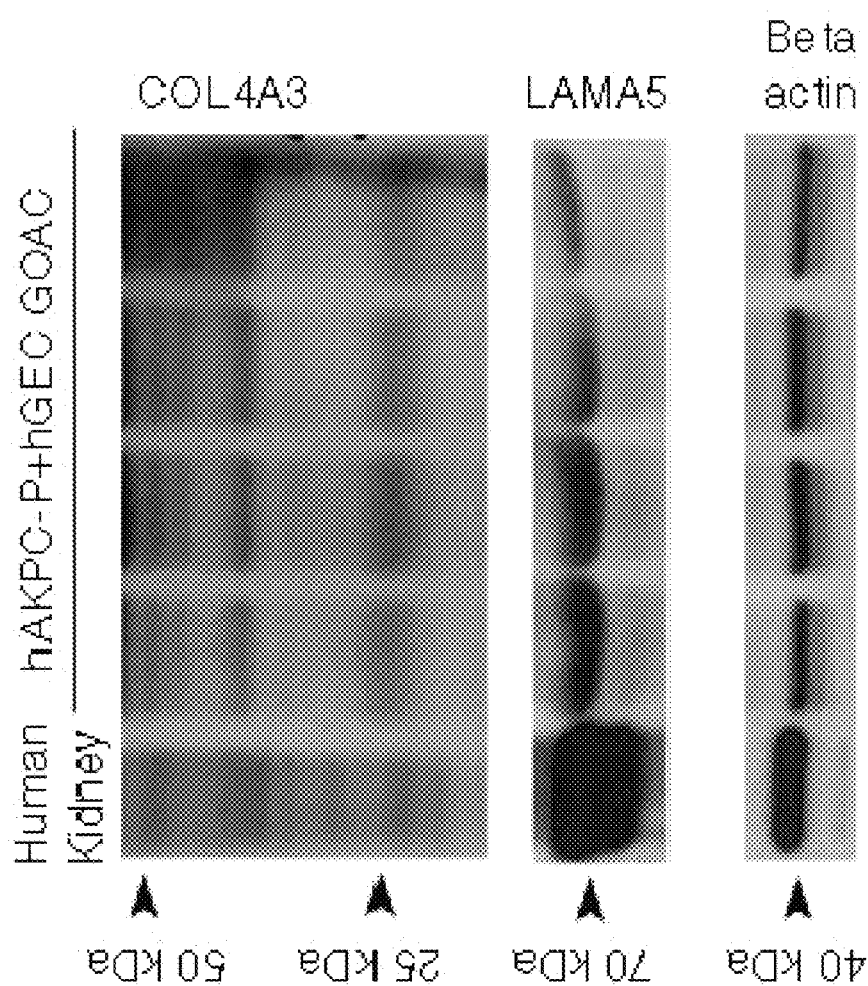
Figure 2Y:
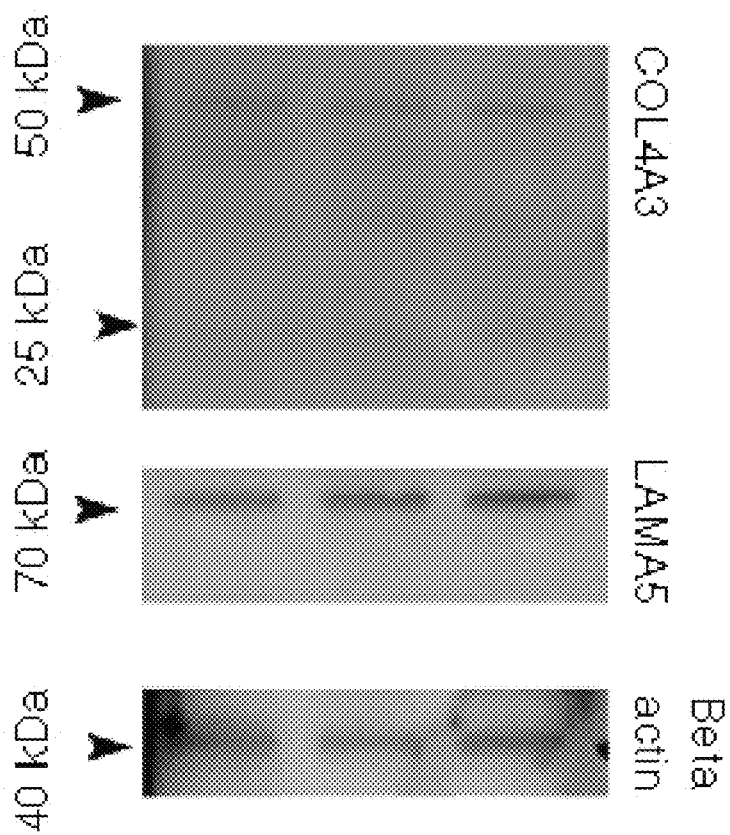

Podocytes and endothelial cells alone do not guarantee the correct function of the filtration barrier in the absence of a GBM. The human GBM is characterized by the presence of collagen IV trimers, COL4α3α4α5 and in lower quantity of COL4α1α1α2 (34), and laminins (like LAM5α2β1γ) (35). Patients affected by mutations of these membranous proteins (like AS or Pearson Syndrome (disease paragraph) (36)) present progressive CKD. Both podocytes and GEC are necessary for the proper assembly of the GBM (35). Podocytes are responsible for the production of COL4α3α4α5 while COL4α1α1α2 and LAM5α2β1γ are produced by both podocytes and hGEC (37). Production and deposition of α1, α2, and α4 chains of the COL4 as well as α5 chain of LAM for both hAKPC-P+hGEC and hpPOD+hGEC chips was confirmed (FIG. 2M); the hiPOD+hGEC chip did show lower expression of these proteins as confirmed by immunofluorescence (FIG. 2N-V). De novo deposition of GBM components collagen IV (COL4α3) and LAMA5 (FIG. 2W-Y) was confirmed by western blotting, thus demonstrating that the chips resemble in vivo GFB.

In vivo, glomerular cells are subject to the mechanical stress (shear stress) generated by the blood flowing on the apical surface of the endothelium and by the filtrate flowing from the vascular lumen to the Bowman's space (38). Shear stress affects phenotype, behavior, and permeability of both podocytes and endothelial cells and therefore plays a key role in glomerular hemodynamics (38). In glomerular capillaries, shear stress has been estimated to range from approximately 1 to about 95 dyn/cm$^2$ (corresponding to 0.1-9.5 Pa) (39). The shear stress within the present three-channel system, calculated based on a previous work (40), is equal to 0.0117 Pa (or 0.117 dyn/cm$^2$), a value closer to the physiological parameter compared to existing glomerulus-on-a-chip systems established in other labs for which the reported shear stress ranges from 0.003 (20) to 0.007 dyn/cm$^2$ (22) on the top channel.

Permselectivity as Functional Measure of a Working GOAC

Figure 3A:
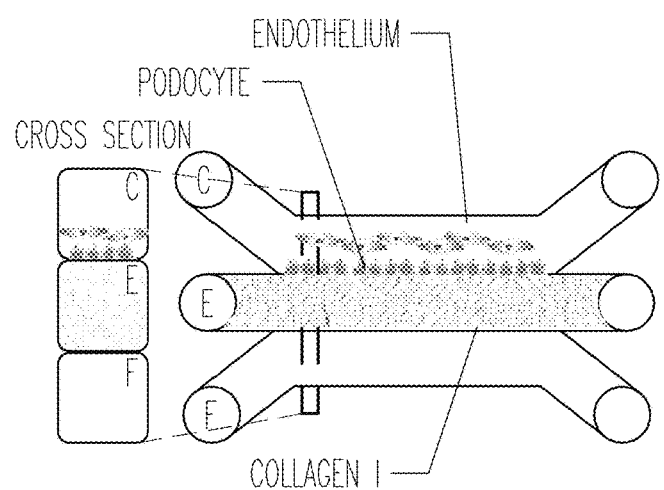
FIGS. 3A-I. GOAC permselectivity and long-term efficiency. A Representation of GOAC albumin permselectivity assay: albumin-FITC (40 mg/ml) is applied to channel C and flow through collected in channel F. Bright field showing albumin leakage after 5 min (left columns) and 60 min (right columns) in hAKPC-P+hGEC chip (B), in hiPOD+hGEC chip (C), in hpPOD+hGEC chip (D), in hAKPC-P+HuLEC chip (E); in hFIB+hGEC chip (F) and in chip with no cells but just collagen I in channel E (G). It is evident that albumin is absent only in chips generated by hAKPC-P+hGEC chip (B), in hiPOD+hGEC chip (C), in hpPOD+hGEC chip (D). Some leakage is present in hiPOD+hGEC chip (arrow) and leakage is evident in chips with no cells (G) and in chips formed by hAKPC-P+HuLEC (E) and in hFIB+hGEC chip (F). H Box plot graph of fluorescein absorbance (expressed as log) in filtrate after 60 min. All conditions with cells were significantly different (p<0.001) to chips without cells. hAKPC-P+hGEC and hpPOD+hGEC chips (but not hiPOD+hGEC) were statistically significantly different (p<0.01 and p<0.05, respectively) from chips generated using hFIB instead of podocyte lines. Number of replicates for chips used in H as follow: hAKPC-P+hGEC chip: #12; hiPOD+hGEC chip: #6; hpPOD+hGEC chip: #7; hAKPC-P+HuLEC chip: #13; hFIB+hGEC chip: #19; no cell chip: #3. Significant differences were determined by a one-way ANOVA and Holm-Sidak post hoc test, *p<0.05, p<0.01, *p<0.001. Box plots show the median, the 25th, and 75th percentiles, whiskers (median±1.5 times interquartile range), and outliers (solid circle). I Graph of fluorescein absorbance in filtrate after 60 min at 7, 14, 21, and 28 days. hAKPC-P+hGEC and hpPOD+hGEC chips maintained permselectivity efficiency at 28 days; hiPOD+hGEC permselectivity was highly reduced at 2 weeks. Red line (corresponding to a 15% loss of efficiency in retaining albumin) represents the threshold chosen as lower acceptable performance by GOAC chips. Number of replicates for chips used in i as follow: hAKPC-P+hGEC chip: 7d #13, 14d #10, 21d #9, 28d #4; hiPOD+hGEC chip: 7d #10, 14d #11; hpPOD+hGEC chip: 7d #7, 14d #22, 21d #15, 28d #15.
Figure 3B:
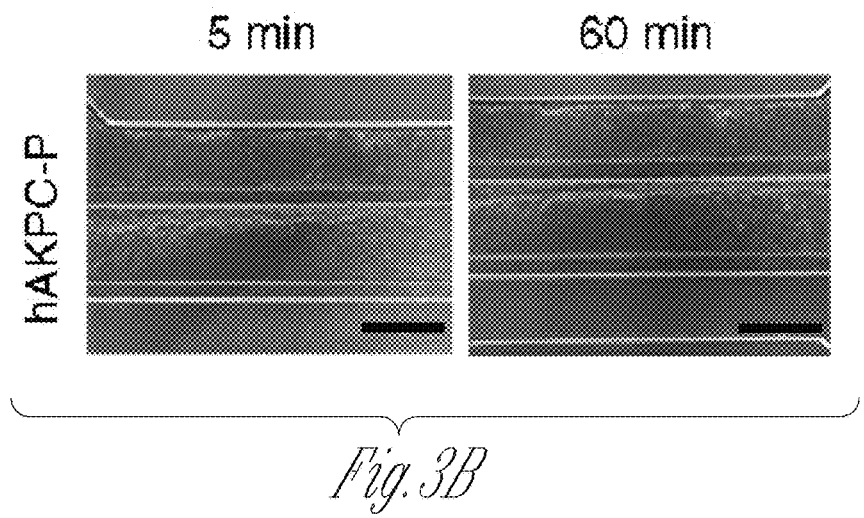
Figure 3C:
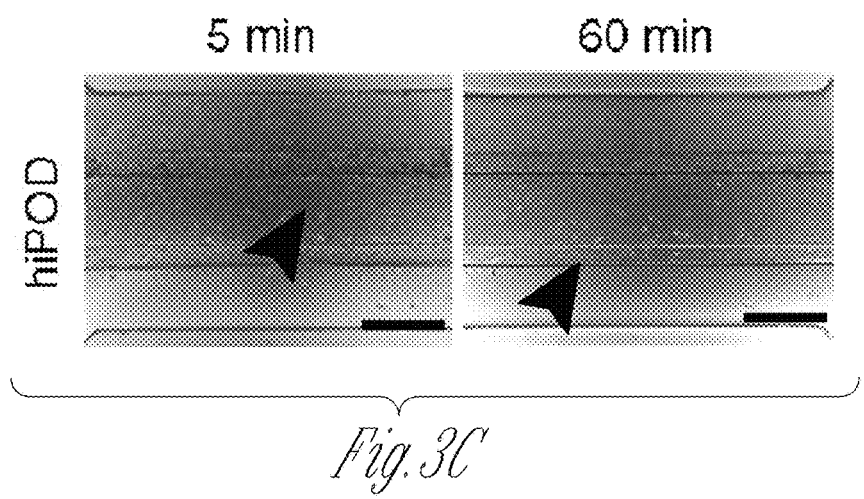
Figure 3D:
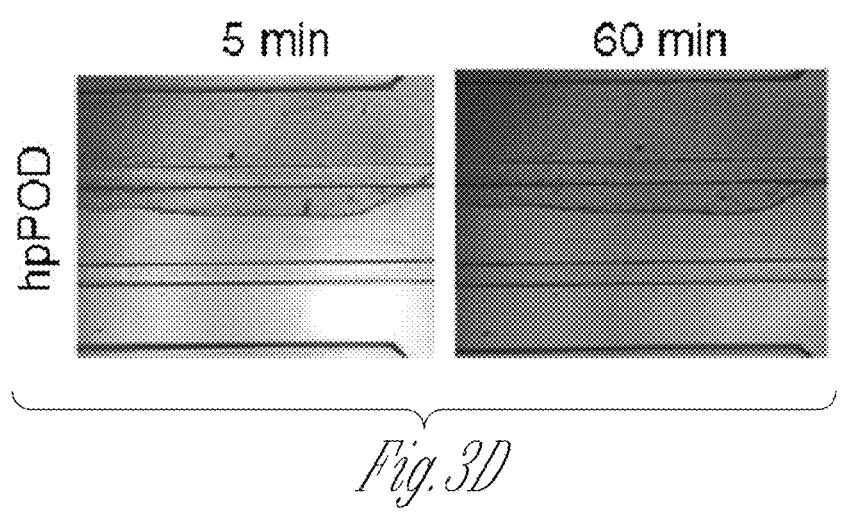
Figure 3E:
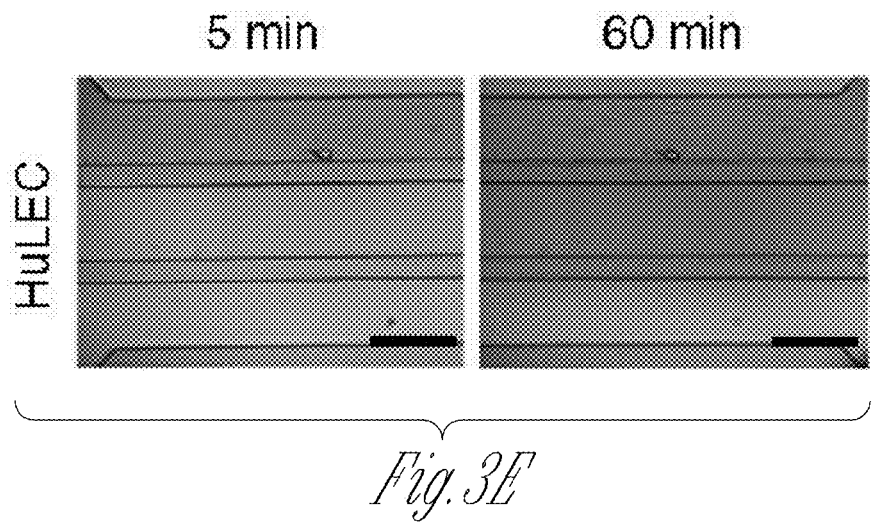
Figure 3F:
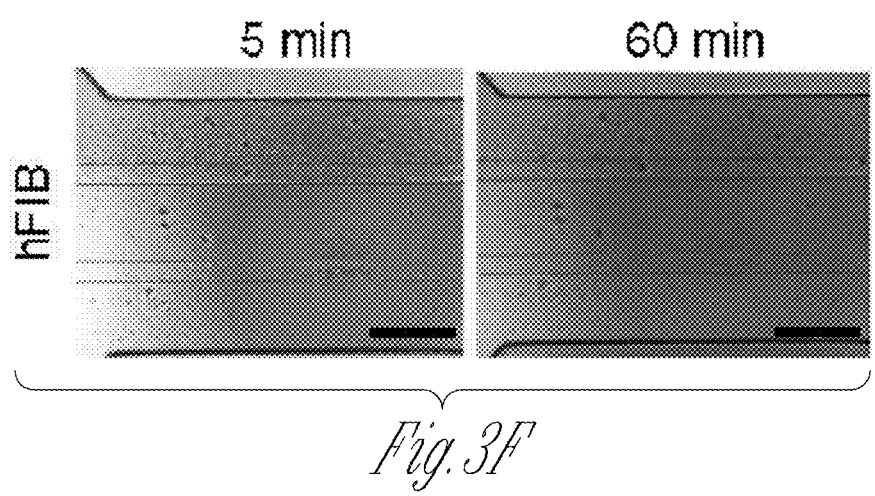
Figure 3G:
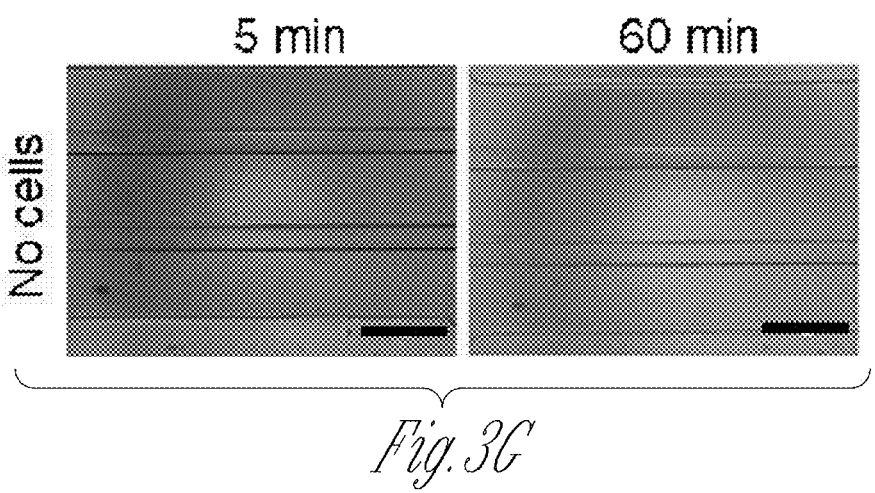
Figure 3H:
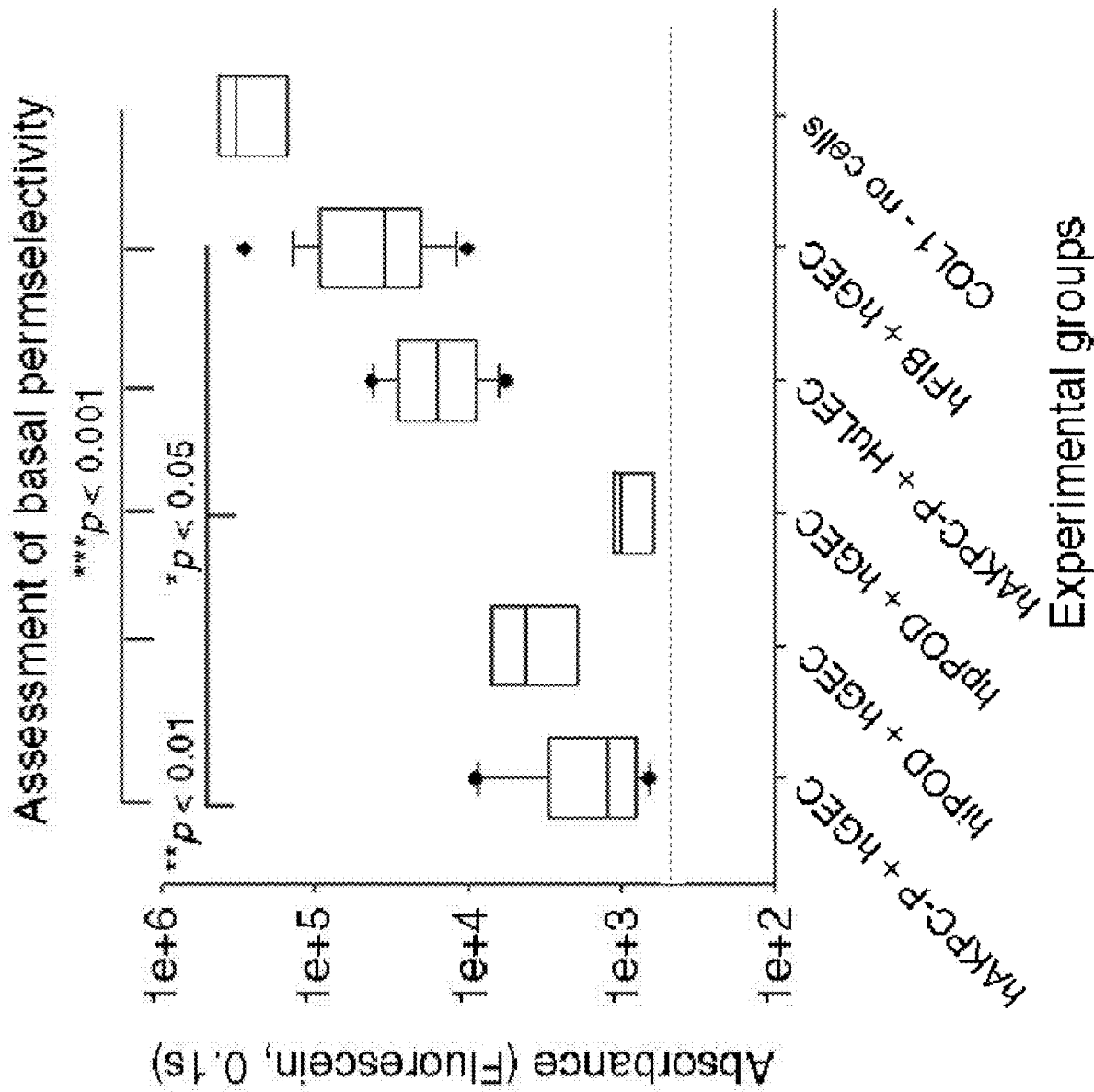
Figure 3I:
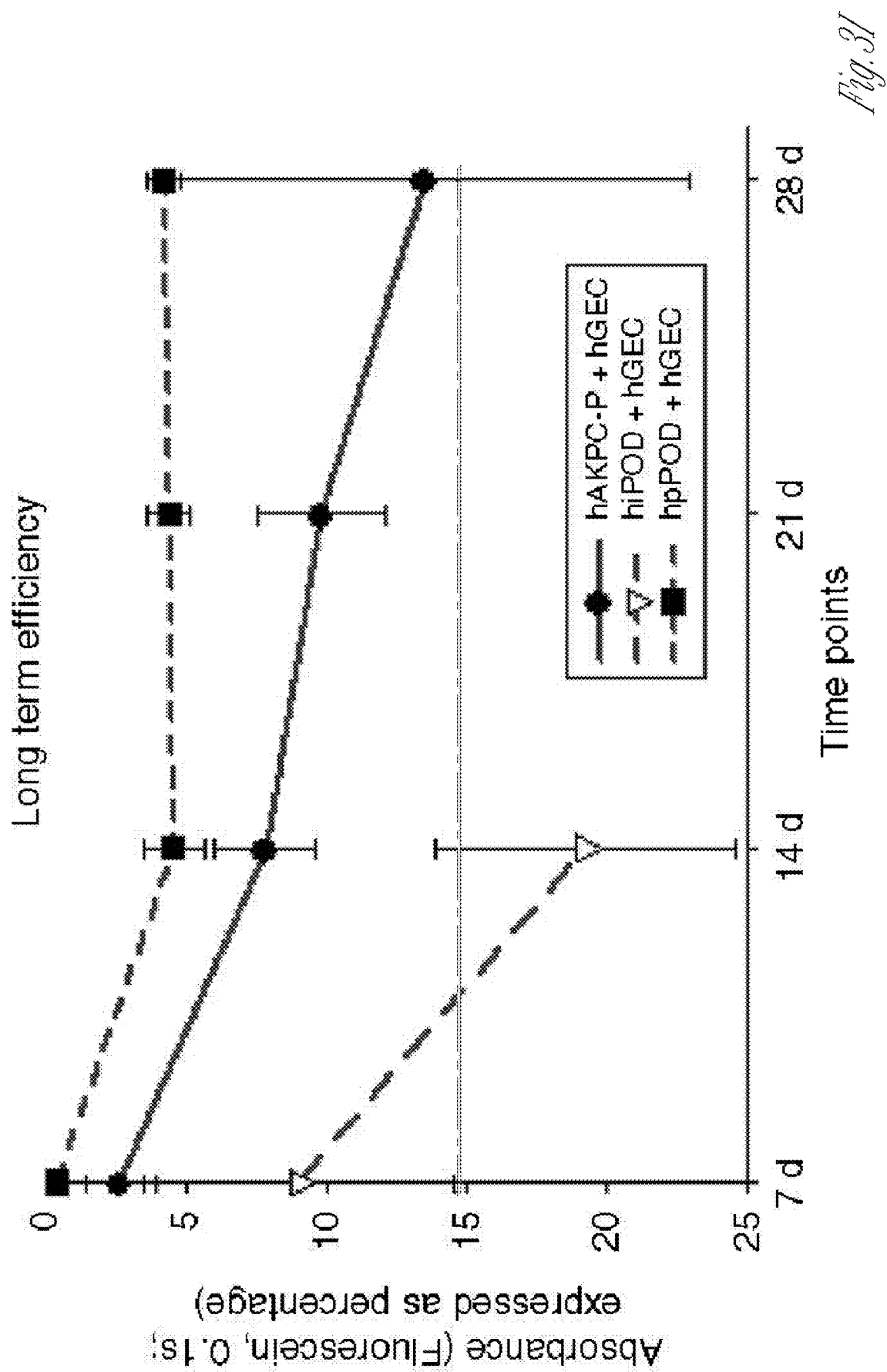

One characteristic of the GFB is permselectivity, i.e. the capacity to filter molecules based on their size (3,41). Albumin is the most abundant protein in human plasma and under physiological conditions is retained within the bloodstream. Leakage of albumin in the urine is considered a sign of kidney dysfunction, and its levels (albuminuria) correlate with the severity of glomerular injury in mice and humans (3). Chip permselectivity was tested by adding a physiological concentration of FITC-conjugated albumin (40 mg/ml (42)) to the media in channel C (FIG. 3A). hAKPC-P+hGEC, hiPOD+hGEC, and hpPOD+hGEC prevented albumin leakage at 5 and 60 min (FIG. 3B-D). To test the hypothesis that the permselectivity was provided by the two contiguous layers of podocytes and hGEC, the same experiment was repeated with chips generated with (1) podocytes+HuLEC (as negative control for hGEC, FIG. 3E), (2) human fibroblasts (as negative control for podocytes)+hGEC (FIG. 3F), or (3) devoid of cells (FIG. 3G). In all these conditions, FITC-conjugated albumin easily filled all three channels at both 5 and 60 min (FIG. 3E-G). Notably, the hAKPC-P+HuLECs chip retained albumin selectively more than fibroblasts, suggesting that podocytes are possibly the main players of albumin permselectivity in the chip as already hypothesized in vivo (43). Interestingly, hiPOD chips did not exhibit a statistically significant difference compared to chips built using hFIB, further suggesting that the immortalized line is less suitable for these assays (FIG. 3H). The lower efficiency of hiPOD permselectivity could possibly stem from to the lower expression of laminin or collagen-binding components like $\alpha 3$, $\alpha 1$, and $\beta 1$ integrin chains and CD151 (which associates with cell-matrix complexes like integrins), integrin chains $\beta 3$, $\alpha 5$, $\alpha V$ that instead mediate fibronectin binding and are activated in progressive CKD, as shown in previous work (25). These alterations do not favor proper GBM production and attachment to it (44) and possibly affects their ability to assemble a strong barrier to retain albumin. Long-term analysis of GOAC permselectivity confirmed the maintenance of cell viability of the GOAC as well as efficiency of permselectivity for at least 28 days following the hGEC seeding in both hAKPC-P+hGEC and hpPOD+hGEC chips. Performance of hiPOD chips markedly decreased at 2 weeks (FIG. 3I).

To prove GOAC permselectivity, together with the capability of retaining albumin, its capacity of filtering molecules that are freely filtered by glomerulus in vivo, such as inulin, was also tested (45). It was demonstrated that the GOAC can filter inulin, thus confirming that the GOAC is constituted by a functional GFB that can accurately perform differential clearance of albumin and inulin, like the in vivo GFB.

To further support the advantages of the platform in comparison to other in vitro models and to confirm that the instant GOAC replicates in bona fide the semi-permeability of GFB, podocyte-endothelial barriers were generated on 24-well transwells using the same protocol (including cell isolation, media, and timing) used for the chips. All transwells exhibited a significant albumin leakage thus suggesting that, under the same conditions, this platform cannot perform as efficiently as the GOAC.

Puromycin Aminonucleoside Promotes Albumin Leakage in the GOAC

Figure 4A:
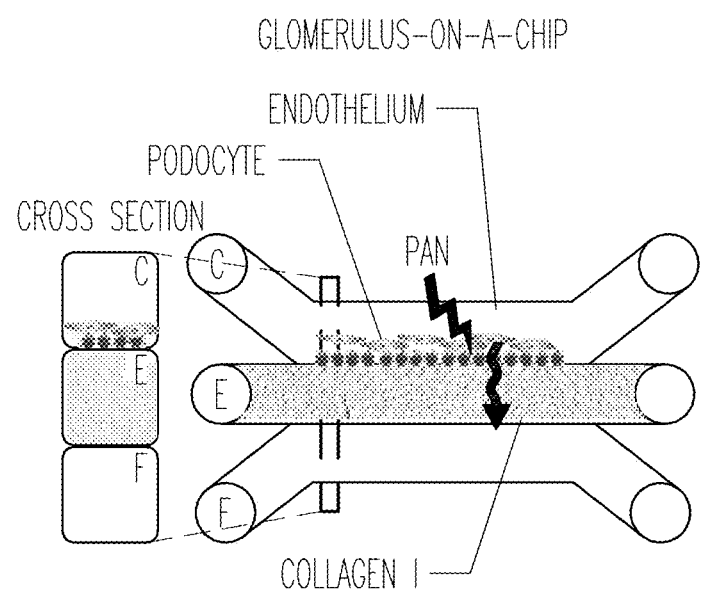
Figures 4B, 4C, 4D:
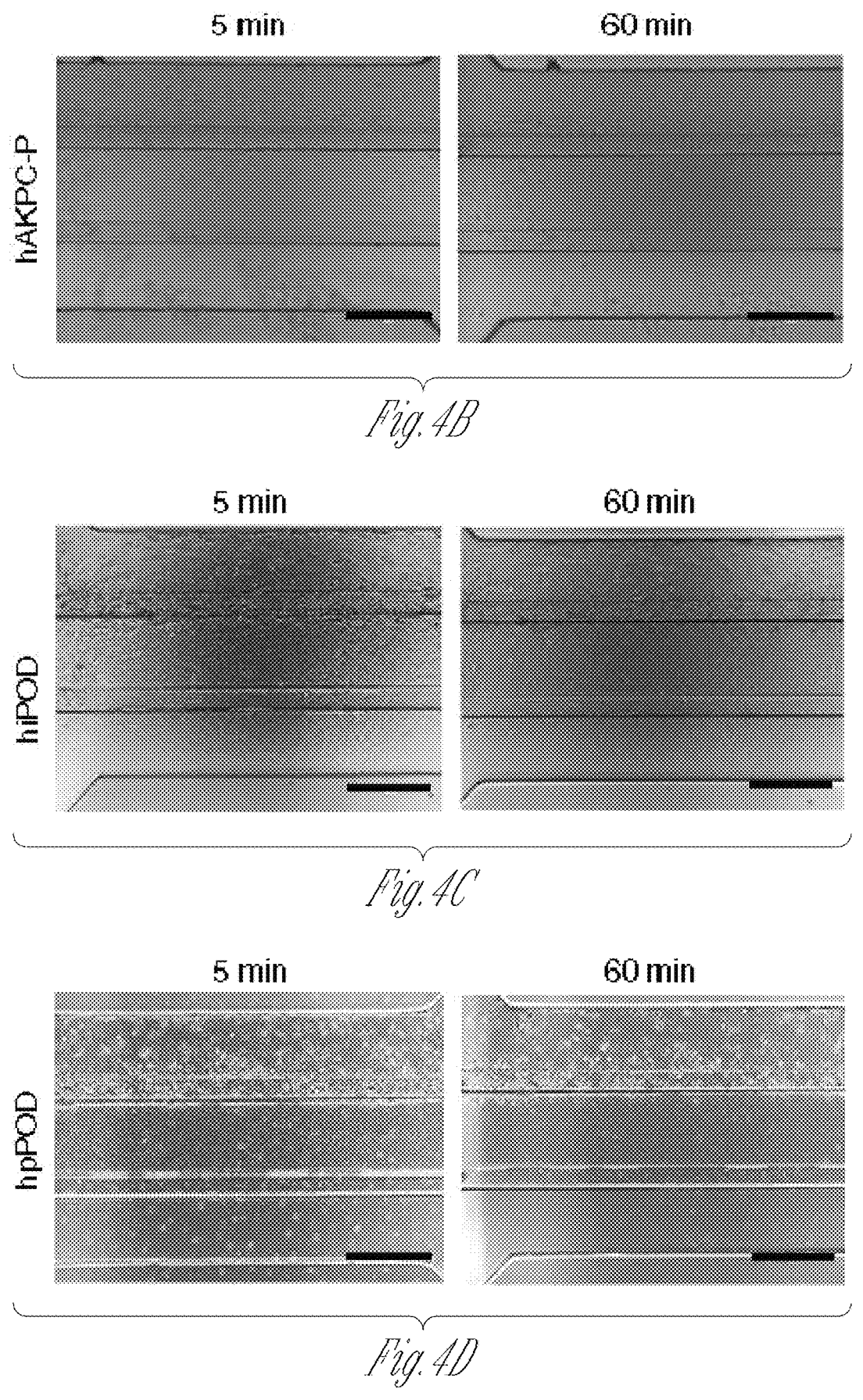
Figure 4E:
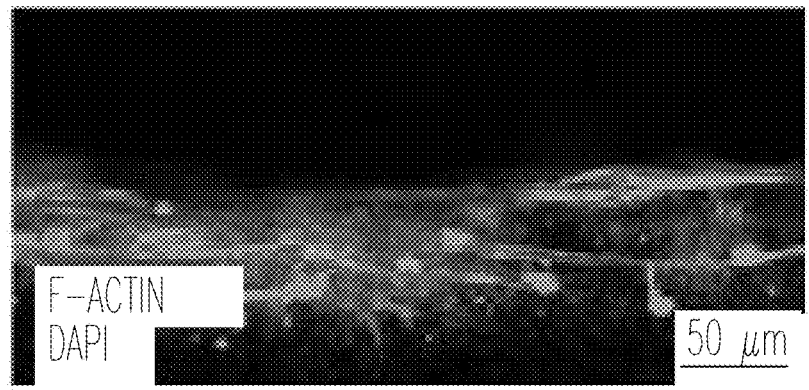
Figure 4F:
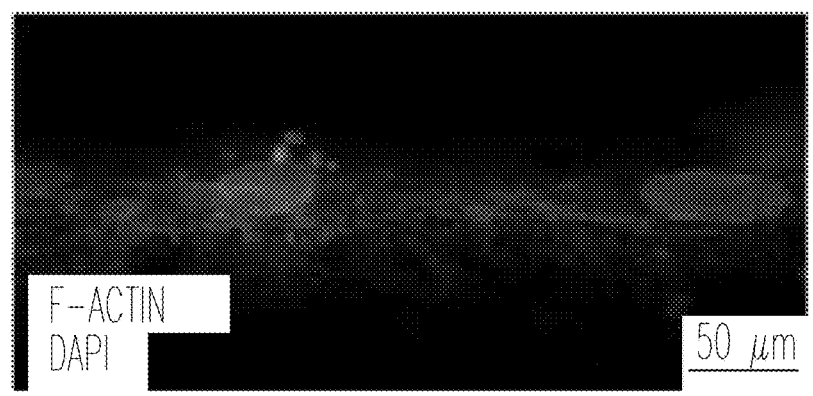
Figure 4G:
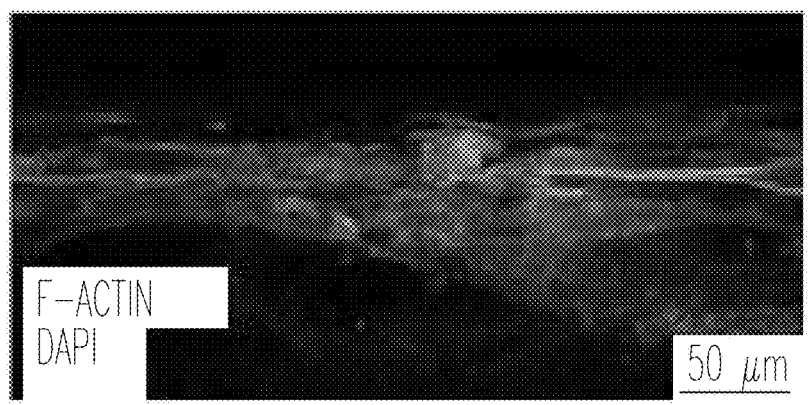
Figure 4H:
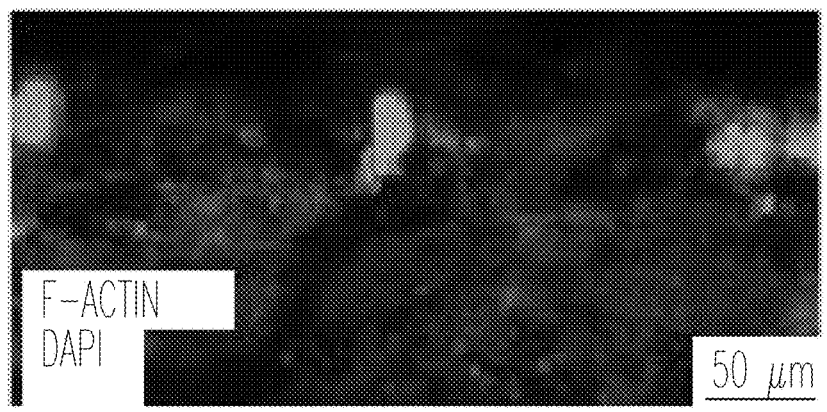
Figure 4I:
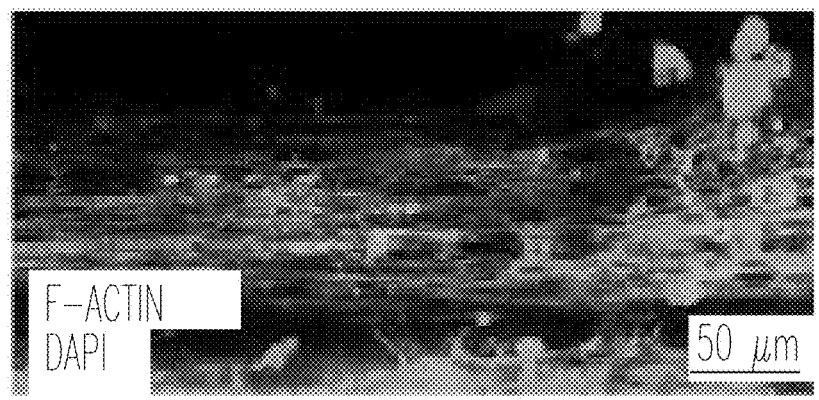
Figure 4J:
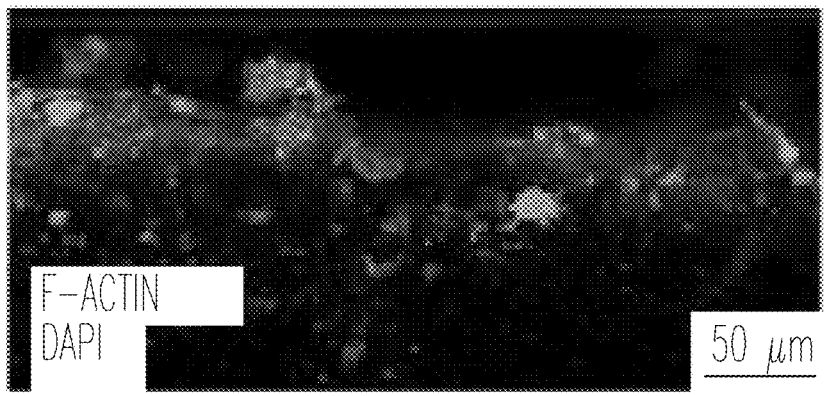
Figure 4K:
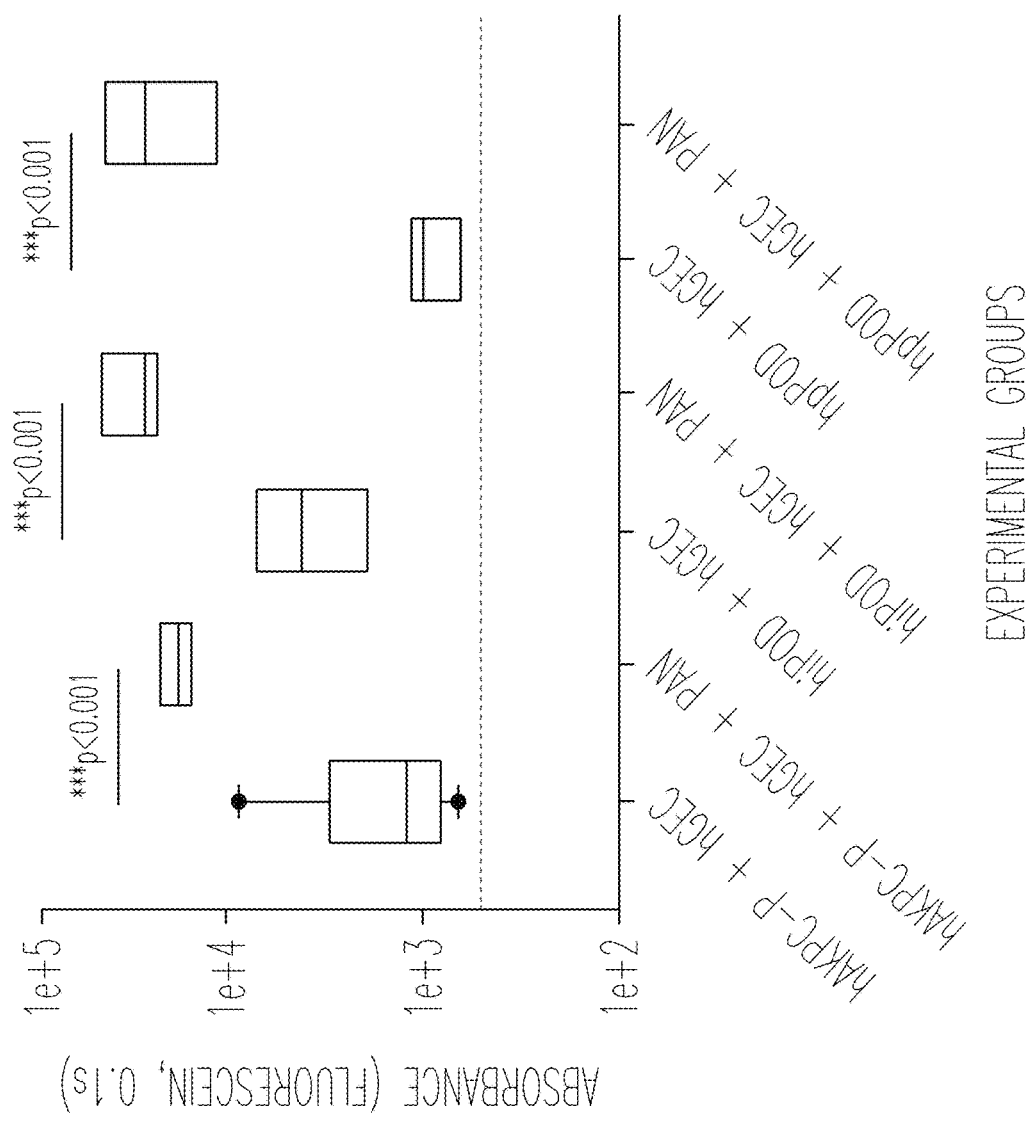

To test the hypothesis that the GOAC can model a kidney injury state, the GOAC was exposed to puromycin aminonucleoside (PAN; FIG. 4A), a nephrotoxic agent that alters podocyte morphology and function (25) and can induce focal segmental glomerulosclerosis (FSGS) in mice (46). When added to GOAC, PAN induced podocyte injury as documented by cytoskeleton rearrangement and loss of permselectivity for albumin at 60 min after stimuli (FIG. 4B-J). The levels of albumin leakage were similar across GOAC with hAKPC-P+hGEC, hiPOD+hGEC, or hpPOD+hGEC (FIG. 4K). Together, these results show that the human GOAC developed in this study mimics function and injury manifestations of the kidney GFB.

Sera from Individuals with MN Shows Albumin Leakage in the GOAC

To further characterize the system and determine the capacity of GOAC to react to human samples, the response of GOAC was tested against sera from individuals affected by MN, a major cause of nephrotic syndrome (proteinuria with associated peripheral edema and lipid abnormalities, among other abnormalities) in adults (47). MN is initiated by the deposition of circulating anti-podocyte autoantibodies in the subepithelial space of the GFB, inducing complement-mediated podocyte injury and proteinuria (48).

First, the ability of IgG to cross the glomerular endothelial cell monolayer on which hGEC were allowed to grow to confluency and form a continuous layer was tested. It was confirmed that FITC-IgG added to the top chamber could be detected on the lower chamber after approximately 6 h, thus confirming the ability of hGEC to allow passage of IgG, a process also confirmed in vivo (49, 50).

Figure 5A:
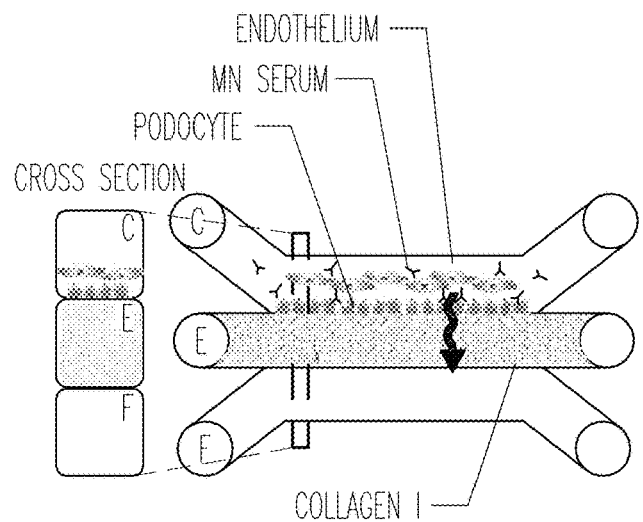
FIGS. 5A-J. Evaluation of permselectivity using human membranous nephropathy serum samples. A Representation of the GOAC albumin permselectivity assay to MN serum exposure. Following a 24 h incubation with media supplemented with 0.5% serum from healthy individuals (CTRL1 and CTRL2) or MN patients (MN1-6), albumin-FITC is applied to channel C and flow-through collected in channel F. B-G Bright field showing albumin leakage after 5 min (left columns) and 60 min (right columns) after exposure to healthy and MN patients serum in hAKPC-P+hGEC (B, C), hiPOD+hGEC (D, E), and hpPOD+hGEC (F, G) chips. Leakage is evident in hAKPC-P+hGEC and hpPOD+hGEC but not in hiPOD+hGEC chips after exposure to MN serum. H-J Box plot graph of fluorescein absorbance (expressed as log) in filtrate collected after 60 min after serum exposure in hAKPC-P+hGEC (h), hiPOD+hGEC (I), and hpPOD+hGEC (J) chips. Statistically significant increase in albumin permeability is evident after exposure to MN sera only in hAKPC-P+hGEC and hpPOD+hGEC chips. Number of replicates for chips used in H is as follows: hAKPC-P+hGEC chip and CTRL1: #7; hAKPC-P+hGEC chip and CTRL2:#8; hAKPC-P+hGEC chip and MN1: #4; hAKPC-P+hGEC chip and MN2: #7; hAKPC-P+hGEC chip and MN3: #3. hAKPC-P+hGEC chip and MN4: #4; hAKPC-P+hGEC chip and MN5: #7; hAKPC-P+hGEC chip and MN6: #3. Number of replicates for chips used in i as follow: hiPOD+hGEC chip and CTRL1: #6; hiPOD+hGEC chip and CTRL2: #4; hiPOD+hGEC chip and MN1: #11; hiPOD+hGEC chip and MN2: #5; hiPOD+hGEC chip and MN3: #4; hiPOD+hGEC chip and MN4: #11; hiPOD+hGEC chip and MN5: #5; hiPOD+hGEC chip and MN6: #4. Number of replicates for chips used in J is as follows: hpPOD+hGEC chip and CTRL1: #8; hpPOD+hGEC chip and CTRL2: #9; hpPOD+hGEC chip and MN1: #6; hpPOD+hGEC chip and MN2: #7; hpPOD+hGEC chip and MN3: #7; hpPOD+hGEC chip and MN4: #6; hpPOD+hGEC chip and MN5: #7; hpPOD+hGEC chip and MN6: #7. For D. G. J significant differences were determined by a one-way ANOVA and Holm-Sidak post hoc test, *$p<0.05$, $p<0.01$, *$p<0.001$ Box plots show the median, the 25th and 75th percentiles, whiskers (median±1.5 times interquartile range), and outliers (solid circle).
Figure 5B:
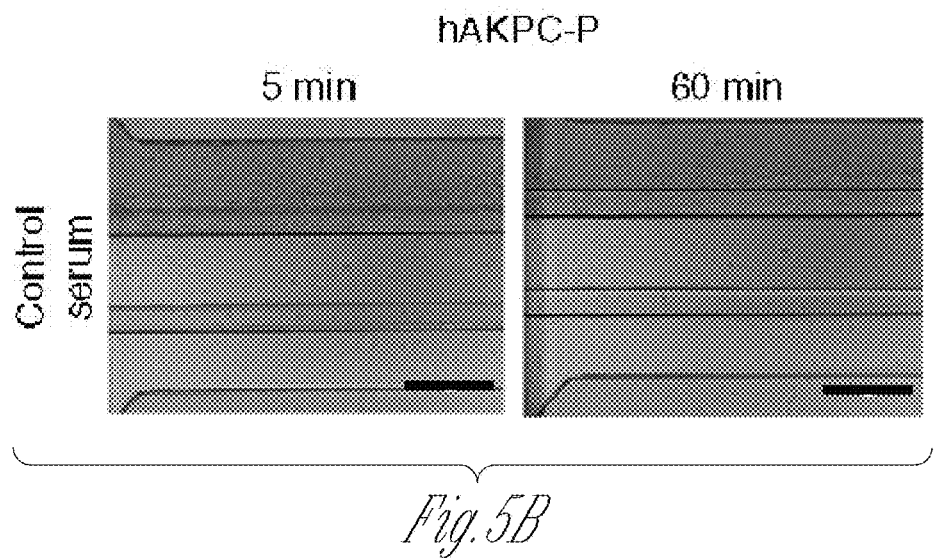
Figure 5C:
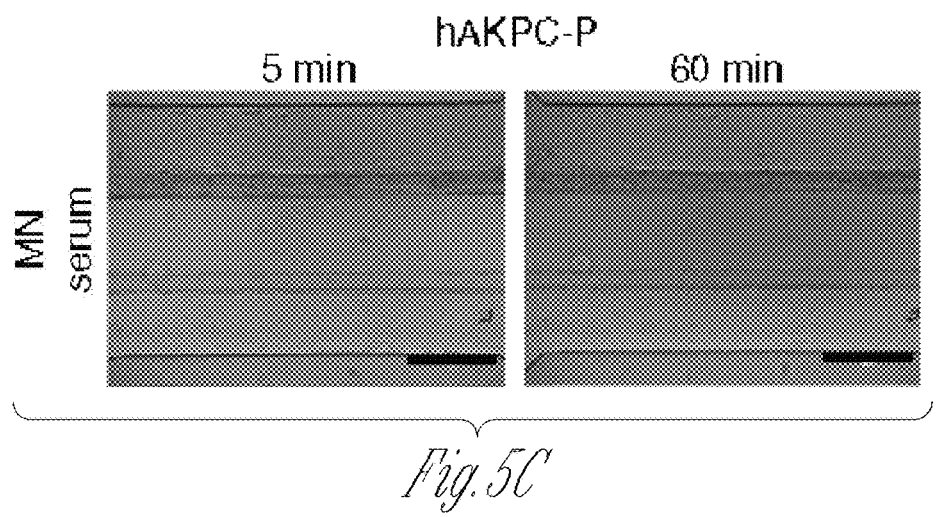
Figure 5D:
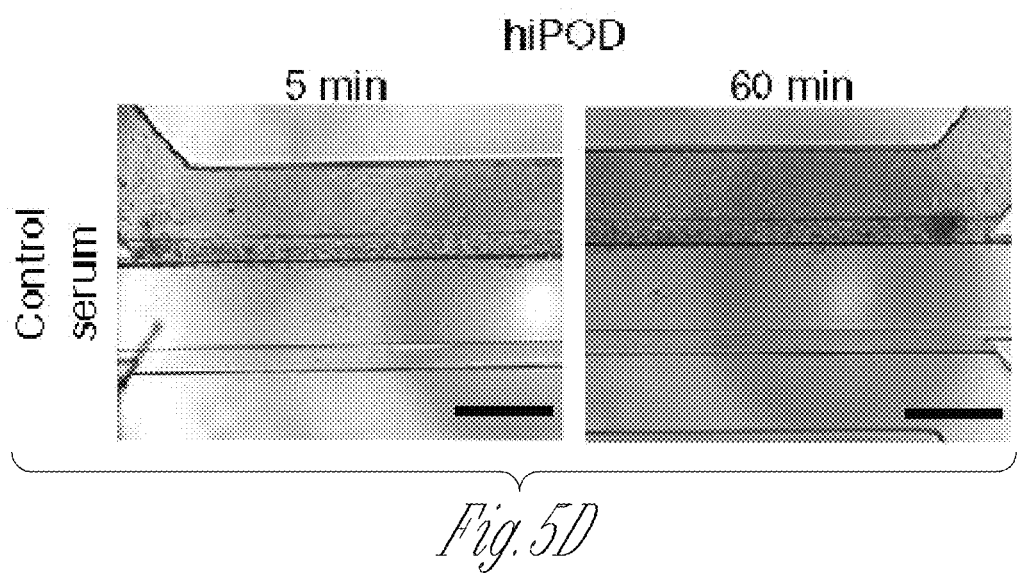
Figure 5E:
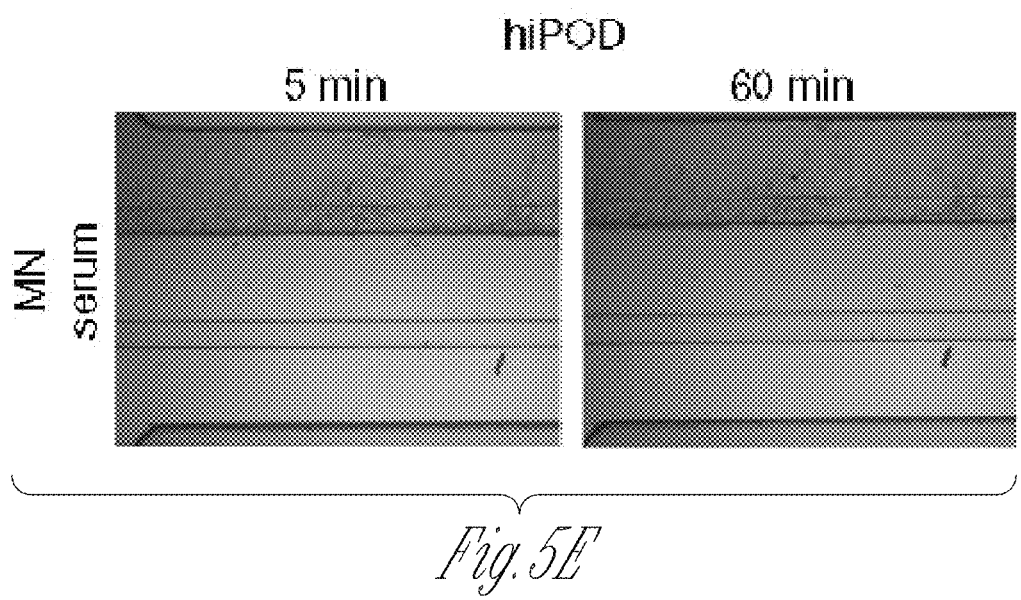
Figure 5F:
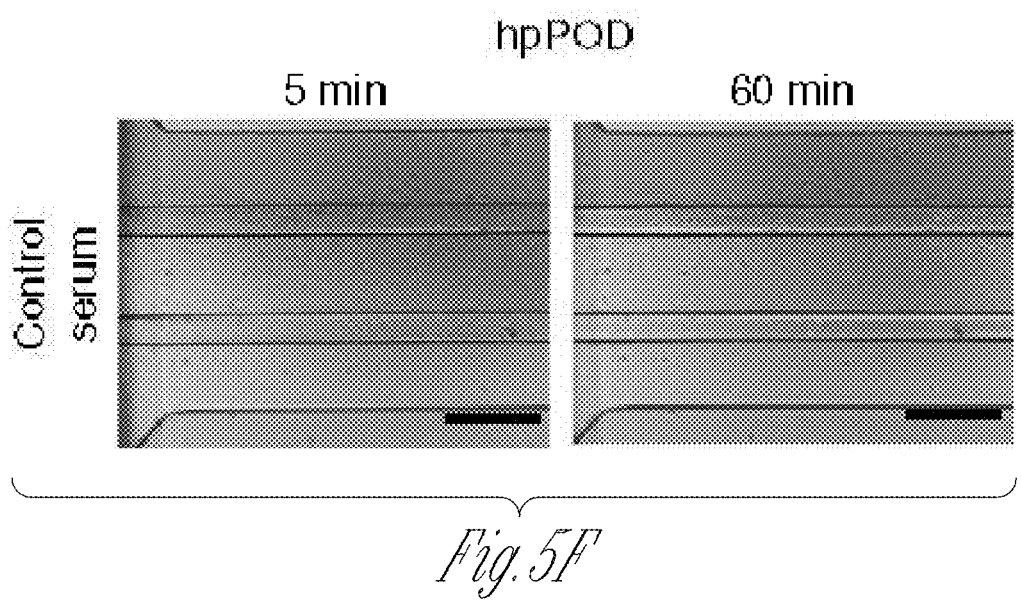

After 24 h of exposure to medium containing 0.5% of serum from MN patients or healthy controls (FIG. 5A), the chips with MN serum, but not control sera, showed total IgG and IgG4 deposition on the podocytes, recapitulating the main features of MN nephropathy (51). While chips generated from all podocyte types showed an increase in albumin leakage (FIG. 5B-J), only hAKPC-P (FIG. 5H) and hpPOD (FIG. 5I) chips confirmed a statistically significant loss of permselectivity following exposure to MN serum while hiPOD (FIG. 5J) failed to respond properly.

Figure 6B:
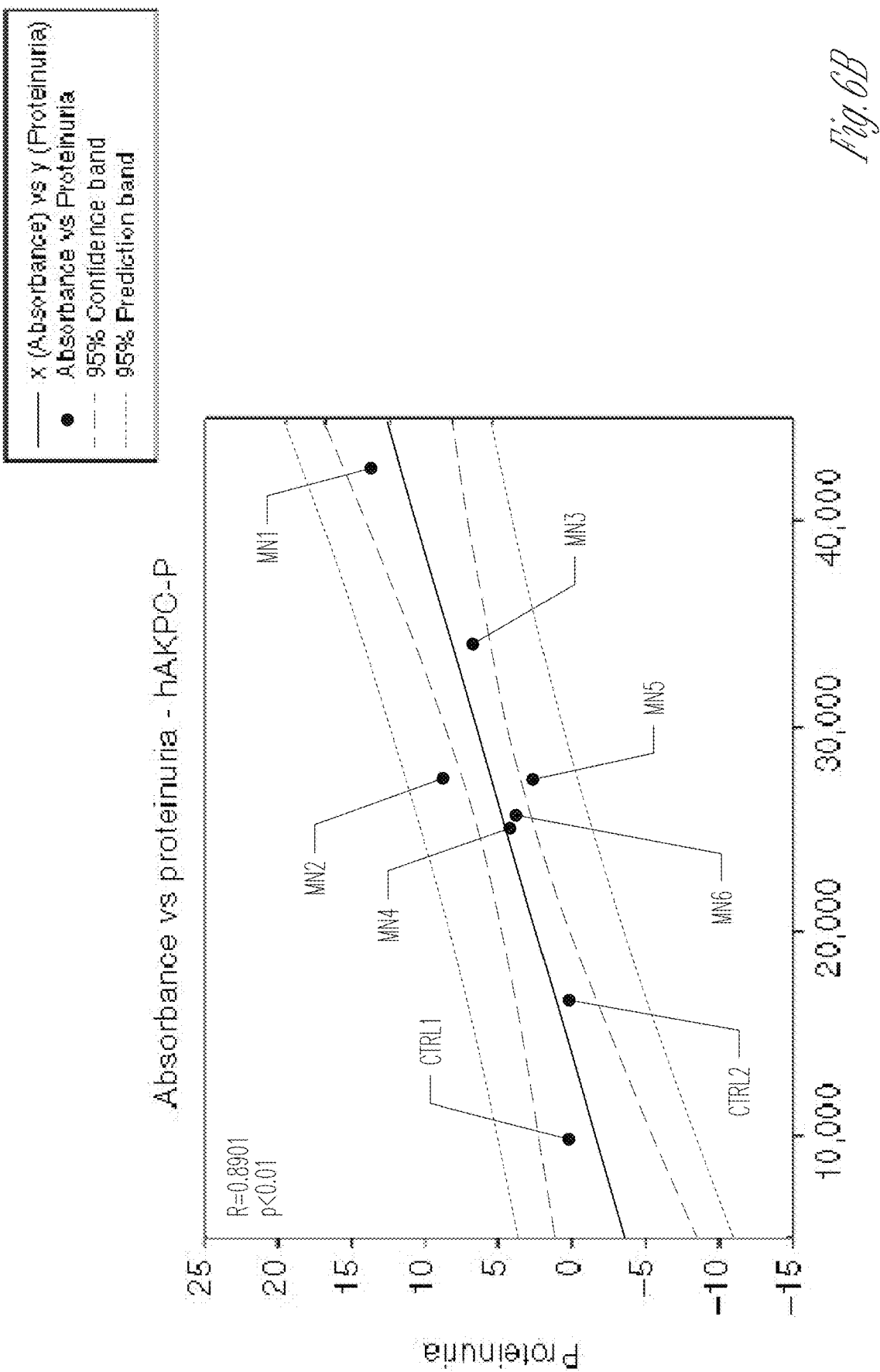
Figure 6C:
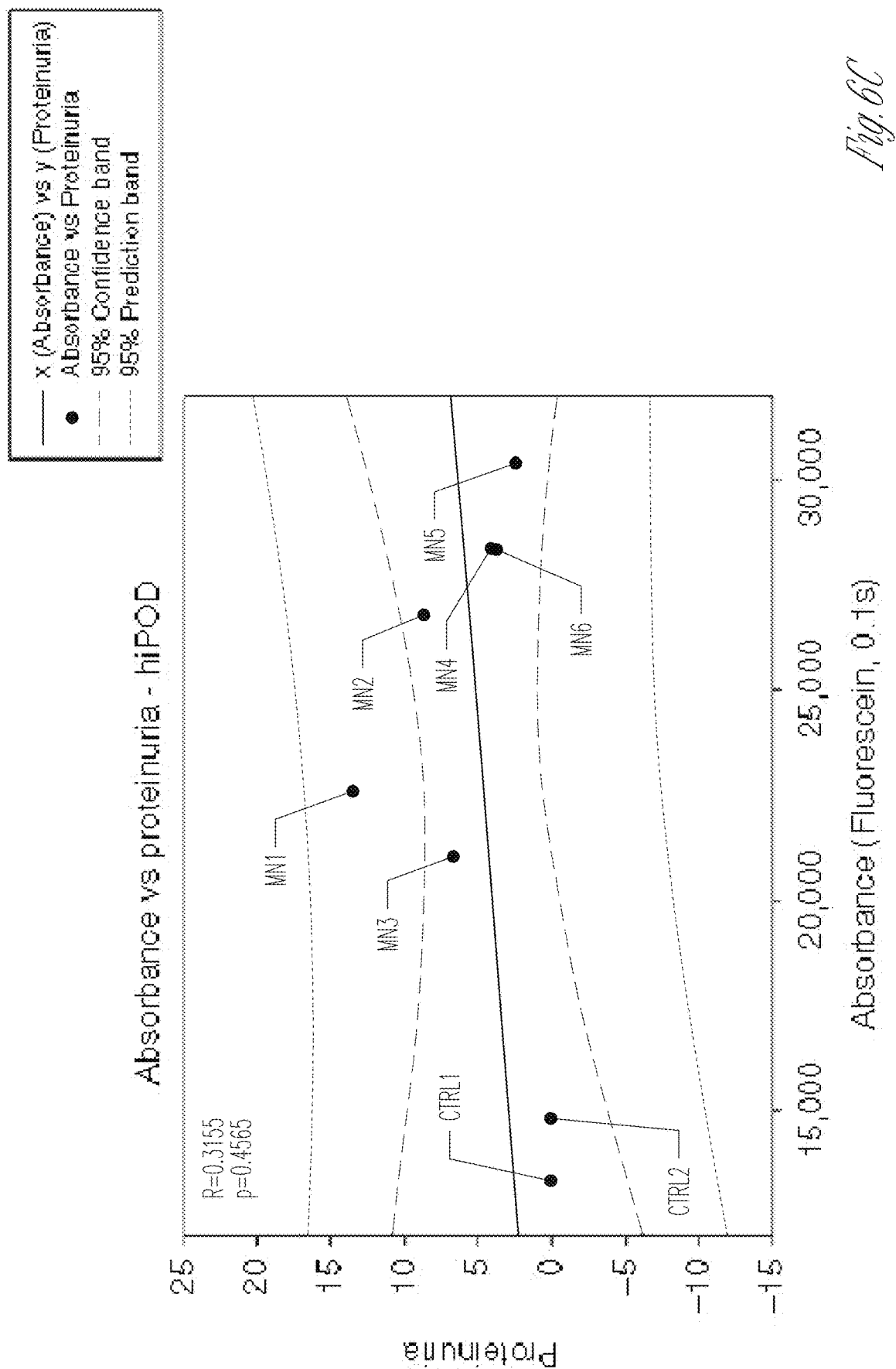
Figure 6D:
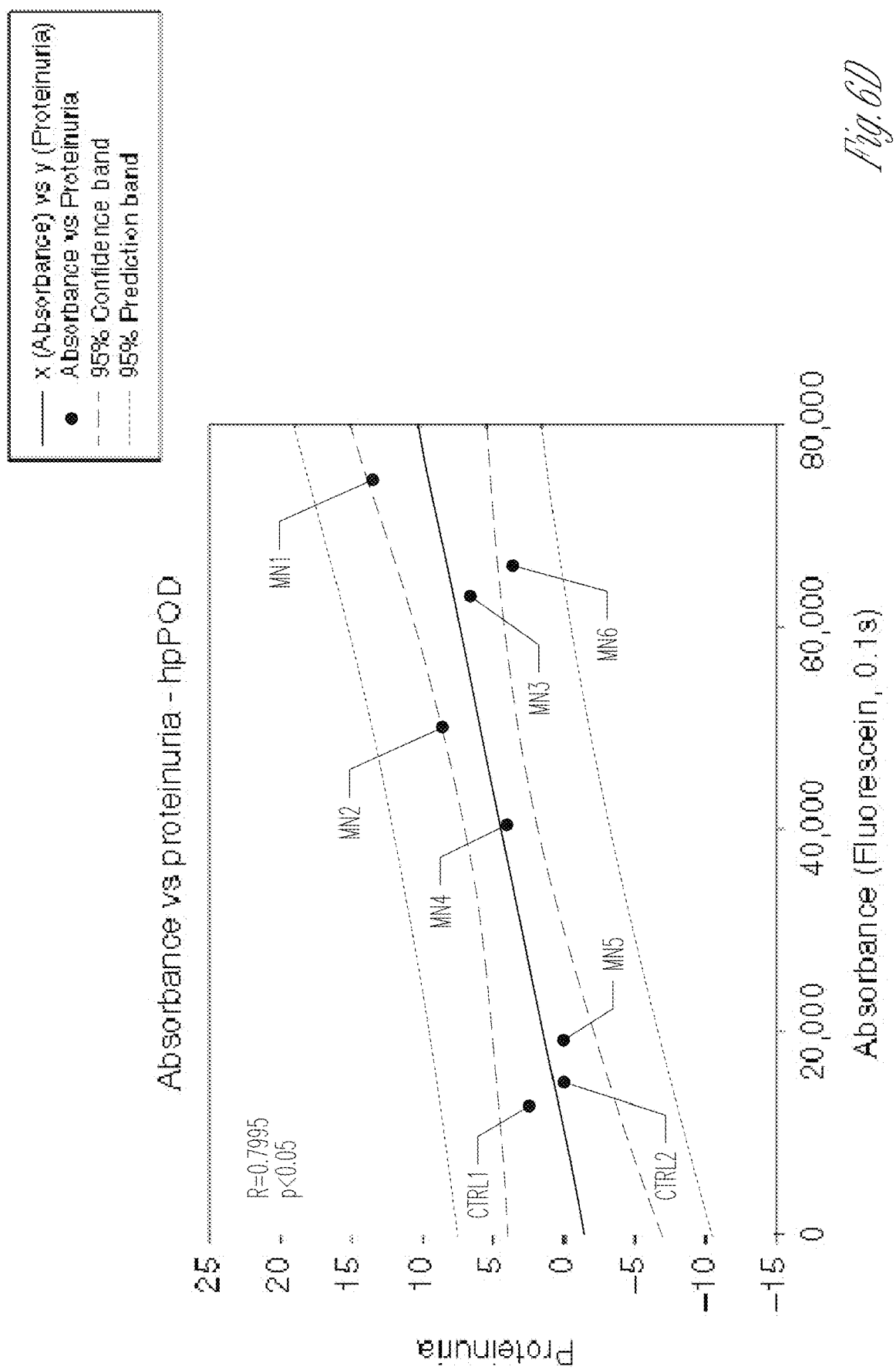

Next, the relationship was measured between the extent of albumin leakage (proteinuria) in the chips (measured as FITCabsorbance in the filtrate collected in channel F) with proteinuria measured in the same patients (FIG. 6) and anti-PLA2R (Phospholipase A2 receptor) titer by linear regression analysis. It was found that proteinuria highly correlated with the diagnostic results obtained in the chips generated using hAKPC-P (R=0.8901, p<0.01, FIG. 6B) and primary podocytes (R=0.7995, p<0.05, FIG. 6D) with a confidence of at least 95%. This correlation was not statistically significant in the chip generated with hiPOD (R=0.3155, p=n.s., FIG. 6C). The same results were obtained when performing the same analysis with anti-PLA2R antibody titer from MN patients, confirming high correlation for hAKPC-P and hpPOD chips but not hiPOD chips.

Modeling Mechanism of MN Injury in Podocyte in the GOAC

It was then tested whether the GOAC could be used to perform cell-based investigations to delineate mechanisms responsible for podocyte damage and disruption of the filtration barrier. PLA2R is the major podocyte target antigen in MN patients (52, 53) along with less common ones like, for example, THSD7A and NEP1 (52, 53). It was confirmed that hAKPC-P, hiPOD, and hpPOD express PLA2R both before and after seeding on the chip. However, when western blotting analysis was performed to quantify PLA2R expression, it was found that hiPOD exhibited the lowest expression of PLA2R (significantly different when compared to hpPOD or hAKPC-P, p<0.05). A lower expression of antigen by hiPOD might explain their limited response to MN.

Figure 5G:
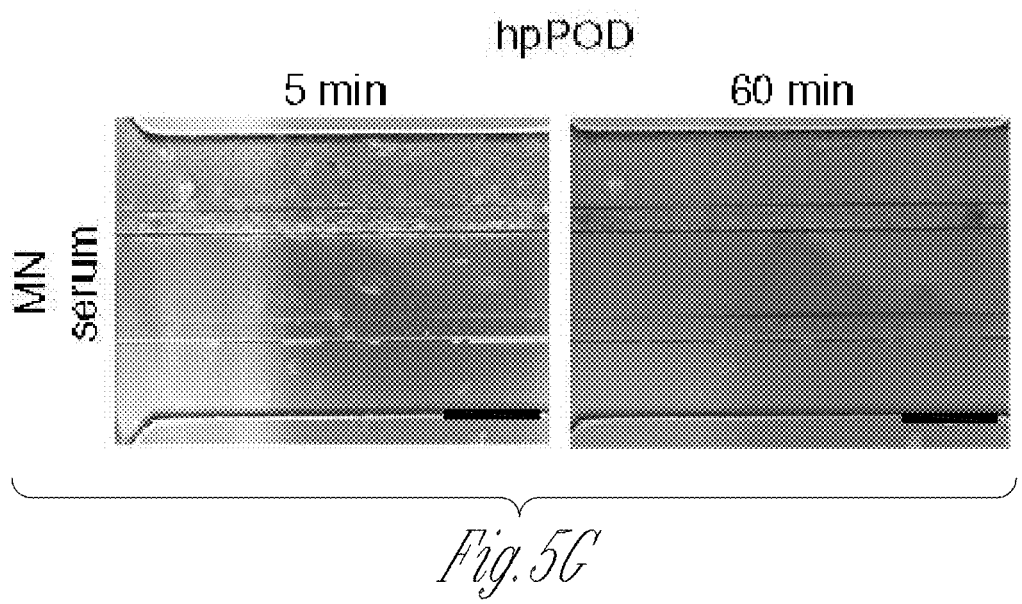
Figure 5H:
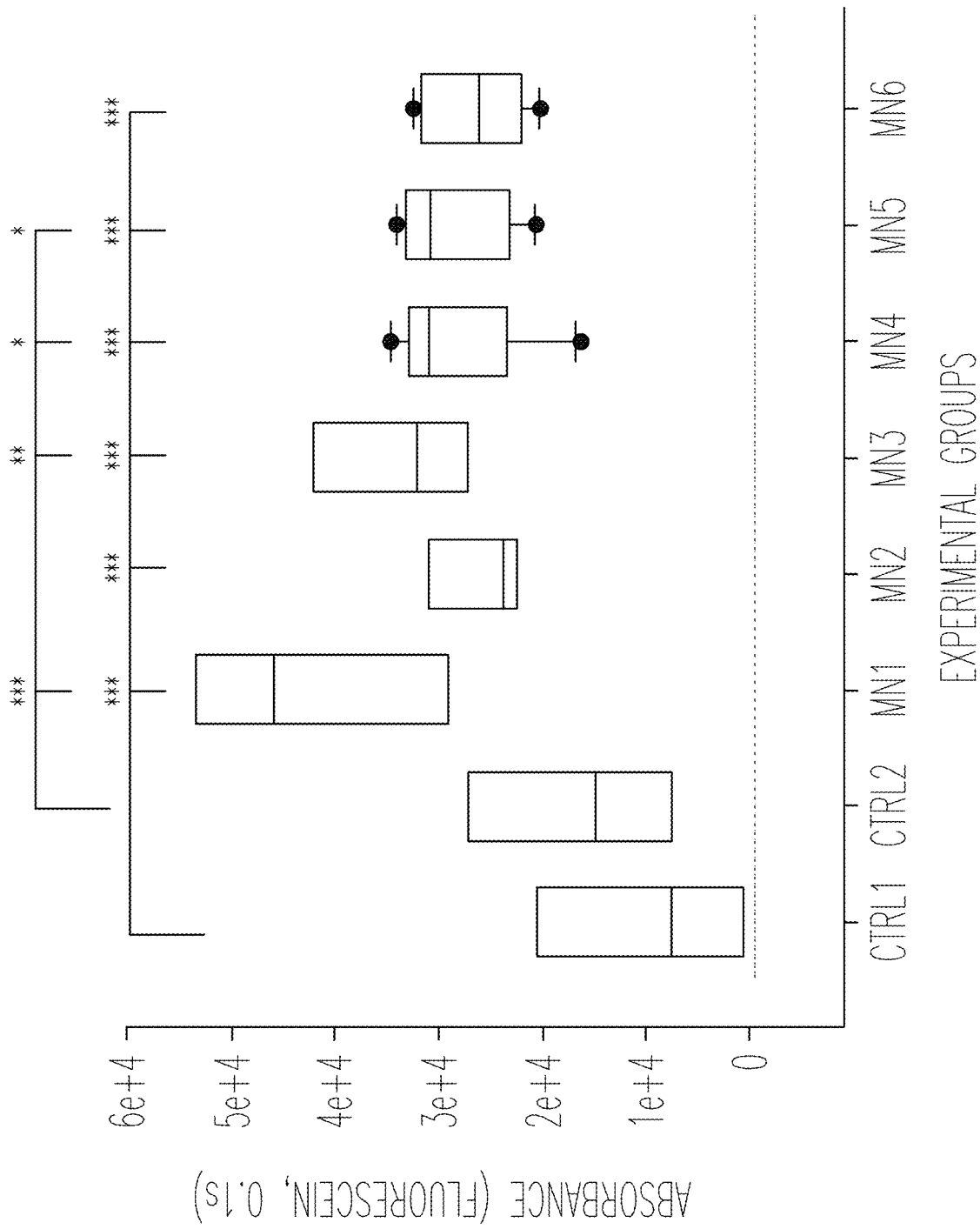
Figure 5I:
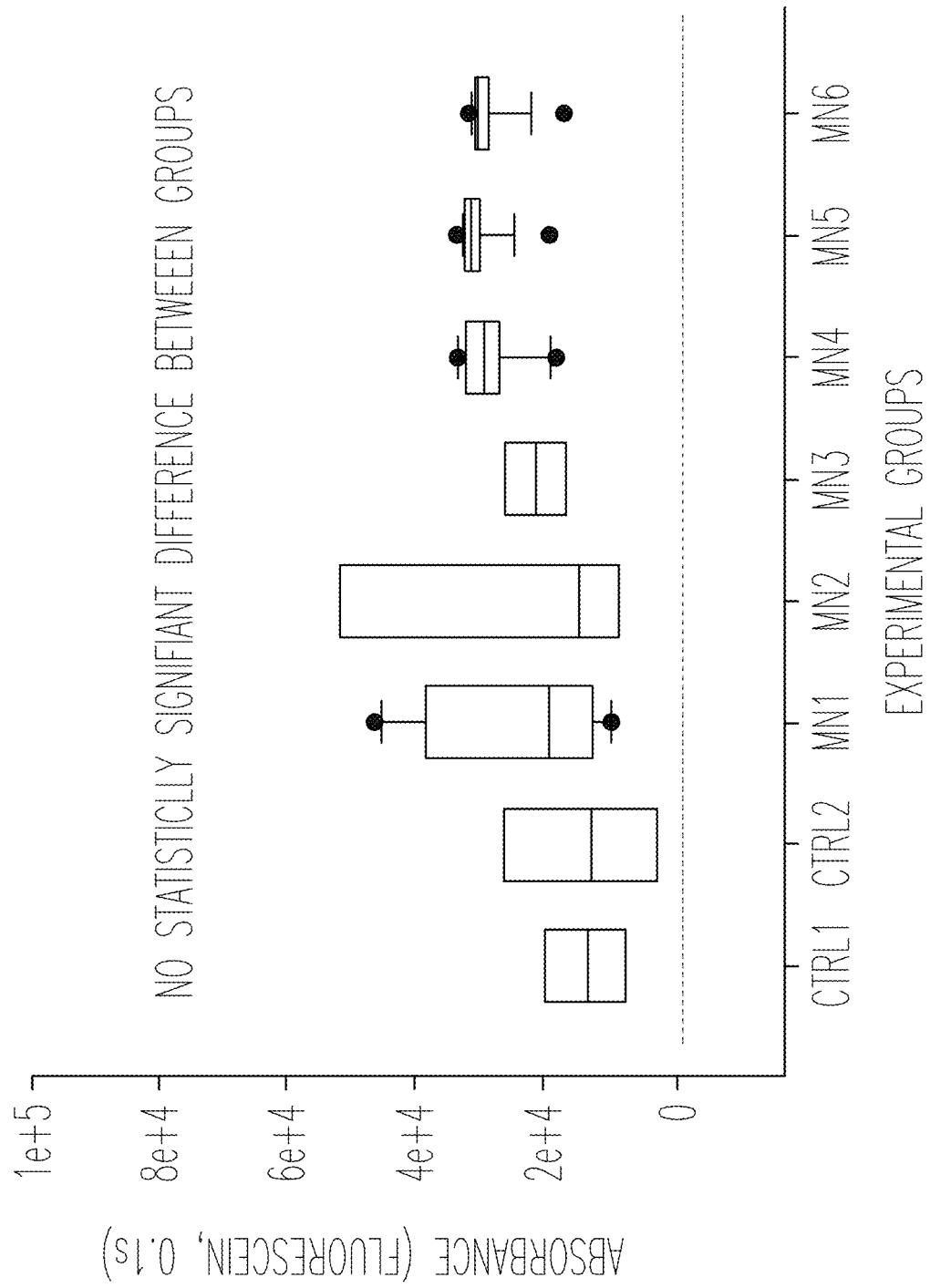
Figure 5J:
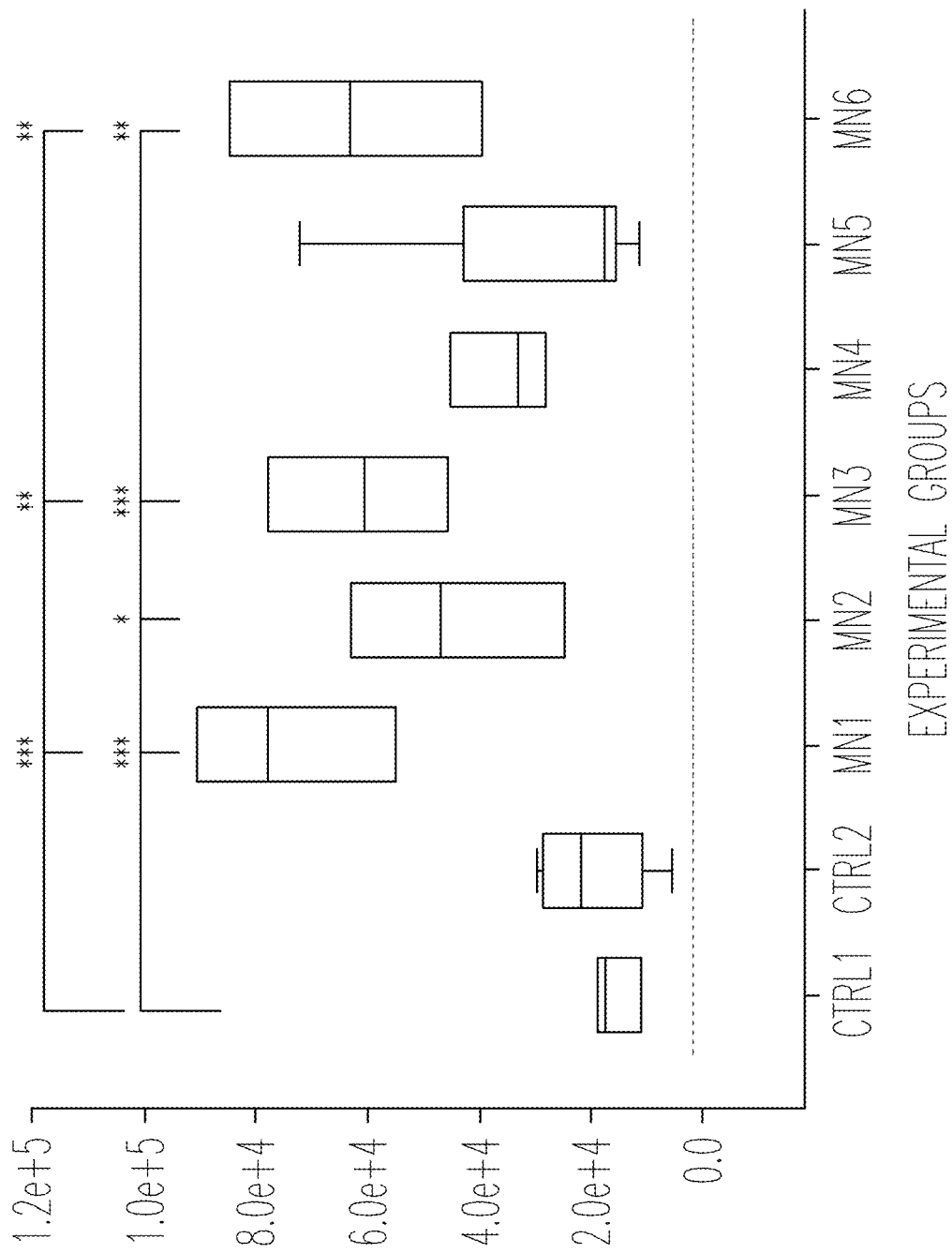
Figure 6E:
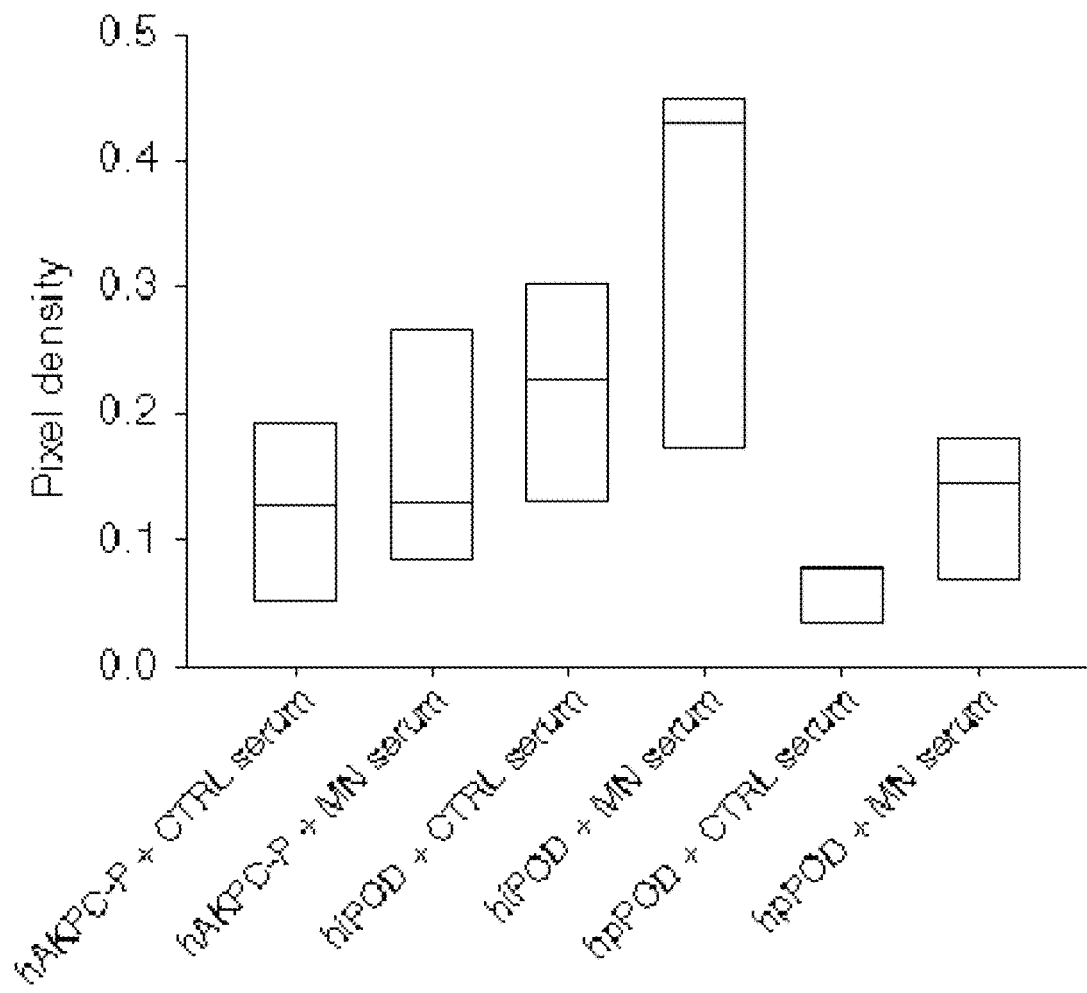
Figure 6F:
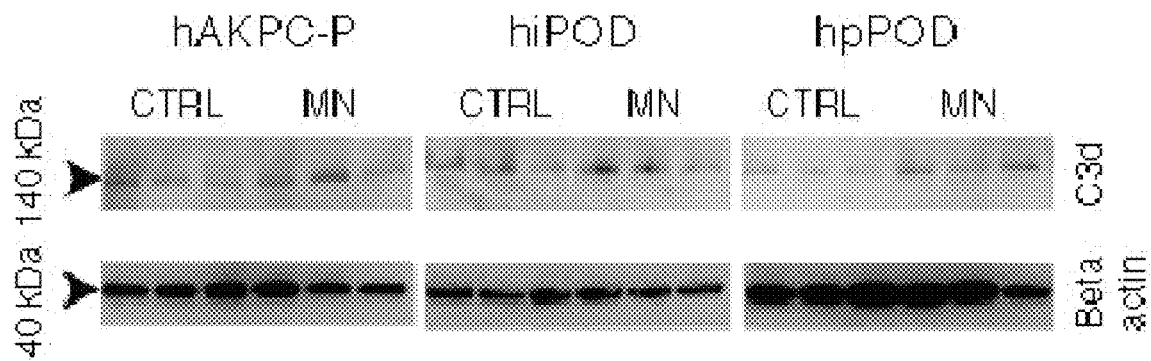
Figure 6G:
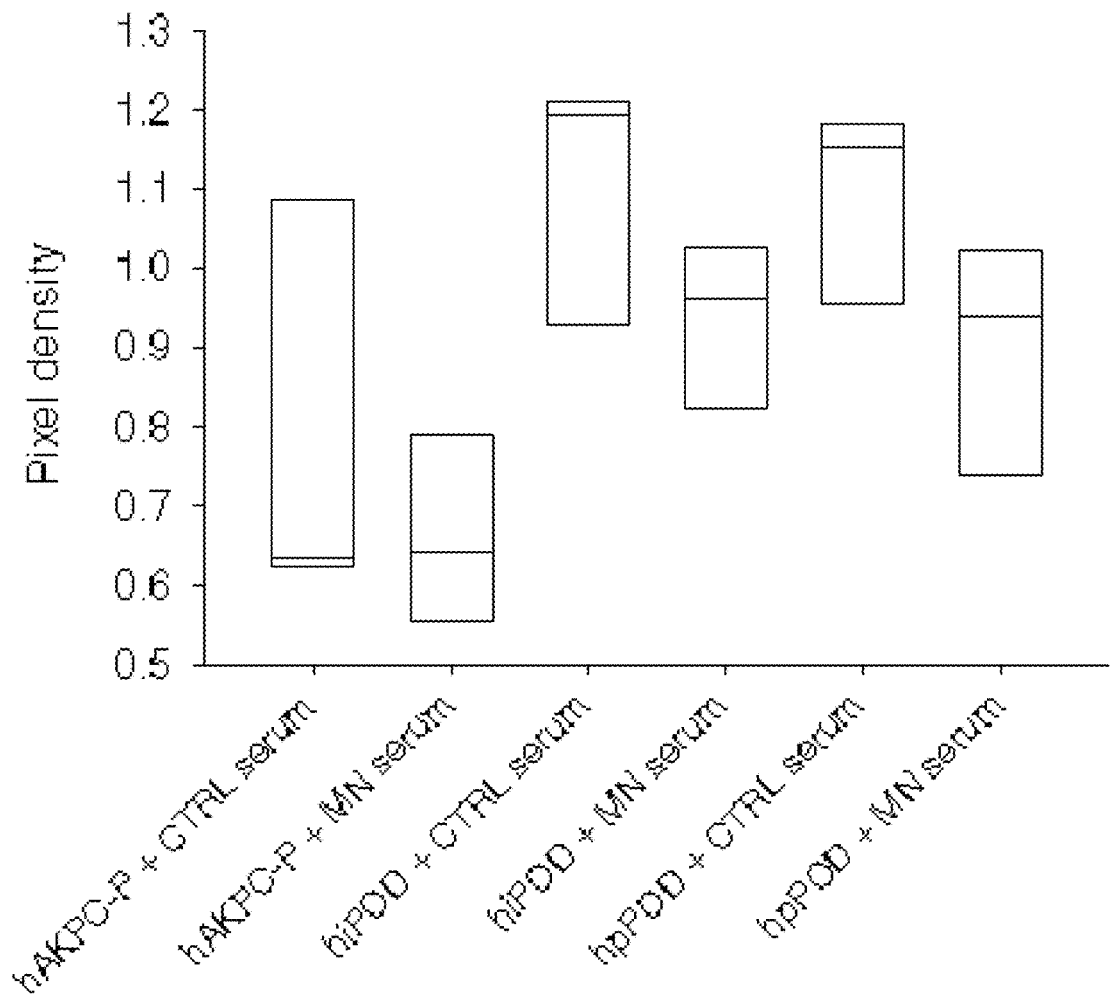
Figure 6H:
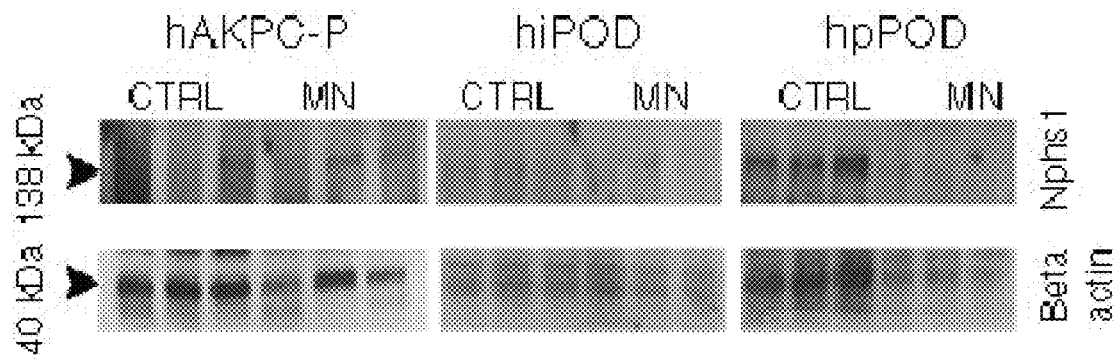

In MN, following autoantibody binding, several mechanisms are triggered in podocytes, like the complement signaling (54) that can lead to delocalization of nephrin with loss of the slit diaphragm structure and podocyte injury (55). Indeed, following exposure to MN serum, it was confirmed that there was an increase in the expression of C3d protein in the three podocyte lines that, although not significant, suggests an activation of the complement pathway consistent with the in vivo cascade signaling (54, 56) (FIG. 6E, F). Complement activation was paralleled by a decrease in nephrin compared to cells cultured with control (healthy) serum (FIG. 6G, H). To further characterize cellular response to MN serum, SNAIL expression was evaluated and confirmed its increase in the nuclear region following MN exposure for 24 h. Interestingly, increase in SNAIL appears to be much more marked in hAKPC-P compared to hiPOD and could possibly explain the lower proteinuria levels detected in the hiPOD chips (FIG. 5G). These data, taken together, demonstrate that within the chip it is possible to explore disease mechanisms and cascade signaling.

While the podocyte is the initial target of autoantibodies in MN, endothelial cells in the glomeruli of affected patients also show signs of injury (57). To test whether the same occurs in GOAC exposed to MN serum, WGA expression was measured in endothelial cells and found that the expression declined at 24 h after exposure, a phenomenon that did not occur in the presence of control sera. Altogether, these data validate the system as a model to study MN, and other disease, pathophysiology in vitro.

GOAC Response Specificity to Sera from Various CKD

Figure 7A:
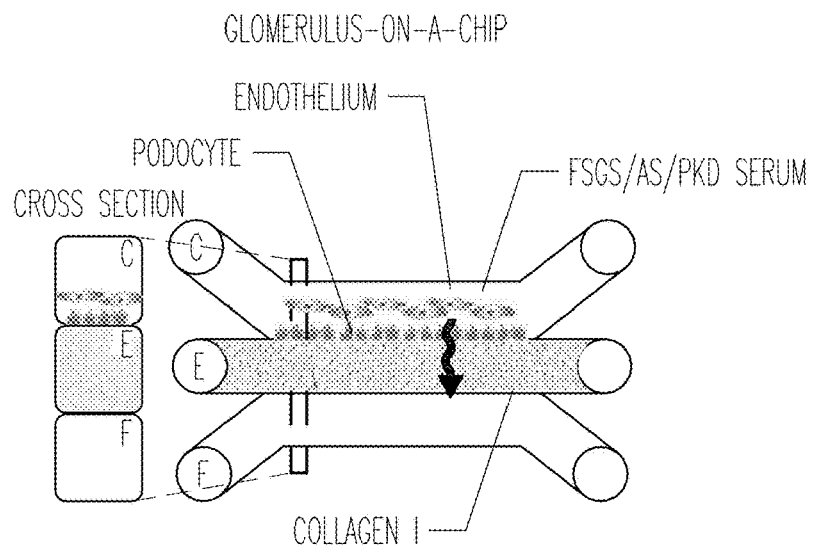
FIGS. 7A-D. Validation of the hAKPC-P GOAC system as a diagnostic and drug screening platform. A Scheme of GOAC albumin permselectivity assay and exposure to serum from patients affected by FSGS, AS, and PKD. Following a 24 h incubation with media supplemented with 0.5% serum from healthy individuals (CTRL1 and CTRL2) or CKD patients, albumin-FITC is applied to channel C and flow-through presents in channel F. B Box plot graph of fluorescein absorbance in filtrate after 60 min following 24 h incubation with serum from healthy individuals (CTRL1 and CTRL2), patients affected by FSGS (FSGS1, FSGS2, and FSGS3), AS, and PKD (PKD1, PKD2, and PKD3). As expected, no statistically significant differences were detected among groups. Number of replicates for chips used in B as follow: CTRL1: #7; CTRL2: #8; FSGS1: #9; FSGS2: #3; FSGS3: #4; AS: #4; PKD1: #5; PKD2: #5; PKD3: #5. C Scheme of GOAC albumin permselectivity assay and exposure to healthy or MN serum with or without α-MSH. Following a 24 h incubation with media supplemented with 0.5% serum from healthy individuals (CTRL2), MN patient (MN3) or MN patient (MN3)+α-MSH, albumin-FITC is applied to channel C and flow-through presents in channel F.
Figure 7B:
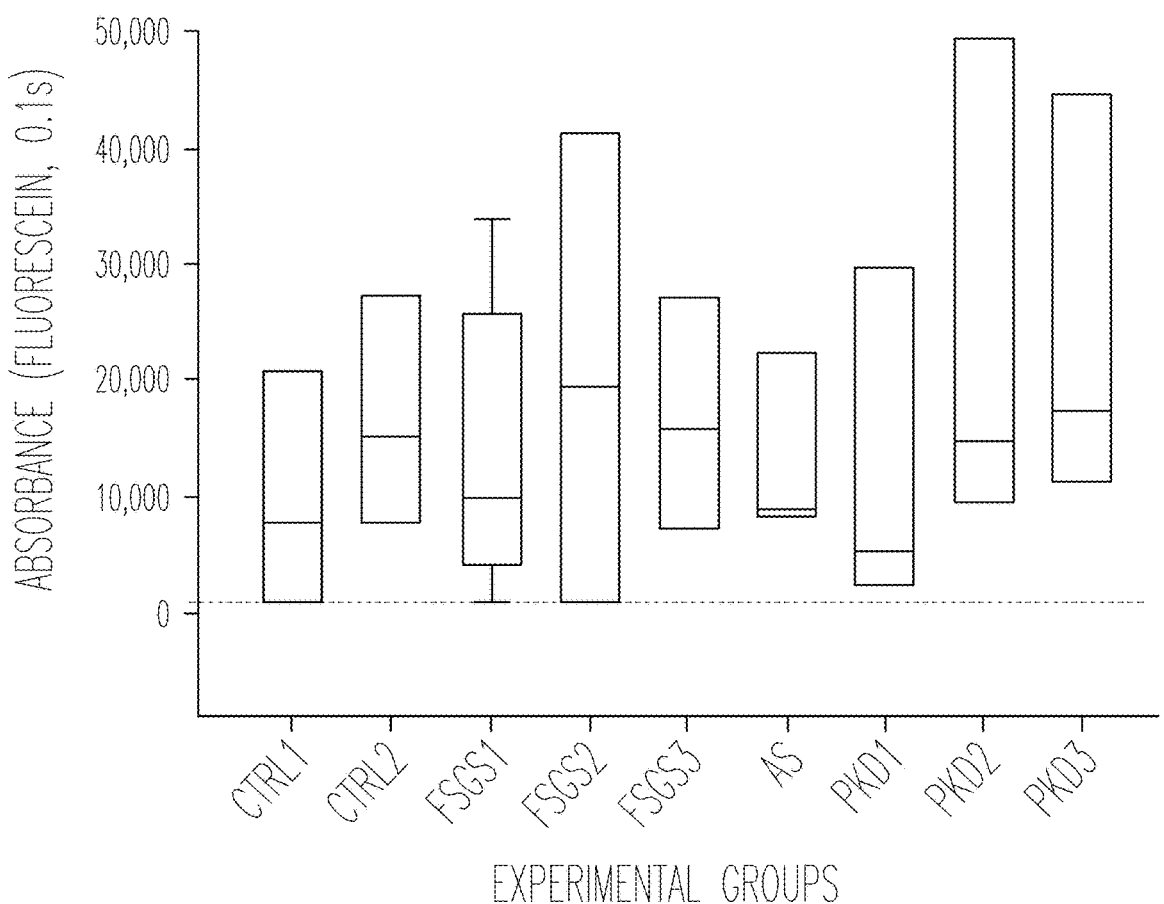

To exclude that albumin leakage induced in GOAC by MN serum was due to an unselective response to serum from subjects affected by CKD, the chip was exposed to sera from individuals with AS, polycystic kidney disease (PKD), or FSGS. Both AS and PKD are due to a primary renal defect and circulating factors in the serum are not thought to play a role in disease pathogenesis. While putative circulating factors have been described in FSGS, the sera included in the experiments were obtained from individuals with disease remission; therefore, these factors (if present) were not enough to induce proteinuria in vivo. As shown in FIG. 7A, B, it was found that serum from FSGS, AS, or PKD subjects did not trigger loss of permselectivity, further confirming specificity of albumin leakage induced by MN sera.

Modeling Response to Therapy in the GOAC Exposed to MN Sera

Figure 7C:
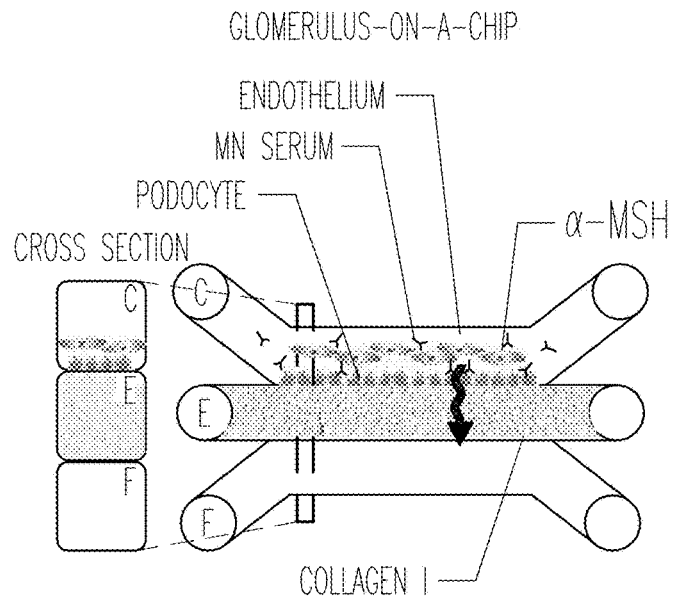
Figure 7D:
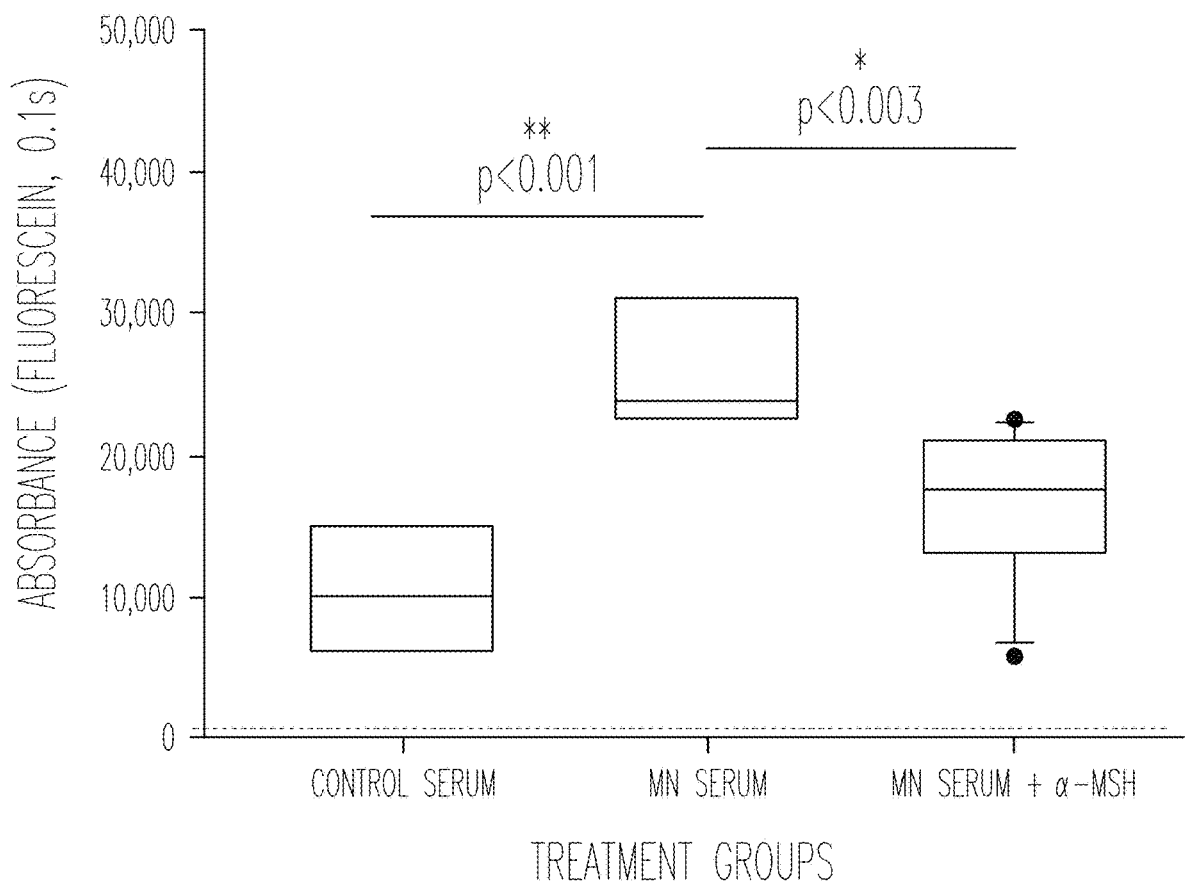

Building upon the previous results, the hypothesis that GOAC represents a unique platform for screening drugs targeting the GFB was evaluated. The GOAC was exposed to MN serum for 24 h in the presence or absence of α-melanocortin stimulating hormone (α-MSH). This hormone mimics the activity of the adrenocorticoid hormone (ACTH), clinically used in MN patients to reduce proteinuria (58). α-MSH main mechanism of action is through inhibition of RhoA inhibitor p190RhoGAP activity, which plays a role in the stabilization of podocyte stress fibers (59). It was found that, similarly to data obtained in vivo using ACTH (60), α-MSH prevented proteinuria elicited by MN serum (FIG. 7C, D) indicating that it acts downstream the formation of immune complexes on podocytes. These data demonstrate that GOAC responds to human nephrotoxic serum and nephroprotective treatment similarly to the in vivo human glomeruli.

Establishing a Model of Diabetic Nephropathy in the GOAC

Figure 8A:
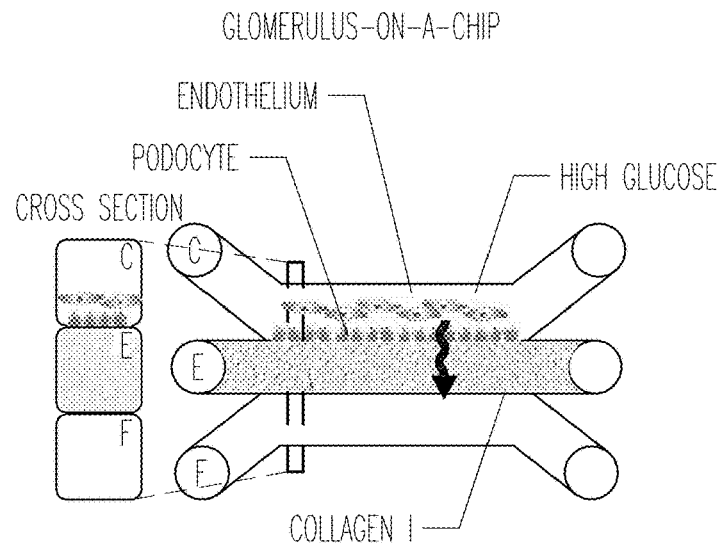
Figure 8B:
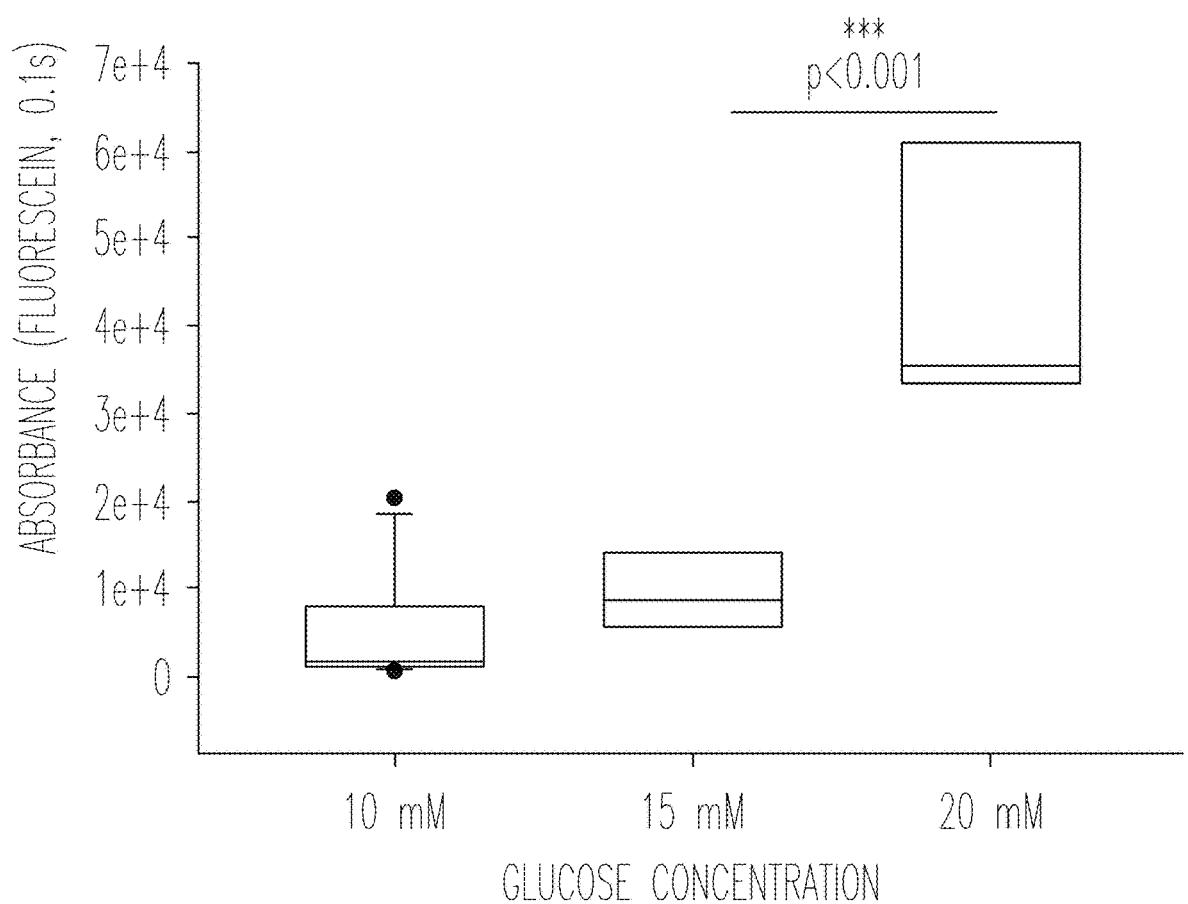
Figure 8C:
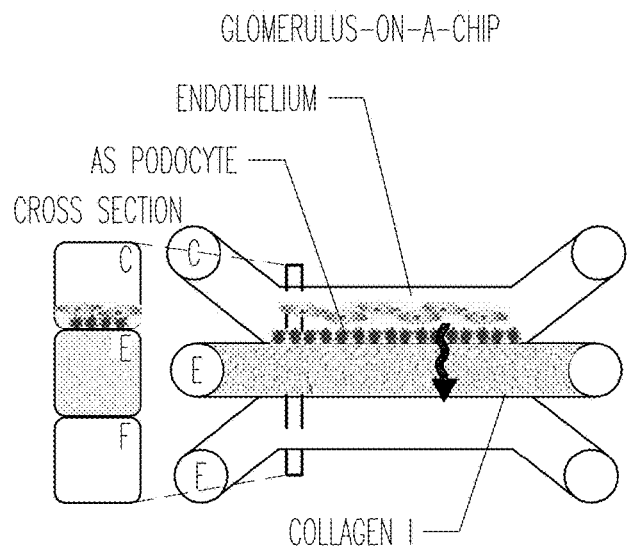
Figure 8D:
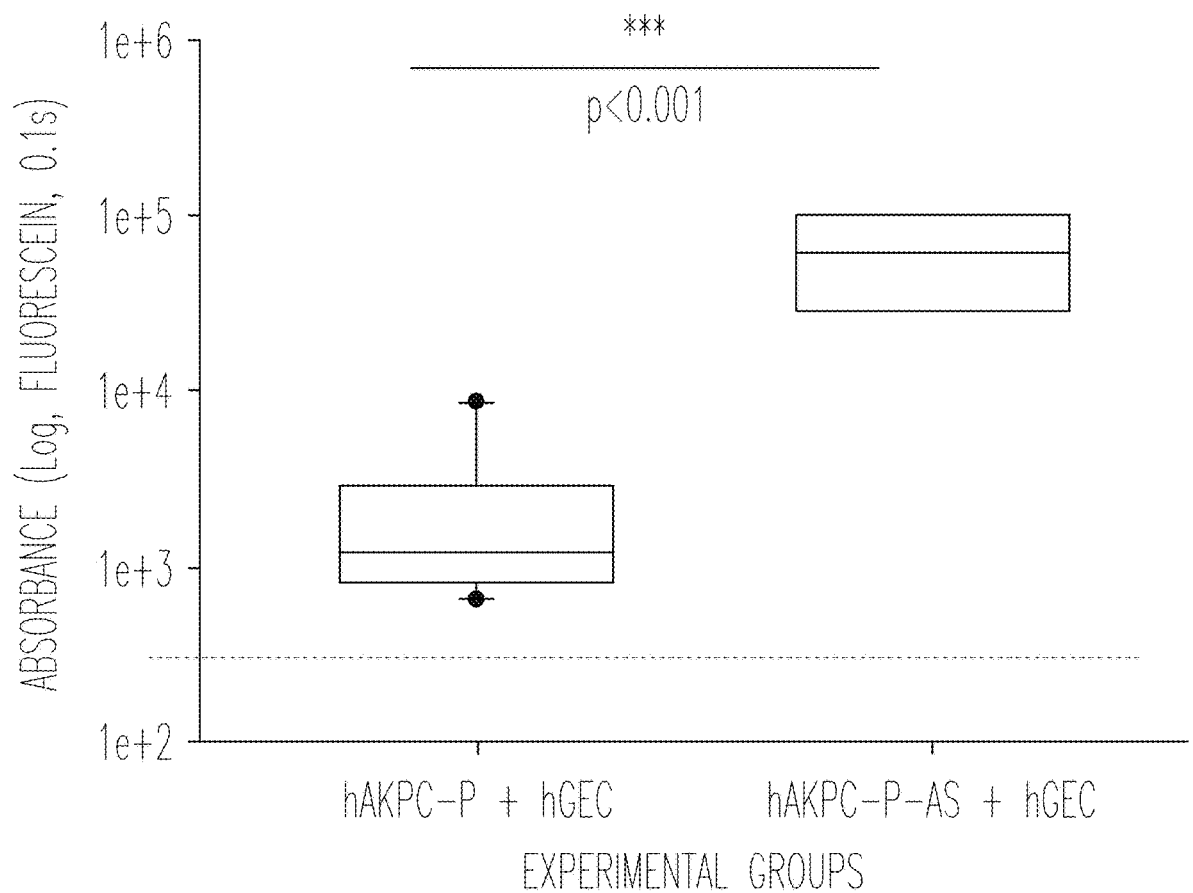

Hyperglycemia is recognized as a key initiation factor of ESRD in diabetic patients, which contributes to the increased albumin leakage across the GFB (61). High glucose has been shown in vitro to lead to podocyte damage (62, 63.) To test whether the system could replicate glucose-induced damage, GOAC was exposed to medium containing 10, 15, or 20 mM glucose and assessed its effect on permselectivity. After 72 h, the chips presented with a significant loss of albumin permselectivity compared to the control group (10 mM) or 15 mM (FIG. 8A, B).

Primary Podocyte Mutations Promote Albumin Leakage in GOAC

To test disease-modeling applications, a GOAC was generated using hAKPC-P derived from a patient affected by AS (AS-hAKPC-P). In AS, a mutation on COL4α3α4α5 genes leads to deposition of a defective GBM, leading to CKD and ESRD (26). As predicted, chips generated using AS-hAKPC-P exhibited a marked and statistically significant albumin leakage (FIG. 8C, D), while chips with podocytes from control individuals did not. Overall, these data document that GOAC can be used to model in vitro abnormalities in the GFB due to genetic abnormalities in podocytes.

Discussion

The data show that human podocytes and glomerular endothelial cells can be combined with the MIMETAS™ technology to create a functional GFB in vitro. These cells co-cultured in the GOAC maintain their phenotype and function for at least a month, allowing for long-term experiments. Compared to other proposed glomerular chips (20-22), the system presents significant differences and great advantages. The use of a chip devoid of any artificial membrane that separates layers of cells facilitates the correct interactions and crosstalk between cells as it is occurring in vivo. Seeded podocytes form slit diaphragm and endothelial cells form capillary-like structures, cellular features for a correct filtration activity of the glomerular barrier. The formation of a correctly assembled basement membrane containing specific glomerular extracellular proteins (like COL4α3α4α5 and LAM5α2β1γ) was shown. The resemblance of the GFB structure in vitro was demonstrated, thus showing that the absence of synthetic membrane could be essential for the correct assembly of the GFB.

The filtration of inulin and the retention of albumin within the GOAC was demonstrated, thus resembling the human GFB. This successful reconstruction of the GFB by the instant chips can be explained not only by the absence of a synthetic membrane between the cell layers and by the correct assembly of the GBM, but also by the choice of the podocyte source. hAKPC-P present phenotype and function very similar to primary podocytes, and they can be efficiently differentiated in large scale without the use of any immortalization or laborious protocols, as previously shown (25). The system was also shown to be superior compared to transwell systems built following the same protocol, thus further highlighting the strength of the instant platform. The data also indicate that immortalized podocytes present some limitations in studies of permselectivity in response to damage as shown in FIGS. 5 and 6.

Of major relevance for research on glomerular diseases, it was demonstrated that the GOAC responded to chemical injury with PAN, glucose-induced damage, and nephrotoxic serum from MN patients similarly to in vivo glomeruli. Upon deposition of IgG on the podocytes, the GFB exposed to sera from MN lost permselectivity to albumin to an extent that was proportional to the levels of anti-PLA2R IgG and severity of proteinuria measured in vivo in the same patients. Altogether, these data demonstrate that this system represents a unique platform to study the pathophysiology of glomerular diseases in a manner that, differently from previously proposed works, allows to study (1) changes in 3D conformation of podocytes, endothelial cells, and GBM; (2) abnormalities in their function; and (3) the crosstalk among them. The ability to separately manipulate the three elements of the GFB in the GOAC offers the opportunity to test mechanisms of glomerular diseases by selectively targeting—on a large scale—genes or molecules in the cultured podocytes and/or endothelial cells. The strong association between functional data in the GOAC and in vivo renal parameters also indicates that this system can be used as a platform to identify new biomarkers of glomerular injury in response to various stimuli and to test glomerular toxicity of new compounds.

The fact that a podocyte-targeting drug like α-MSH, clinically used to reduce proteinuria in MN patients, prevented the proteinuric effects of MN sera in the GOAC is indeed remarkable. This result supports the use of the GOAC for drug screening studies, a major unmet need for research in nephrology. The system, devoid of synthetic membrane but with functional GBM, allows real doses of drugs to be tested; they can be added directly into channel C without worries that synthetic membrane (with pore size bigger than what is present in the in vivo GBM and lack of the morphology represented by the curvature of the vasculature (22)) could improperly absorb/retain different molecules, compromising evaluation of efficacy and toxicity of the tested compound. Moreover, while organoids have proven to be a key tool for understanding kidney development and for disease modeling, their usefulness for drug screening is still unclear due to the (1) potential incomplete differentiation of the renal structures, (2) difficult diffusion of drugs within the 3D tissue as well as the (3) difficult assessment of proteinuria in their system (64).

The instant system also offers a unique prospect for disease-modifying studies. Here, the GOAC was validated using podocytes derived from a patient affected of AS ((26), male X-linked, missense mutation, p.Gly370Glu). It was demonstrated that this Alport-GOAC shows improper filtration; thus, it can serve as a platform for studies of personalized medicine. Amniotic fluid can be collected from Alport patients carrying the natural mutation, thus accurately recapitulating the human disease. Most importantly, the derivation of multiple cell lines from patients affected by different mutations of the same disease guarantees representation of disease heterogeneity in real time in a dynamic system, which is not possible for example in mice studies. Even if iPs technology presents this advantage too, the derivation of podocytes from iPs requires immortalization and laborious induction protocols, while hAKPC-P differentiation is an easy and fast process with minimal cell manipulation (25).

In conclusion, this chip represents a transformative system that mimics the human renal filtration barrier and is an ideal tool to study glomerular disease mechanisms and drug screening. Chips generated with diseased podocyte lines will increase the understanding of the cellular and molecular mechanisms responsible for glomerular injury and podocyte loss and will advance the design and evaluation of therapeutics strategically targeted to the glomerulus, thus ultimately benefiting patients affected by CKD and renal failure.

BIBLIOGRAPHY

1. Levin, A. et al. Global kidney health 2017 and beyond: a roadmap for closing gaps in care, research, and policy. Lancet 390, 1888-1917 (2017).
2. Metcalfe, W. How does early chronic kidney disease progress? A background paper prepared for the UK Consensus Conference on early chronic kidney disease. Nephrol. Dial. Transpl. 22(Suppl 9), ix26-ix30 (2007).
3. Suh, J. H. & Miner, J. H. The glomerular basement membrane as a barrier to albumin. Nat. Rev. Nephrol. 9, 470-477 (2013).
4. Scott, R. P. & Quaggin, S. E. Review series: the cell biology of renal filtration. J. Cell Biol. 209, 199-210 (2015).
5. D'Agati, V. D. Growing new kidneys from embryonic cell suspensions: fantasy or reality? J. Am. Soc. Nephrol. 23, 1763-1766 (2012).
6. Morizane, R. & Bonventre, J. V. Kidney organoids: a translational journey. Trends Mol. Med. 23, 246-263 (2017).
7. Shi, Y., Inoue, H., Wu, J. C. & Yamanaka, S. Induced pluripotent stem cell technology: a decade of progress. Nat. Rev. Drug Discov. 16, 115-130 (2017).
8. Bhatia, S. N. & Ingber, D. E. Microfluidic organs-on-chips. Nat. Biotechnol. 32, 760-772 (2014).
9. Agarwal, A., Goss, J. A., Cho, A., McCain, M. L. & Parker, K. K. Microfluidic heart on a chip for higher throughput pharmacological studies. Lab Chip 13, 3599-3608 (2013).
10. Beckwitt, C. H. et al. Liver 'organ on a chip'. Exp. Cell Res. 363, 15-25 (2018).
11. Kim, H. J., Huh, D., Hamilton, G. & Ingber, D. E. Human gut-on-a-chip inhabited by microbial flora that experiences intestinal peristalsis-like motions and flow. Lab Chip 12, 2165-2174 (2012).
12. Kim, H. J. & Ingber, D. E. Gut-on-a-chip microenvironment induces human intestinal cells to undergo villus differentiation. Integr. Biol. (Camb.) 5, 1130-1140 (2013).
13. Huh, D. et al. Reconstituting organ-level lung functions on a chip. Science 328, 1662-1668 (2010).
14. Huh, D. et al. A human disease model of drug toxicity-induced pulmonary edema in a lung-on-a-chip microdevice. Sci. Transl. Med. 4, 159ra147 (2012).
15. Moreno, E. L. et al. Differentiation of neuroepithelial stem cells into functional dopaminergic neurons in 3D microfluidic cell culture. Lab Chip 15, 2419-2428 (2015).
16. Kelly, E. J. et al. Innovations in preclinical biology: ex vivo engineering of a human kidney tissue microperfusion system. Stem Cell Res. Ther. 4(Suppl. 1), S17 (2013).
17. Jang, K. J. et al. Human kidney proximal tubule-on-a-chip for drug transport and nephrotoxicity assessment. Integr. Biol. (Camb.) 5, 1119-1129 (2013).
18. Hoppensack, A. et al. A human in vitro model that mimics the renal proximal tubule. Tissue Eng. Part C Methods 20, 599-609 (2014).
19. Wilmer, M. J. et al. Kidney-on-a-Chip technology for drug-induced nephrotoxicity screening. Trends Biotechnol. 34, 156-170 (2016).
20. Zhou, M. et al. Development of a functional glomerulus at the organ level on a chip to mimic hypertensive nephropathy. Sci. Rep. 6, 31771 (2016).
21. Wang, L. et al. A disease model of diabetic nephropathy in a glomerulus-on-achip microdevice. Lab Chip 17, 1749-1760 (2017).
22. Musah, S. et al. Mature induced-pluripotent-stem-cell-derived human podocytes reconstitute kidney glomerular-capillary-wall function on a chip. Nat. Biomed. Eng. 1, 0069 (2017).

23. Vulto, P. et al. Phaseguides: a paradigm shift in microfluidic priming and emptying. Lab Chip 11, 1596-1602 (2011).

24. Huh, D. et al. Microfabrication of human organs-on-chips. Nat. Protoc. 8, 2135-2157 (2013).

25. Da Sacco, S. et al. A novel source of cultured podocytes. PLoS ONE 8, e81812 (2013).

26. Kashtan, C. E. et al. Alport syndrome: a unified classification of genetic disorders of collagen IV α345: a position paper of the Alport Syndrome Classification Working Group. Kidney Int. 93, 1045-1051 (2018).

27. Shankland, S. J., Pippin, J. W., Reiser, J. & Mundel, P. Podocytes in culture: past, present, and future. Kidney Int 72, 26-36 (2007).

28. Saleem, M. A. et al. A conditionally immortalized human podocyte cell line demonstrating nephrin and podocin expression. J. Am. Soc. Nephrol. 13, 630-638 (2002).

29. Patrakka, J. et al. Expression and subcellular distribution of novel glomerulus associated proteins Dendrin, Ehd3, Sh2d4a, Plekhh2, and 2310066E14Rik. J. Am. Soc. Nephrol. 18, 689-697 (2007).

30. Satchell, S. C. et al. Conditionally immortalized human glomerular endothelial cells expressing fenestrations in response to VEGF. Kidney Int. 69, 1633-1640 (2006).

31. Satchell, S. C. & Braet, F. Glomerular endothelial cell fenestrations: an integral component of the glomerular filtration barrier. Am. J. Physiol. Ren. Physiol. 296, F947-F956 (2009).

32. Dane, M. et al. A microscopic view on the renal endothelial glycocalyx. Am. J. Physiol.-Ren. Physiol. 308, F956-F996 (2015).

33. Singh, A. et al. Glomerular endothelial Glycocalyx constitutes a barrier to protein permeability. J. Am. Soc. Nephrol. 18, 2885-2893 (2007).

34. Cosgrove, D., Kalluri, R., Miner, J. H., Segal, Y. & Borza, D. B. Choosing a mouse model to study the molecular pathobiology of Alport glomerulonephritis. Kidney Int. 71, 615-618 (2007).

35. Abrahamson, D. R. Role of the podocyte (and glomerular endothelium) in building the GBM. Semin. Nephrol. 32, 342-349 (2012).

36. Funk, S. D., Lin, M. H. & Miner, J. H. Alport syndrome and Pierson syndrome: diseases of the glomerular basement membrane. Matrix Biol. 71-72, 250-261 (2018).

37. St John, P. L. & Abrahamson, D. R. Glomerular endothelial cells and podocytes jointly synthesize laminin-1 and -11 chains. Kidney Int. 60, 1037-1046 (2001).

38. Satchell, S. The role of the glomerular endothelium in albumin handling. Nat. Rev. Nephrol. 9, 717-725 (2013).

39. Ballermann, B. et al. Shear stress and the endothelium. Kidney Int. 54, S100-S108 (1998).

40. Vormann, M. et al. Nephrotoxicity and kidney transport assessment on 3D perfused proximal tubules. AAPS J. 20, 90 (2018).

41. Tojo, A. & Kinugasa, S. Mechanisms of glomerular albumin filtration and tubular reabsorption. Int J. Nephrol. 2012, 481520 (2012).

42. Human Albumin. Transfus. Med. Hemother. 36, 399-407 (2009). https://www.ncbi.nlm.nih.gov/pmc/articles/PMC2997295/?report=classic.

43. Menzel, S. & Moeller, M. J. Role of the podocyte in proteinuria. Pedia. Nephrol. 26, 1775-1780 (2011).

44. Borza, C. M., Chen, X., Zent, R. & Pozzi, A. Cell receptor-basement membrane interactions in health and disease: a kidney-centric view. Curr. Top. Membr. 76, 1063-5823 (2015).

45. Sturgeon, S. C., Sam, A. D. & Law, W. R. Rapid determination of glomerular filtration rate by single-bolus inulin: a comparison of estimation analyses. J. Appl. Physiol. 84, 2154-2162 (1985).

46. Whiteside, C. I., Cameron, R., Munk, S. & Levy, J. Podocytic cytoskeletal disaggregation and basement-membrane detachment in puromycin aminonucleoside nephrosis. Am. J. Pathol. 142, 1641-1653 (1993).

47. Ronco, P. & Debiec, H. Pathophysiological advances in membranous nephropathy: time for a shift in patient's care. Lancet 385, 1983-1992 (2015).

48. Ronco, P. & Debiec, H. Membranous nephropathy: a fairy tale for immunopathologists, nephrologists and patients. Mol. Immunol. 68, 57-62(2015).

49. Tuma, P. L. & Hubbard, A. L. Transcytosis: crossing cellular barriers. Physiol. Rev. 83, 871-932 (2003).

50. Lawrence, M. G. et al. Permeation of macromolecules into the renal glomerular basement membrane and capture by the tubules. Proc. Natl Acad. Sci. USA 114, 11 (2017).

51. Beck, L. H. & Salant, D. J. Membranous nephropathy: from models to man. J. Clin. Invest. 124, 2307-2314 (2014).

52. Ronco, P. & Debiec, H. Pathogenesis of membranous nephropathy: recent advances and future challenges. Nat. Rev. Nephrol. 8, 203-213 (2012).

53. Beck, L. H. et al. M-type phospholipase A2 receptor as target antigen in idiopathic membranous nephropathy. N. Engl. J. Med. 361, 11-21 (2009).

54. Ronco, P. & Debiec, H. A podocyte view of membranous nephropathy: from Heymann nephritis to the childhood human disease. Pflug. Arch. 469, 997-1005 (2017).

55. Yuan, H. et al. Nephrin dissociates from actin, and its expression is reduced in early experimental membranous nephropathy. J. Am. Soc. Nephrol. 13, 946-956 (2002).

56. Lai, W. L. et al. Membranous nephropathy: A review on the pathogenesis, diagnosis, and treatment. J. Formos. Med Assoc. 114, 102-111 (2015).

57. Morita, M. et al. Glomerular endothelial cell injury and focal segmental glomerulosclerosis lesion in idiopathic membranous nephropathy. PLoS ONE 10, e0116700 (2015).

58. Filippone, E. J. et al. Adrenocorticotropic hormone analog use for podocytopathies. Int. Med. Case Rep. J. 9, 125-133 (2016).

59. Elvin, J. et al. Melanocortin 1 receptor agonist protects podocytes through catalase and RhoA activation. Am. J. Physiol. Ren. Physiol. 310, F846-F856 (2016).

60. Goldsmith, C. J. & Hammad, S. A review of the re-emergence of adrenocorticotrophic hormone therapy in glomerular disease, more than a drug of last resort? Clin. Kidney J. 8, 430-432 (2015).

61. Peng, H. et al. Simvastatin alleviates hyperpermeability of glomerular endothelial cells in early-stage diabetic nephropathy by inhibition of RhoA/ROCK1. PLoS ONE 8, e80009 (2013).

62. Li, C. & Siragy, H. M. High glucose induces podocyte injury via enhanced (pro)renin receptor-Wnt-β-catenin-snail signaling pathway. PLoS ONE 12, e89233 (2014). 9.

63. Susztak, K. et al. Glucose-induced reactive oxygen species cause apoptosis of podocytes and podocyte depletion at the onset of diabetic nephropathy. Diabetes 55, 225-233 (2006).

64. Kim, Y. K., Nam, S. A. & Yang, C. W. Applications of kidney organoids derived from human pluripotent stem cells. Korean J. Intern. Med. 33, 649-659 (2018).

65. Schlöndorff, D. & Banas, B. The mesangial cell revisited: no cell is an island. J. Am. Soc. Nephrol. 20, 1179-1187 (2009).

66. Vriend, J. et al. Screening of drug-transporter interactions in a 3D microfluidic renal proximal tubule on a chip. AAPS J. 20, 87 (2018).

2019 Automated microfluidic cell culture of stem cell derived dopaminergic neurons, Scientific Reports, Khalid I. W. Kane et al.

2019 Tubuloids derived from human adult kidney and urine for personalized disease modeling, Nature Biotech, Frans Schutgens et al.

2019 Differentiation of the human liver progenitor cell line (HepaRG) on a microfluidic-based biochip, Advanced Science, Mi Jang et al.

2018 3D Cultures of Parkinson's Disease-Specific Dopaminergic Neurons for High Content Phenotyping and Drug Testing, Advanced Science, Bolognin et al.

2018 Perfused 3D angiogenic sprouting in a high-throughput in vitro platform. Angiogenesis. Van Duinen et al.

2018 A perfused human blood-brain barrier on-a-chip for high-throughput assessment of barrier function and antibody transport. Fluids Barriers CNS, Wevers et al.

2018 Nephrotoxicity and Kidney Transport Assessment on 3D Perfused Proximal Tubules. AAPS J., Vormann et al.

2018 Screening of Drug-Transporter Interactions in a 3D Microfluidic Renal Proximal Tubule on a Chip. AAPS J., Vriend et al.

2018 Combining Extracellular miRNA Determination with Microfluidic 3D Cell Cultures for the Assessment of Nephrotoxicity: a Proof of Concept Study. AAPS J., Suter-Dick et al.

2018 Mechanistic Investigations of Diarrhea Toxicity Induced by anti-HER2/3 Combination Therapy, Mol. Cancer Ther, Moisan et al.

2018 Study of melatonin-mediated effects on various hepatic inflammatory responses stimulated by IL-6 in a new HepG2-on-a-chip platform. Biomedical Microdevices. Jang et al.

2018 Acoustic Characterization of a Vessel-on-a-Chip Microfluidic System for Ultrasound-Mediated Drug Delivery. IEEE Trans Ultrason Ferroelectr Freq Control, Beekers et al.

2018 Three-dimensional (3D) tetra-culture brain on chip platform for organophosphate toxicity screening, Sci Reports, Koo et al.

Example II—Human Kidney Cell Isolation/Method of Isolation of Kidney Cells from Whole Human Kidneys Introduction Isolation of kidney cells, including glomeruli and glomerular cells from mammalian species to study glomerular filtration barrier, basement membrane, glomerular injury, and cellular metabolism has been the focus of many previous investigations (1-4). Using small experimental animal models, such as mice (5-6), rats (7-9) and rabbits (10) methods have been developed for isolation of intact glomeruli, and glomerular endothelial cells (11-14), mesangial cells (15) and podocytes (16) with success, which have also been applicable to kidneys from primates and human origin (17-18). The various methods described so far for isolating glomeruli involve mechanical mincing of the renal cortex followed by enzymatic digestion in some cases using Collagenase type I (5) or exclusively a sieving method (19-21). To retrieve the glomerular cells several different methods have been described: 1) direct culture of isolated glomeruli in conditioned media allowing the cells to migrate and proliferate (22), 2) enzymatic digestion of isolated glomeruli (5-6), and 3) sonication of isolated glomeruli to obtain single cells (18). These methods work variably and relatively efficiently specifically on fresh kidneys. Derivation of viable human kidney cells from discarded non-transplantable kidneys is relatively more challenging due to long ischemia times often associated with obtaining human tissue, and methods to isolate large quantities of viable renal cells from whole human kidneys are lacking.

Other methods exist, including injection of iron oxide (Dynabeads) (2,6), which get stuck in the glomeruli for magnetic isolation. This applicability of this procedure towards human kidneys is limited due to the need of perfusion and a patent vasculature. Kidneys not found suitable for transplantation for the large part may have hemorrhaging, extensive fibrosis, and vascular damage, thus making efficient perfusion difficult if not impossible, Materials and Methods/Results and Discussion A novel method for the isolation of kidney primary cells from human whole kidneys (adult and neonatal—younger than 6 months old) that are considered not viable for transplantation but devoid of renal defects has been developed (applicable to kidneys viable for renal transplantation as well). The novelty of the current invention lies in the ability to isolate a large number of cells (using two different approaches based on the type of cells isolated and described in details below) and generating large batches of various renal cells (podocytes, glomerular endothelial cells, mesangial cells, tubular cells, endothelial cells) that originate from the same donor. Isolation of a large amount ($1-5\times10^9$) viable and well characterized human kidney cells (including but not limited to podocytes, mesangial cells, glomerular endothelial cells and proximal tubular cells) is of paramount importance for the ability of scientists and industry alike to perform in vitro studies on non-manipulated cells of primary origin, among other reasons. The same methodology can be applied to kidneys from donors affected by various renal diseases including but not limited to diabetic nephropathy, genetic diseases, focal segmental glomerulus sclerosis, cardiovascular diseases, polycystic kidney diseases among others.

A comprehensive and improved method for the isolation of kidney primary cells has been developed from human whole kidneys (adult and neonatal—younger than 6 months old) that are considered not viable for transplantation but devoid of renal defects. The novelty of the current invention lies in the ability to isolate a significantly large number of viable cells (using two different approaches based on the type of cells isolated and described in details below) and generating large numbers of batches of various renal cells (podocytes, glomerular endothelial cells, mesangial cells, tubular cells, endothelial cells) that originate from the same donor, previously not reported. The novelty of this isolation method for glomerular cells involves a short-term culture of isolated glomeruli before further manipulation, which provides cells time to recover from vigorous digestion processes. Below is a list of all the improvements:

the combination of Collagenase I, collagenase IV and dispase at the given concentrations for the digesting solution the optimal ratio of digesting solution per gr of tissue for optimal digestion adding warm digesting solution during the mincing process to help reduce incubation time in water bath, thus ensuring better cell survival the addition of HEPES, DNAse, primocin, and human serum to the PBS washing solution following digestion (to maintain pH balance and improve cell survival/viability and prevent cell clumping and sticking to plastic surfaces, thus loss of yield)

the specification regarding donor kidney age and the combination of collagenase I digestion and sieving for glomeruli extraction.

Note: Other published methods, especially for rat and human, use only mincing and sieving to obtain glomeruli. The use of only mechanical digestion does not properly break down the kidney and leaves behind large chunks making it difficult to sieve and isolate glomeruli. Thus, by adding enzymatic digestion and incubating the tissue based on a specific time and specific sieving size in accordance to age (adult or neonate) of the donor one can obtain improved yield of viable glomeruli.

Seeding of glomeruli versus immediate enzymatic digestion for better cell recovery prior to sorting. Seeding allows tightly packed glomerular cells to come out. Digestion of glomeruli is difficult. Extensive digestion is needed making the cells less viable for sorting. During cell isolation if glomeruli are not properly digested, isolation of podocytes or glomerular endothelial cells will also yield whole glomeruli in the positive cell collection.

Double sorting of cells (proximal tubular cells and glomerular endothelial cells, podocytes) to ensure purity of the population.

The same methodology can be applied to kidneys from donors affected by various renal diseases including but not limited to diabetic nephropathy, genetic diseases, focal segmental glomerulus sclerosis, cardiovascular diseases, polycystic kidney diseases among others.

Detailed Methods 1.1 Kidney Preparation—the Following Procedures are Performed on Ice Inside BSL2 Cabinet 1. Remove the kidney from the preservation solution, transfer it to a 150 mm petri dish (Corning, 430597) and begin to remove all visible fat and large renal vessels.
2. Prep another 150 mm petri dish with sterile gaze placed in it. Place the fat-free kidney on top of the gaze and remove the kidney capsule by making a small incision for a pocket between the kidney and capsule. Place a scissor inside the pocket and open and close the scissor to detach the capsule, once enough capsule has been detached peel off all the remaining capsule.
3. Slice the kidney in half by making a longitudinal incision from top to bottom of the kidney. Dissect out the renal pelvis and the medulla with scissor and scapula. Section the half in 4 pieces and further remove the medulla. Medulla has a darker color that is distinguishable from the cortex. Note: Neonate kidneys are lobular, be careful to not remove the cortex during dissection.
4. Weigh each section prior to the mechanical and enzymatic digestion.

2.0 Mechanical and Enzymatic Digestion:
for cortical cells: 2.1 (neonatal and adult), 2.2
for glomeruli: 2.3a (neonatal), 2.3b (adult), 2.4

2.1 Mechanical and Enzymatic Digestion for Cortical Cells From Whole Tissue

1. Prepare and pre-warm the digesting solution for total cortical digestion prepared as follows: dissolve collagenase type I (200 U/ml) (Worthington, c #LS004197), collagenase IV (200 U/ml) (Worthington, c #LS004189) and dispase (2.4 U/ml) (Gibco, c #17105041), 10 mM HEPES in RPMI1640 (Gibco, c #11875093) at 37° C. The collagenase solution will be used at a ratio of 20 ml/gr of minced tissue. Note: Tissue amount per collagenase solution was determined by trial and error, this method provided the most efficient amount of solution to use per tissue weight. A large amount of tissue is obtained after digestion of the kidney and this concentration is the least to use per tissue weight. If one uses less volume of collagenase solution per gram of tissue, the tissue may not digest properly. This volume also allows the tissue to be mixed properly for digestion.

2. After kidney dissection is complete, a portion of cortical tissue will be placed on a 100 mm tissue culture dish (Corning, c #430167) and minced with the use of scissors and surgical blade for about 15-20 minutes at room temperature. In order to help the mechanical mincing of the tissue, 2-3 ml of warm digestion solution is added to the tissue at this time. Once the mincing process is over (15-20 minutes), the tissue will be equally divided in 50 ml conical tubes (based on the initial grams of tissue). The collagenase solution is used at a ratio of 20 ml/gr of minced tissue thus roughly 2 gr of tissue/tube with 40 ml of collagenase solution will be prepared.

3. Incubate the tubes at 37° C. for 40-45 minutes in water bath with constant shaking at a speed of 200 RPM.

4. The lysate is filtered through a 100 μm cell strainer (Corning, c #352360) (multiple strainers can be used to filter the whole lysate). A syringe plunger (of a 20 ml syringe) is used to help break and push undigested tissue through the filter. Keep the flow through each time. To help unclog the filters and prevent cells from clumping, the filters are repeatedly washed with PBS containing DNAse1 (Deoxyribonuclease II from porcine spleen Type IV, lyophilized powder, 2,000-6,000 Kunitz units/mg protein, D4138 Sigma-Aldrich) 20,000 units/500 ml of PBS to help prevent clumping of cells and 0.2% Primocin (Invivogen, c #ant-pm-1). As the filtering process goes, the 50 ml tubes containing the filtered lysates are placed on ice until further processing (30 minutes to complete the filtering process).

5. The 50 ml tubes containing the filtered cortical digestion cell lysates are spun at 1500 rpm (~300 g) for 10 minutes and the pellets are combined together and re-suspended in 50 ml fresh PBS1× before cell counting.

6. Cells are counted using the digital Countess II Automated Cell Counter (Thermo Fisher Scientific) to assess cell viability following manufacturer protocol.

7. A portion of the cells (this is arbitrary, depending on how many cells one gets each time as tissues differ in yield, and how many cells one needs right away and wants to store) is frozen in cryovials using CryoStor cell preservation media (Sigma, C2874-100ML) (600,000 live cells/0.5 ml media/vial or $1.2 \times 10^6$ cells/ml). Cryovials are transferred to a storage box placed on dry ice and, upon filling, the box is immediately transferred to a −80° C. freezer and subsequently transferred (within a week) to liquid nitrogen for later processing or further selection of the cells at a later stage (see section 3.0).

2.2 Total hKC (Human Kidney Cortical Cells) Digest Preparation and Culture Prior to Isolation 1. Digested tissue is pelleted and washed once with PBS supplemented with 1% Penicillin-Streptomycin (Gibco, c #15070063) and 0.2% Primocin (Invivogen, c #ant-pm-1). Wash is performed by adding 45 ml of solution to a cell pellet of up to 100 million cells in a 50 ml tube. Lightly vortex the cells for 20 seconds. Allow the cells to sit for 3 min and centrifuge at 1500 RPM (~300 g) for 10 min.
2. 5 million cells are plated per T75 tissue culture flasks (Corning #430641U) and 15 ml of media is added (RPMI (Gibco, c #11875093), 5% FBS (Gibco, c #26140079), 0.2% Primocin (Invivogen, c #ant-pm-1), and 1% Penicillin-Streptomycin (Gibco, c #15070063). After 2 days the media is replaced and the unattached cells are collected and passed through a 40 μm (Corning, c #352340) cell strainer to collect unattached whole glomeruli. The mesh is flipped over and washed down with media onto a new 150 mm tissue culture plate, and cells are processed as glomeruli cell isolation (see section 2.4). The passthrough contains cortical cells (devoid of whole glomeruli) is spun down and re-plated.
3. After additional 2-4 days the cells are prepped for podocyte, mesangial cell, and tubular cell isolation.
4. Media is collected out of the plates, and plates are washed down with PBS, media and wash are spun down for 5 min at 1500 RPM.
5. 37° C. warmed up enzymatic solution 1×TrypLE (Gibco, c #12605028) is added to the washed plates for 5 minutes at 37° C.
6. Plates are tapped lightly to detach cells and a 10 ml pipette is used to wash down cells up and down for 1 min. Solution is collected and 2% FBS is used to neutralize the solution. The solution is spun down for 5 min at 1500 RPM and the pellet is resuspended in PBS for cell count using Countess Cell Counter following manufacturer protocol. Equal proportion of trypan blue and resuspended cells are used to obtain a count on live/dead number of cells.

2.3a Mechanical and Enzymatic Digestion for Isolation of Glomeruli from Whole Tissue of Adult Kidney
1. Prepare Collagenase type I digestion solution (cI-DS) in RPMI-1640 medium at a concentration of (200 U/mL) and pre-warm to 37° C. in a water bath.
2. After kidney dissection is complete, a portion of cortical tissue will be placed on a 100 mm tissue culture dish (Corning, c #430167) and minced with the use of scissors and surgical blade for about 15-20 minutes at room temperature. Once the mincing process is over (15-20 minutes).
3. Transfer minced tissue to 50 mL conical tubes and re-suspend in the cI-DS at 20 mL/g of tissue with a maximum volume of 40 mL per tube.
4. Incubate the tubes at 37° C. for 30-35 minutes in water bath with constant shaking (Barnstead Lab-Line, MaxQ 7000) at a speed of 200 RPM.
5. Once the incubation and digestion are complete, pass the lysate through a 500 μm then 250 μm cell strainer mesh (Industrial Netting, c #WN0500-500, c #WN0250-250) sequentially 1 time each to remove large chunks of undigested tissue. Keep the flow through and wash the tube with fresh PBS to ensure complete transfer of the lysate each time.
6. (Optional): At this time multiple tubes with digested kidney lysate can be filtered and pooled into a single large container that can accommodate the total volume.
7. Pass the collected filtrate through 100 μm cell strainer once and wash the tube with fresh PBS to ensure complete transfer of the lysate. Keep the flow through to further isolate smaller glomeruli 100 μm). Large glomeruli (>100 μm) will collect on top of the 100 μm filter. Majority of the glomeruli will be in this fraction.
8. To collect the large glomeruli, invert the 100 μm filter and collect the glomeruli into a clean 50 mL conical tube by washing the filter with ice cold PBS multiple times until the filter is cleared of all tissue.
9. Check under microscope for purity, and, if necessary, repeat steps 7-8 for 1-3 additional times until pure glomeruli are obtained.
10. To harvest the smaller glomeruli 100 μm), pass the filtrate from Step 7 through a 40 μm cell strainer. The glomeruli will now collect on top of the 40 μm filter and tissue lysate smaller than 40 μm will pass through.
11. To collect the small glomeruli, invert the 40 μm filter and collect the glomeruli into a clean 50 mL Eppendorf tube by washing the filter with ice cold PBS multiple times until the filter is cleared of all tissue.
12. Check under microscope for purity, and if necessary, repeat steps 8-9 for 1-3 additional times until pure glomeruli are obtained.
13. Centrifuge the purified fractions for 8 min at 2000 RPM (·340×g) at 4° C. and decant the PBS without disturbing the pellet.
14. Plate harvested glomeruli into 150 mm tissue culture dishes in 25 mL of RPMI-1640 media supplemented with 5% FBS and 0.2% Primocin and culture 5-6 days before further processing.

2.3b Mechanical and Enzymatic Digestion for Isolation of Glomeruli from Whole Tissue of Neonatal Kidney
1. Prepare Collagenase type I digestion solution (cI-DS) in RPMI-1640 medium at a concentration of (200 U/mL) and pre-warm to 37° C. in a water bath.
2. After kidney dissection is complete, a portion of cortical tissue will be placed on a petri dish and minced with the use of scissors and surgical blade for about 15-20 minutes at room temperature. Once the mincing process is over (15-20 minutes).
3. Transfer minced tissue to 50 mL conical tubes and re-suspend in the cI-DS at 20 mL/g of tissue with a maximum volume of 40 mL per tube.
4. Incubate the tubes at 37° C. for 25-30 minutes in water bath with constant shaking at a speed of 200 RPM.
5. Once the incubation and digestion are complete, pass the lysate through a 100 μm cell strainer sequentially 2 times to remove large chunks of undigested tissue. Keep the flow through and wash the tube with fresh PBS to ensure complete transfer of the lysate each time.
6. Note: Glomerular size in the adult kidney is relatively larger compared to children or neonates (17). This reference talks about the large and small size of adult and child glomeruli and using different sieve sizes to isolate them. Neonate glomeruli are smaller than 100 μm. This method ensures obtaining the purest population of glomeruli without contamination of tubules or large undigested tissue.
7. (Optional): At this time multiple tubes with digested kidney lysate can be filtered and pooled into a single large container that can accommodate the total volume.
8. To harvest the smaller glomeruli (>40 μm), pass the filtrate from 5 through a 40 μm cell strainer. The glomeruli will now collect on top of the 40 μm filter and tissue lysate smaller than 40 μm will pass through.
9. To collect the glomeruli, invert the 40 μm filter and collect the glomeruli into a clean 50 mL Eppendorf tube by washing the filter with ice cold PBS multiple times until the filter is cleared of all tissue.

10. Check under microscope for purity, and if necessary, repeat steps 7-9 for 1-3 additional times until pure glomeruli are obtained.
11. Centrifuge the purified fractions for 8 min at 2000 RPM (~340×g) at 4° C. and decant the PBS without disturbing the pellet.
12. Plate harvested glomeruli into 150 mm tissue culture dishes in 15 mL of RPMI-1640 media supplemented with 5% FBS, 0.2% Primocin, and 1% antibiotics and culture for 5-6 days before further processing.

2.4 Glomeruli Culture Prior to Isolation
1. Isolated glomeruli in suspension either from total digest or primary digest are pelleted by centrifuge at 1800 RPM (~320 g) for 10 min.
2. Glomeruli are plated on T75 tissue culture flasks (Corning #430641U) and 15 ml of media is added (RPMI (Gibco, c #11875093), 5% FBS (Gibco, c #26140079), 0.2% Primocin (Invivogen, c #ant-pm-1), and 1% Penicillin-Streptomycin (Gibco, c #15070063). After 2 days the media is replaced, and the unattached glomeruli are spun down at 1500 RPM (~300 g) for 6 min and re-plated back onto on T75 tissue culture flasks.
3. The glomeruli are sorted out after day 5-6 days, based on the number of glomeruli that appeared to be attached. The media is collected from the plates and separately spun down, if there are visible glomeruli, and pelleted by centrifugation at 1500 RPM (~300 g). The pellet is disrupted with 4-5 ml of warmed 1×TrypLE (Gibco, c #12605028) for 10 min by pipetting up and down gently, check under light microscope every 5 min to make sure the glomeruli are not visible, do not pipette vigorously to obtain bubbles and do not exceed past 15 min as this may destroy the cells. 5 ml of PBS with 2% FBS is added to the sample and spun down. Then the sample is added to the processed plated for selection for podocytes, endothelial cells and mesangial cells.

3.0—Isolation of Renal Cells Based on Immunomagnetic Sorting
Podocytes: 3.1, 3.2
Mesangial cells: 3.3, 3.4
Proximal Tubular Cells: 3.5, 3.6
Glomerular Endothelial cells: 3.7, 3.8

From the glomerular fraction can be isolated podocytes, mesangial cells and glomerular endothelial cells; from the cortical fraction can be isolated proximal tubular cells, podocytes and mesangial cells. From the cortical cells other types of cells can be isolated (for example: kidney progenitors, distal tubules, other types of endothelial cells, pericytes, renal fibroblasts). The cortical cell digestion is a source of many different types of cells. There are no other sources of renal cells from where you can isolate, so many different types of cells. Another important observation: in the process provided herein the medulla is discarded as described above, but you can potentially store it or isolate from the medulla other types of kidney cells for different studies.

For the isolations described below, selection is performed using Miltenyi autoMACS sorter.

3.1 Selection for Podocytes
1. Pelleted and counted cells from either glomerular fraction or total cortical suspension are blocked with 2% human serum in PBS, 5 million cells per 100 ul for 15 min on ice.
2. Nephrin (2.5 ul/100 ul; Abcam #ab136894) is added to the samples and incubated for 35 min on ice.
3. Samples are washed with 5 ml of 2% human serum in PBS per 5 million cells and centrifuged at 1500 RPM for 5 min.
4. Secondary anti-rabbit beads are added (Miltenyi, #130-048-602) following manufacturer instructions.
5. After secondary samples are washed and magnetically separated with the autoMACS® Separator, using manufacturer instructions.
6. Sorted podocytes, around 2-5% of total cortical or glomeruli digested tissue are immediately frozen at between 300,000 and 600,000 live cells/vial/0.5 ml Cryostor 10 (Sigma Aldrich, #C2874-100ML).

3.2 Quality Control
After selection, seed 10,000 cell per well of an 8-well chamber slide (Fisher Scientific #08-774-26) for further QC testing. After 3 days of culture on chamber slides, cells are fixed with 4% paraformaldehyde (Santa Cruz Biotechnology c #sc-281692) for 10 min followed by washes with 1×PBS (Gibco, c #11875-093). Wells of interest were prepared for staining by blocking with 5% bovine serum albumin (Jackson ImmunoResearch Lab, c #001-000-162) in PBS for 30 minutes. Primary, secondary, and pre-conjugated antibodies were diluted in 2.5% BSA Jackson ImmunoResearch Lab. c #001-000-162). Primary antibodies were incubated at RT for 1 h; following serial washes, secondary antibodies were incubated at RT for 30 min. After a final series of washes in PBS, DAPI was applied (1:1000 in PBS; BD Pharmingen, c #564907), the wells were stored at 4° C. until imaged with a Leica DM5500 B Microscope System.

For flow cytometry analysis, cells were fixed in 4% paraformaldehyde (Santa Cruz Biotechnology c #sc-281692) for 10 min and permeabilized with 0.05% saponin for nuclear protein staining (WT1). Briefly, cells were blocked using 1× human IgG (Sigma c #12511) for 30 min and then stained with the specified antibodies, 1 µg/1×$10^6$ cells/100 µl IgG solution unless otherwise specified on the datasheet, for 1 h on ice. Cells were then washed twice in PBS and filtered immediately in a Corning™ Falcon™ Test Tube with Cell Strainer Snap Cap (Corning, c #352235) before sorting. Analysis was performed on a FACScanto machine using FACSDiva software. Unstained and single positive controls were used to perform area scaling, exclude autofluorescence, and perform fluorochrome compensation when needed. Cells were first gated based on forward and side scatters (FSC/SSC) to exclude dead cells and then gated for FSC-W/FSC-H and SSC-W/SSC-H to exclude potential duplets. Sorting gates were established based on the unstained population for each sample.

Culture After Selection Should be Limited to Avoid De-Differentiation.
QC: Cells are tested by immunofluorescence staining for:
Nephrin (glomerular marker, Abcam #ab136894): should be 80-95% positive
WT1 (podocyte marker): should be 80-95% positive
Vimentin (mesenchymal marker, Abcam #ab92547)—should be 80-95% positive
PDGFRB (Mesangial marker, R&D FAB1263F)—should be less than 5%.
Cytokeratin (epithelial marker, Abcam #ab6401)—should be less than 5%.
CD31 (endothelial marker, BioLegend #303116)—should be less than 5%.

3.3 Selection for Mesangial Cells
1. Perform first mesangial cells isolation from pelleted and counted cells from either glomerular fraction or cortical fraction. Use Miltenyi Order no: 130-105-278 CD140b-Biotin, PGFRB antibody and Miltenyi Order no: 130-105-637 secondary antibody for biotin follow manufacturer instructions. (Initially the cells are incubated with the primary antibody CD140b then washed, and labeled with secondary biotin, follow manufacture instructions.)
2. After secondary samples are washed and magnetically separated with the autoMACS® Separator, using manufacturer instructions.
3. Plate the isolated mesangial cells. Positive cells are counted using Countess Cell Counter. Isolated cells are seeded on a p100 tissue culture plates with mesangial cell media (ScienceCell #4201) and expanded for 3 passages (P3).
4. At P3, to isolate pure mesangial cells, perform the second isolation as described in steps 1-2. Note: Through trial and error it was concluded that a second isolation is needed to yield higher cell numbers and a pure mesangial population.
5. Freeze down cells. Positive cells are counted using Countess Cell Counter. Sorted mesangial cells are 100% CD140b+ and are immediately frozen at 600,000 live cells/vial in Cryostor 10 (Sigma Aldrich, #C2874-100ML).

3.4 Quality Control

After selection, seed 10,000 cell per well of an 8-well chamber slide (Fisher Scientific #08-774-26) for further QC testing. After 3 days of culture on chamber slides were fix with 4% paraformaldehyde (Santa Cruz Biotechnology c #sc-281692) for 10 min followed by a wash with 1×PBS. Wells of interest were prepared for staining by blocking with 5% bovine serum albumin (Jackson ImmunoResearch Lab, c #001-000-162) in PBS for 30 min Primary, secondary, and pre-conjugated antibodies were diluted in 2.5% BSA Jackson ImmunoResearch Lab. c #001-000-162). Primary antibodies were incubated at RT for 1 h; following serial washes, secondary antibodies were incubated at RT for 30 min. After a final series of washes in PBS, DAPI was applied (1:1000 in PBS; BD Pharmingen, c #564907), the wells were stored at 4° C. until imaged with a Leica DM5500 B Microscope System For flow cytometry analysis, cells were fixed in 4% paraformaldehyde (Santa Cruz Biotechnology c #sc-281692) for 10 min and permeabilized with 0.05% saponin for nuclear protein staining (WT1). Briefly, cells were blocked using 1× human IgG (Sigma c #12511) for 30 min and then stained with the specified antibodies, 1 µg/1×10$^6$ cells/100 µl IgG solution unless otherwise specified on the datasheet, for 1 h on ice. Cells were then washed twice in PBS and filtered immediately in a Corning™ Falcon™ Test Tube with Cell Strainer Snap Cap (Corning, c #352235) before sorting. Analysis was performed on a FACScanto machine using FACSDiva software. Unstained and single positive controls were used to perform area scaling, exclude autofluorescence, and perform fluorochrome compensation when needed. Cells were first gated based on forward and side scatters (FSC/SSC) to exclude dead cells and then gated for FSC-W/FSC-H and SSC-W/SSC-H to exclude potential duplets. Sorting gates were established based on the unstained population for each sample.

Cells are tested for:
  PDGFRB (Mesangial marker, R&D FAB1263F)—should be 80-95% positive
  Vimentin (mesenchymal marker, Abcam #ab92547)—should be 80-95% positive
  Cytokeratin (epithelial marker, Abcam #ab6401)—should be less than 5%
  CD31 (endothelial marker, BD Bioscience #561654): should be less than 5%
  Nephrin (glomerular marker, Abcam #ab136894): should be less than 5%
  EpCAM (Epithelial cell marker): should be less than 5%

3.5 Selection for Human Proximal Tubular (PT) Cells (Selected for CD10 and CD13)
1. Perform first PT cells isolation from pelleted and counted cells from cortical fraction by selecting for CD10+CD13+ cells. Label cells with primary antibodies: Use CD10-FITC (Miltenyi, cat. 130-093-448) and CD13-Biotin (Miltenyi cat. 130-103-757). PT cells are labeled with both antibodies following manufacturer's instructions.
2. 1st Isolate for CD10: After washing the sample, the anti-FITC multiSort Kit (Miltenyi, cat. 130-058-701) is used to select cells for CD10 expression first using anti-FITC beads (included in the kit).
3. After secondary samples are washed and magnetically separated with the autoMACS® Separator, using manufacturer instructions. After selection, cells are counted.
4. 2nd Isolate for CD13: A release agent is then added to remove the anti-FITC beads following kit's instructions. CD10+ cells are counted using Countess Cell Counter. CD10+ cells are next labeled with anti-Biotin microbeads (Miltenyi, cat. 130-105-637) and sorted for CD13.
5. After secondary samples are washed and magnetically separated with the autoMACS® Separator, using manufacturer instructions. After selection, cells are counted.
6. Plate the isolated PT cells in media. Positive cells are counted using Countess Cell Counter. Isolated cells are seeded on tissue culture plates with epithelial cell media and expanded for 3 passages (P3).
7. At P3, perform a second isolation to obtain pure PT by repeating the selecting for CD10+CD13+ cells as described in steps 1-5. Note: Through trial and error we came to the conclusion that a second isolation is needed to yield higher cell numbers and a purer yield.
8. Freeze down cells. Positive cells are counted using Countess Cell Counter. Sorted PT cells are 100% CD10+CD13+ and are immediately frozen at 600,000 live cells/vial in Cryostor (Sigma Aldrich, #C2874-100ML).

3.6 Quality Control

After selection, seed 10,000 cell per well of an 8-well chamber slide (Fisher Scientific #08-774-26) for further QC testing. After 3 days of culture on chamber slides were fix with 4% paraformaldehyde (Santa Cruz Biotechnology c #sc-281692) for 10 min followed by a wash with 1×PBS. Wells of interest were prepared for staining by blocking with 5% bovine serum albumin (Jackson ImmunoResearch Lab, c #001-000-162) in PBS for 30 min Primary, secondary, and pre-conjugated antibodies were diluted in 2.5% BSA Jackson ImmunoResearch Lab. c #001-000-162). Primary antibodies were incubated at RT for 1 h; following serial washes, secondary antibodies were incubated at RT for 30 min. After a final series of washes in PBS, DAPI was applied (1:1000 in PBS; BD Pharmingen, c #564907), the wells were stored at 4° C. until imaged with a Leica DM5500 B Microscope System For flow cytometry analysis, cells were fixed in 4% paraformaldehyde (Santa Cruz Biotechnology c #sc-281692) for 10 min and permeabilized with 0.05% saponin for nuclear protein staining (WT1). Briefly, cells were blocked using 1× human IgG (Sigma c #12511) for 30 min and then stained with the specified antibodies, 1 µg/1×10⁶ cells/100 µl IgG solution unless otherwise specified on the datasheet, for 1 h on ice. Cells were then washed twice in PBS and filtered immediately in a Corning™ Falcon™ Test Tube with Cell Strainer Snap Cap (Corning, c #352235) before sorting. Analysis was performed on a FACScanto machine using FACSDiva software. Unstained and single positive controls were used to perform area scaling, exclude autofluorescence, and perform fluorochrome compensation when needed. Cells were first gated based on forward and side scatters (FSC/SSC) to exclude dead cells and then gated for FSC-W/FSC-H and SSC-W/SSC-H to exclude potential duplets. Sorting gates were established based on the unstained population for each sample.

Aquaporin 1 (PT marker)—should be 80-95% positive.
N-cadherin (should be 80-95% positive)
MUC3 (should be 80-95% positive)
MUC1 (should be less than 5%)

3.7 Selection for Glomeruli Endothelial Cells (GEC)
1. Perform first GEC isolation from pelleted and counted cells from glomerular isolated fraction.
2. Do the first isolation use Myltenyi Order no: 130-091-935, CD31 bead conjugated antibody and follow manufacturer instructions.
3. After secondary samples are washed and magnetically separated with the autoMACS® Separator, using manufacturer instructions. After selection, cells are counted.
4. Plate the isolated positive cells after counting with Countess Cell Counter. Plate onto gelatin (Cell Biologics, c #6950) coated tissue culture plate in human endothelial cell medium (Cell Biologics, c #H1168;).
5. At P3, perform the second isolation for GEC to obtain a pure population as described in steps 1-3. Note: Through trial and error it was concluded that a second isolation is needed to yield more cell numbers and a purer yield.
6. Freeze down cells. Positive cells are counted using Countess Cell Counter. Sorted GEC are immediately frozen at 600,000 live cells/vial in Cryostor (Sigma Aldrich, #C2874-100ML).

3.8 Quality Control
After selection, seed 10,000 cell per well of an 8-well chamber slide (Fisher Scientific #08-774-26) for further QC testing. After 3 days of culture on chamber slides were fix with 4% paraformaldehyde (Santa Cruz Biotechnology c #sc-281692) for 10 min followed by a wash with 1×PBS. Wells of interest were prepared for staining by blocking with 5% bovine serum albumin (Jackson ImmunoResearch Lab, c #001-000-162) in PBS for 30 min Primary, secondary, and pre-conjugated antibodies were diluted in 2.5% BSA Jackson ImmunoResearch Lab. c #001-000-162). Primary antibodies were incubated at RT for 1 h; following serial washes, secondary antibodies were incubated at RT for 30 min. After a final series of washes in PBS, DAPI was applied (1:1000 in PBS; BD Pharmingen, c #564907), the wells were stored at 4° C. until imaged with a Leica DM5500 B Microscope System For flow cytometry analysis, cells were fixed in 4% paraformaldehyde (Santa Cruz Biotechnology c #sc-281692) for 10 min and permeabilized with 0.05% saponin for nuclear protein staining (WT1). Briefly, cells were blocked using 1× human IgG (Sigma c #12511) for 30 min and then stained with the specified antibodies, 1 µg/1×10⁶ cells/100 µl IgG solution unless otherwise specified on the datasheet, for 1 h on ice. Cells were then washed twice in PBS and filtered immediately in a Corning™ Falcon™ Test Tube with Cell Strainer Snap Cap (Corning, c #352235) before sorting. Analysis was performed on a FACScanto machine using FACSDiva software. Unstained and single positive controls were used to perform area scaling, exclude autofluorescence, and perform fluorochrome compensation when needed. Cells were first gated based on forward and side scatters (FSC/SSC) to exclude dead cells and then gated for FSC-W/FSC-H and SSC-W/SSC-H to exclude potential duplets. Sorting gates were established based on the unstained population for each sample.

Cells are tested for:
Ve Cadherin– (endothelial marker, Abcam #ab33168): should be 80-95% positive
CD31 (endothelial marker, BD Bioscience #561654): should be 80-95% positive
PDGFRB (Mesangial marker, R&D FAB1263F)—should be less than 5%
Nephrin (glomerular marker, Abcam #ab136894)—should be less than 5%.

Bibliography

1. Piwkowska A, Rogacka D, Audzeyenka I, Kasztan M, Angielski S, Jankowski M. Insulin increases glomerular filtration barrier permeability through PKGIα-dependent mobilization of BKCa channels in cultured rat podocytes. *Biochim Biophys Acta.* 2015; 1852(8):1599-1609.
2. Meezan E, Brendel K, Ulreich J, Carlson E C. Properties of a pure metabolically active glomerular preparation from rat kidneys. I. Isolation. *J Pharmacol Exp Ther.* 1973; 187(2):332-341.
3. Wang L, Tao T, Su W, Yu H, Yu Y, Qin J. A disease model of diabetic nephropathy in a glomerulus-on-a-chip microdevice. *Lab Chip.* 2017; 17(10):1749-1760.
4. Petrosyan A, Cravedi P, Villani V, et al. A glomerulus-on-a-chip to recapitulate the human glomerular filtration barrier (published correction appears in Nat Commun. 2019 Oct. 21; 10(1):4791).
5. Takemoto M, Asker N, Gerhardt H, et al. A new method for large scale isolation of kidney glomeruli from mice. *Am J Pathol.* 2002; 161(3):799-805.
6. Liu X, Fan Q, Yang G, Liu N, Chen D, Jiang Y, Wang L. Isolating glomeruli from mice: A practical approach for beginners._Exp Ther Med. 2013 May; 5(5):1322-1326.
7. Rush B M, Small S A, Stolz D B, Tan R J. An Efficient Sieving Method to Isolate Intact Glomeruli from Adult Rat Kidney. *J Vis Exp.* 2018; (141):10.3791/58162. Published 2018 Nov. 1. doi:10.3791/58162
8. Norgaard J O. A new method for the isolation of ultrastructurally preserved glomeruli. *Kidney Int.* 1976; 9(3): 278-285.
9. Yaoita E, Kurihara H, Sakai T, Ohshiro K, Yamamoto T. Phenotypic modulation of parietal epithelial cells of Bowman's capsule in culture. *Cell Tissue Res.* 2001; 304(3): 339-349
10. Cook W F, & Pickering G W A rapid method for separating glomeruli from rabbit kidney. Nature. 182 (4642), 1103-1104, (1958).
11. Akis N, Madaio M P. Isolation, culture, and characterization of endothelial cells from mouse glomeruli. Kidney Int. 2004 June; 65(6):2223-7.
12. McGinn S, Poronnik P, Gallery E D, Pollock C A. A method for the isolation of glomerular and tubulointerstitial endothelial cells and a comparison of characteristics with the human umbilical vein endothelial cell model. Nephrology (Carlton). 2004 August; 9(4):229-37

13. Rops A L, van der Vlag J, Jacobs C W, Dijkman H B, Lensen J F, Wijnhoven T J, van den Heuvel L P, van Kuppevelt T H, Berden J H. Isolation and characterization of conditionally immortalized mouse glomerular endothelial cell lines. Kidney Int. 2004 December; 66(6):2193-201.
14. Zeng Y, Deng H, Zhou X J, Wang Y. [Isolation, culture and identification of endothelial cells from rat glomeruli]. Zhonghua Bing Li Xue Za Zhi. 2005 April; 34(4):233-4. Chinese.
15. Menè P, Stoppacciaro A. Isolation and propagation of glomerular mesangial cells. Methods Mol Biol. 2009; 466:3-17.
16. Smeets B, Kabgani N, Moeller M J. Isolation and Primary Culture of Murine Podocytes with Proven Origin. Methods Mol Biol. 2016; 1397:3-10.
17. Green D F, Hwang K H, Ryan U S, Bourgoignie J J. Culture of endothelial cells from baboon and human glomeruli. Kidney Int. 1992 June; 41(6):1506-16. PubMed PMID:1501407.
18. Nagi A H, Kirkwood W. A quick method for the isolation of glomeruli from human kidney. *J Clin Pathol*. 1972; 25 (4):361.
19. Rush B M, Small S A, Stolz D B, Tan R J. An Efficient Sieving Method to Isolate Intact Glomeruli from Adult Rat Kidney. J Vis Exp. 2018 Nov. 1; (141).
20. Misra R P. Isolation of glomeruli from mammalian kidneys by graded sieving. *Am J Clin Pathol*. 1972; 58(2):135-139.
21. Yaoita E, Kurihara H, Sakai T, Ohshiro K, Yamamoto T. Phenotypic modulation of parietal epithelial cells of Bowman's capsule in culture. *Cell Tissue Res*. 2001; 304(3): 339-349.
22. Burlington H, Cronkite E P. Characteristics of cell cultures derived from renal glomeruli. *Proc Soc Biol Med*. 1973; 142(1):143-149.

All publications, nucleotide and amino acid sequence identified by their accession nos., patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed is:

1. A glomerulus on a chip (GOAC) device comprising at least three channels, at least two monolayers of cells and a glomerular renal filtration barrier, wherein the device does not include an artificial membrane separating layers of cells within the GOAC device,
    wherein the GOAC device comprises at least a first channel, a second channel and a third channel,
    wherein the first channel is in fluid communication with the second channel and wherein the second channel is in fluid communication with the third channel,
    wherein a gelified collagen is disposed throughout the second channel,
    wherein the first channel comprises a first monolayer comprised of podocytes disposed on the gelified collagen and a second monolayer comprised of glomerular endothelial cells disposed on the first monolayer, wherein an artificial membrane does not separate the first monolayer from the second monolayer,
    wherein the third channel is configured to collect filtrate.

2. The GOAC device of claim 1, wherein the podocytes are at least one of primary podocytes (hpPOD), immortalized podocytes (hiPOD), amniotic fluid derived podocytes (hAKPC-P) or a combination thereof.

3. The GOAC device of claim 1, wherein the podocytes and the glomerular endothelial cells are human.

4. The GOAC device of claim 1, wherein the podocytes and the glomerular endothelial cells are obtained from a subject that does not have a kidney disease or disorder or include immortalized glomerular endothelial cells.

5. A method of testing the effect of at least one test compound on the glomerulus-on-a-chip (GOAC) device of claim 1, the method comprising adding the at least one test compound to the first channel of the GOAC device and at least one of assessing the GOAC device microscopically or determining one or more physiological parameters of the GOAC device.

6. The method of claim 5, further comprising determining at least one of efficacy, side-effect, biosafety or mode of action of the at least one test compound.

7. The method of claim 5, wherein after the at least one test compound has been added to the first channel, the filtrate collected in the third channel is analyzed.

8. The GOAC device of claim 1, wherein the first channel is stacked on top of the second channel and the second channel is stacked on top of the third channel.

9. The method of claim 1, wherein the podocytes are indirectly disposed on the gelified collagen.

10. A method of providing a glomerulus on-a-chip (GOAC) device with at least a first channel, a second channel, and a third channel, the method comprising:
    loading the second channel with collagen;
    after gelification of the collagen to produce gelified collagen throughout the second channel, loading Rail the first channel with podocytes to form a first monolayer on the gelified collagen;
    loading glomerular endothelial cells (GEC) in the first channel to form a second monolayer disposed on the first monolayer;
    filling the first channel with growth medium, wherein the podocytes and the glomerular endothelial cells are seeded together in the first channel without an artificial membrane separating the first monolayer from the second monolayer; and
    a wherein the third channel is configured to collect filtrate, wherein the first channel is in fluid communication with the second channel and wherein the second channel is in fluid communication with the third channel.

11. The method of claim 10, wherein the podocytes are at least one of primary podocytes (hpPOD), immortalized podocytes (hiPOD), amniotic fluid derived podocytes (hAKPC-P) or a combination thereof.

12. The method of claim 10, wherein the collagen comprises collagen I.

13. The method of claim 10, comprising:
    adding FITC-conjugated albumin to the first channel; and
    determining that leakage of the FITC-conjugated albumin was prevented from 5 minutes to 60 minutes after adding the FITC-conjugated albumin to the first.

14. The method of claim 10, wherein the first channel is stacked on top of the second channel and the second channel is stacked on top of the third channel.

* * * * *

UNITED STATES PATENT AND TRADEMARK OFFICE
CERTIFICATE OF CORRECTION

| | |
|---|---|
| PATENT NO. | : 11,840,683 B2 |
| APPLICATION NO. | : 16/870480 |
| DATED | : December 12, 2023 |
| INVENTOR(S) | : Perin et al. |

It is certified that error appears in the above-identified patent and that said Letters Patent is hereby corrected as shown below:

On the Title Page

On page 2, in Column 2, under Item (56) "Other Publications", Line 25, delete "Micro?uidic" and insert --Microfluidic-- therefor In the Claims In Column 42, Line 34, in Claim 1, delete "harrier," and insert --barrier,-- therefor In Column 43, Line 10, in Claim 9, delete "method" and insert --GOAC device-- therefor In Column 43, Line 17, in Claim 10, after "loading", delete "Rail"

In Column 44, Line 4, in Claim 10, before "wherein", delete "a"

Signed and Sealed this
Twenty-third Day of January, 2024

Katherine Kelly Vidal
*Director of the United States Patent and Trademark Office*